United States Patent
Weiss et al.

(10) Patent No.: US 10,544,405 B2
(45) Date of Patent: Jan. 28, 2020

(54) CAS9-NUCLEIC ACID COMPLEXES AND USES RELATED THERETO

(71) Applicant: EMORY UNIVERSITY, Atlanta, GA (US)

(72) Inventors: David S. Weiss, Decatur, GA (US); Arash Grakoui, Decatur, GA (US); Timothy R. Sampson, Los Angeles, CA (US); Aryn Alaine Price, Tipton, MO (US)

(73) Assignee: Emory University, Atlanta, GA (US)

( * ) Notice: Subject to any disclaimer, the term of this patent is extended or adjusted under 35 U.S.C. 154(b) by 532 days.

(21) Appl. No.: 14/760,113

(22) PCT Filed: Jan. 15, 2014

(86) PCT No.: PCT/US2014/011716
§ 371 (c)(1),
(2) Date: Jul. 9, 2015

(87) PCT Pub. No.: WO2014/113493
PCT Pub. Date: Jul. 24, 2014

(65) Prior Publication Data
US 2015/0353905 A1    Dec. 10, 2015

Related U.S. Application Data

(60) Provisional application No. 61/753,046, filed on Jan. 16, 2013, provisional application No. 61/905,368, filed on Nov. 18, 2013.

(51) Int. Cl.
| | | |
|---|---|---|
| *C12N 9/16* | (2006.01) | |
| *C12N 15/90* | (2006.01) | |
| *C12N 15/82* | (2006.01) | |
| *C12N 9/22* | (2006.01) | |
| *C07K 14/195* | (2006.01) | |

(52) U.S. Cl.
CPC ................................. *C12N 9/16* (2013.01)

(58) Field of Classification Search
None
See application file for complete search history.

(56) References Cited

U.S. PATENT DOCUMENTS

| | | | |
|---|---|---|---|
| 4,897,355 A | 1/1990 | Eppstein et al. | |
| 4,946,787 A | 8/1990 | Eppstein et al. | |
| 5,049,386 A | 9/1991 | Eppstein et al. | |
| 5,208,036 A | 5/1993 | Eppstein et al. | |
| 5,356,802 A | 10/1994 | Chandrasegaran | |
| 5,436,150 A | 7/1995 | Chandrasegaran | |
| 5,466,468 A | 11/1995 | Schneider et al. | |
| 5,487,994 A | 1/1996 | Chandrasegaran | |
| 5,580,571 A | 12/1996 | Hostetler | |
| 5,626,869 A | 5/1997 | Nyqvist et al. | |
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,466 A | 10/2000 | Barbas, III et al. | |
| 6,200,759 B1 | 3/2001 | Dove et al. | |
| 6,242,568 B1 | 6/2001 | Barbas, III et al. | |
| 6,326,198 B1 | 12/2001 | Emerson et al. | |
| 6,335,195 B1 | 1/2002 | Rodgers et al. | |
| 6,338,942 B2 | 1/2002 | Kraus et al. | |
| 6,383,481 B1 | 5/2002 | Ikehara et al. | |
| 6,387,383 B1 | 5/2002 | Dow et al. | |
| 6,410,248 B1 | 6/2002 | Greisman et al. | |
| 6,453,242 B1 | 9/2002 | Eisenberg et al. | |
| 6,468,989 B1 | 10/2002 | Chang et al. | |
| 6,517,847 B2 | 2/2003 | Dow et al. | |
| 6,534,261 B1 | 3/2003 | Cox, III et al. | |
| 6,607,882 B1 | 8/2003 | Cox, III et al. | |
| 6,890,554 B2 | 5/2005 | Jessee et al. | |
| 7,166,298 B2 | 1/2007 | Jessee et al. | |
| 8,697,359 B1 | 4/2014 | Zhang | |
| 8,865,406 B2 | 10/2014 | Zhang et al. | |
| 8,889,418 B2 | 11/2014 | Zhang et al. | |
| 8,906,616 B2 | 12/2014 | Zhang et al. | |
| 8,937,157 B2 | 1/2015 | Ledbetter et al. | |

(Continued)

FOREIGN PATENT DOCUMENTS

| | | |
|---|---|---|
| CN | 103911376 A | 7/2014 |
| WO | 91/16024 A1 | 10/1991 |

(Continued)

OTHER PUBLICATIONS

Genbank Accession No. CP000439 (retrieved from the internet: <<https://www.ncbi.nlm.nih.gov/nuccore/118422521/>>, retrieved on Mar. 20, 2018).*
O'Connell et al. (Programmable RNA recognition and cleavage by CRISPR/Cas9, Nature, Dec. 11, 2014, vol. 516, pp. 263-266, Epub Sep. 28, 2014 (Year: 2014)).*
Belfort, 1997, Homing endonucleases: keeping the house in order, Nucleic Acids Res 25(17):3379-3388.
Bessis, 2004, Immune responses to gene therapy vectors: influence on vector function and effector mechanisms, Gene Ther 11:S10-S17.

(Continued)

*Primary Examiner* — Suzanne M Noakes
*Assistant Examiner* — Jae W Lee
(74) *Attorney, Agent, or Firm* — Kilpatrick Townsend & Stockton LLP

(57) ABSTRACT

This disclosure relates to Cas9-nucleic acid complexes and uses related thereto. In certain embodiments, the disclosure contemplates transgenic plants and animals genetically engineered to express Cas9-nucleic acid complexes disclosed herein. In certain embodiments, the disclosure relates to methods of treating or preventing, diseases, conditions, cancer, viral infections or other pathogenic infection using vectors configured to express a Cas9-nucleic acid complex disclosed herein.

17 Claims, 12 Drawing Sheets
Specification includes a Sequence Listing.

(56) References Cited

U.S. PATENT DOCUMENTS

| | | | |
|---|---|---|---|
| 8,945,839 B2 | 2/2015 | Zhang | |
| 8,993,233 B2 | 3/2015 | Zhang et al. | |
| 9,322,037 B2 | 4/2016 | Liu et al. | |
| 9,487,802 B2 | 11/2016 | Quake et al. | |
| 9,834,791 B2 * | 12/2017 | Zhang | C12N 15/63 |
| 2004/0203124 A1 | 10/2004 | King et al. | |
| 2004/0265325 A1 | 12/2004 | Diamond et al. | |
| 2005/0064474 A1 | 3/2005 | Urnov et al. | |
| 2005/0222075 A1 | 10/2005 | Herweijer et al. | |
| 2006/0106321 A1 | 5/2006 | Lewinsky et al. | |
| 2006/0188987 A1 | 8/2006 | Guschin et al. | |
| 2008/0131962 A1 | 6/2008 | Miller | |
| 2009/0017543 A1 | 1/2009 | Wilkes et al. | |
| 2009/0047272 A1 | 2/2009 | Appelbaum et al. | |
| 2010/0076057 A1 | 3/2010 | Sontheimer et al. | |
| 2011/0002889 A1 | 1/2011 | Barrangou et al. | |
| 2011/0023144 A1 | 1/2011 | Weinstein et al. | |
| 2011/0177594 A1 | 7/2011 | Shushan et al. | |
| 2012/0122213 A1 | 5/2012 | Lai et al. | |
| 2013/0046230 A1 | 2/2013 | Lewis, Jr. et al. | |
| 2013/0136768 A1 | 5/2013 | Picker et al. | |
| 2013/0149286 A1 | 6/2013 | Chretien et al. | |
| 2013/0165769 A1 | 6/2013 | Gerrans et al. | |
| 2013/0330778 A1 | 12/2013 | Zeiner et al. | |
| 2014/0017212 A1 | 1/2014 | Rebar | |
| 2014/0068797 A1 | 3/2014 | Doudna et al. | |
| 2014/0179770 A1 * | 6/2014 | Zhang | C12N 15/86 514/44 R |
| 2014/0186843 A1 | 7/2014 | Zhang et al. | |
| 2014/0186958 A1 | 7/2014 | Zhang et al. | |
| 2014/0273037 A1 | 9/2014 | Wu | |
| 2014/0273233 A1 | 9/2014 | Chen et al. | |
| 2014/0295556 A1 | 10/2014 | Joung et al. | |
| 2014/0315985 A1 | 10/2014 | May et al. | |
| 2014/0342457 A1 | 11/2014 | Mali et al. | |
| 2014/0342458 A1 | 11/2014 | Mali et al. | |
| 2014/0349400 A1 | 11/2014 | Jakimo et al. | |
| 2014/0356958 A1 | 12/2014 | Mali et al. | |
| 2014/0357523 A1 | 12/2014 | Zeiner et al. | |
| 2015/0020223 A1 | 1/2015 | Zhang et al. | |
| 2015/0024500 A1 | 1/2015 | Yu et al. | |
| 2015/0045546 A1 | 2/2015 | Siksnys et al. | |
| 2015/0050699 A1 | 2/2015 | Siksnys et al. | |
| 2015/0056705 A1 | 2/2015 | Conway et al. | |
| 2015/0071898 A1 | 3/2015 | Liu et al. | |
| 2015/0071903 A1 | 3/2015 | Liu et al. | |
| 2015/0098954 A1 | 4/2015 | Hyde et al. | |
| 2015/0176006 A1 | 6/2015 | Krause et al. | |
| 2015/0232881 A1 | 8/2015 | Glucksmann et al. | |
| 2015/0232883 A1 | 8/2015 | Dahlman et al. | |
| 2015/0353905 A1 | 12/2015 | Weiss et al. | |
| 2015/0368670 A1 | 12/2015 | Quake et al. | |
| 2015/0376583 A1 | 12/2015 | Quake et al. | |
| 2016/0017301 A1 | 1/2016 | Khalili et al. | |
| 2016/0040165 A1 | 2/2016 | Howell et al. | |
| 2016/0060655 A1 | 3/2016 | Quake et al. | |
| 2016/0287678 A1 | 10/2016 | Wang | |
| 2016/0317677 A1 | 11/2016 | Bhatia et al. | |
| 2016/0346360 A1 | 12/2016 | Quake et al. | |
| 2016/0346361 A1 | 12/2016 | Quake et al. | |
| 2016/0346362 A1 | 12/2016 | Quake et al. | |
| 2016/0348074 A1 | 12/2016 | Quake et al. | |
| 2016/0350476 A1 | 12/2016 | Quake et al. | |

FOREIGN PATENT DOCUMENTS

| | | |
|---|---|---|
| WO | 91/17424 A1 | 11/1991 |
| WO | 2007/025097 A2 | 3/2007 |
| WO | 2007/071994 A2 | 6/2007 |
| WO | 2010/056728 A1 | 5/2010 |
| WO | 2010/075424 A2 | 7/2010 |
| WO | 2013/029919 A1 | 3/2013 |
| WO | 2013/141680 A1 | 9/2013 |
| WO | 2013/142578 A1 | 9/2013 |
| WO | 2013/176772 A1 | 11/2013 |
| WO | 2013/188037 A2 | 12/2013 |
| WO | 2014/071235 A1 | 5/2014 |
| WO | 2014/093479 A1 | 6/2014 |
| WO | 2014/093595 A1 | 6/2014 |
| WO | 2014/099744 A1 | 6/2014 |
| WO | 2014/124226 A1 | 8/2014 |
| WO | 2014/143381 A1 | 9/2014 |
| WO | 2014/150624 A1 | 9/2014 |
| WO | 2014/165349 A1 | 10/2014 |
| WO | 2014/172470 A2 | 10/2014 |
| WO | 2014204726 A1 | 12/2014 |
| WO | 2015/006290 A1 | 1/2015 |
| WO | 2015/006747 A2 | 1/2015 |
| WO | 2015/031775 A1 | 3/2015 |
| WO | 2015/034872 A2 | 3/2015 |
| WO | 2015053995 A1 | 4/2015 |
| WO | 2015/066557 A1 | 5/2015 |
| WO | 2015/089465 A1 | 6/2015 |
| WO | 2015/105928 A1 | 7/2015 |
| WO | 2015/126927 A2 | 8/2015 |
| WO | 2015/153889 A2 | 10/2015 |
| WO | 2015/184259 A1 | 12/2015 |

OTHER PUBLICATIONS

Bernard, 2007, Gene expression of genital human papillomaviruses and considerations on potential antiviral approaches. Antivir.Ther. 7:219-237.

Bhaya, 2011, CRISPR-Cas systems in bacteria and archea: versitle small RNAs for adaptive defense and regulation, Annu Rev Genet 45:273-297.

Bitinaite, 1998, FokI dimerization is required for DNA cleavage, PNAS 95(18):10570-10575.

Bi, 2014, High-efficiency targeted editing of large viral genomes by RNA-guided Nucleases, PLoS Pathogens 10(5):e1004090.

Bloom, 2013, Inactivatoin of hepatitis B virus replication in cultured cells and in vivo with engineered transcription activator-like effector nucleases, Mol Ther 21:1889-1897.

Chang, 2013, Genome editing with RNA-guided Cas9 nuclease in zebrafish embryos, Cell Res 23:465-472.

Carter, 2011, Introduction to current and future protein therapeutics: a protein engineering perspective, Exp Cell Res 317:1261-1269.

Chen, 2013, Dynamic imaging of genomic loci in living human cells by an optimized CRISPR/Cas system, Cell 155:1479-1491.

Dampier, 2014, HIV excision utilizing CRISPR/Cas9 technology: attacking the proviral quasispecies in reservoirs to achieve a cure, MOJ Immunology 1(4):00022.

Cong, 2013, Multiplex Genome Engineering Using CRISPR/Cas Systems, Science 339:819-823.

Database UniProt [Online] Jan. 9, 2007, "RecName: Full=CRISPR-associated endonuclease Cas9; EC=3/1", retrieved from EBI accession No. UNIPROT:A0Q5Y3; Database accession No. A0Q5Y3.

Davis, 2008, Nanotherapeutic particles: an emerging treatment modality for cancer, Nat Rev Drug Disc 7(9):771-782.

Deng, 2009, Hepatitis B virus as a gene delivery vector activating foreign antigenic T cell response that abrogates viral expression in mouse models, Hepatology 50(5):1380.

DeGroot, 2009, Reducing risk, improving outcomes: bioengineering less immunogenic protein therapeutics, Clin Imm 131:189-201.

Duellman, 2009, Phosphorylation sites of Epstein-Barr Virus EBNA1 regulate its function, J Gen Virol. 90(9):2251-9.

Extended European Search Report for Application No. 14740738.1 dated Jun. 2, 2016.

Favre, 2003, Latent hepatitis B virus (HBV) infection and HBV DNA integratoin is associated with further transformation of hepatoma cells in vitro, Altex 20:131-142.

Ebina, 2013, Harnessing the CRISPR/Cas9 system to disrupt latent HIV-1 provirus, Sci Rep 3:2510.

Gaj, 2013, ZFN, TALEN, and CRISPR/Cas-based methods for genome engineering, Trends Biotech 31(7):397-405.

Gasiunas et al., "Cas9-crRNA ribonucleoprotein complex mediates specific DNA cleavage for adaptive immunity in bacteria", Pro-

(56) References Cited

OTHER PUBLICATIONS ceedings of the National Academy of Sciences, vol. 109, No. 39, Sep. 25, 2012, pp. E2579-E2586.
Gao, 2007, Nonviral gene delivery: what we know and what is next, AAPS J 9(1):E92-E104.
Gilbert, 2013, CRISPR-mediated modular RNA-guided regulation of transcription in eukaryotes, Cell 154:442-451.
Glatzel, 2000, Adenoviral and adeno-associated viral transfer of genes to the peripheral nervous system PNAS 97(1):442-447.
Green, 2013, Epstein-Barr virus infection and posttransplant lymphoproliferative disorder, Am J Transplant 13(Suppl 3):41-54.
Gomaa, 2014, Programmable removal of bacterial strains by use of genome-targeting CRISPR-Cas systems, MBio 5:e00928.
Griffin, 2013, Human papillomavirus infection is inhibited by host autophagy in primary human keratinocytes, Virology 437(1):12-19.
Guo, 2012, Recent advances in non-viral vectors for gene delivery, Acc Chem Res 45(7):971-979.
Grosse, 2011, Meganuclease-mediated inhibition of HSV1 infection in cultured cells, Mol Ther 19(4):694-702.
Harrison, 2014, A CRISPR view of development, Genes and Development 28:1859-1872.
Hoshino, 2008, The number of herpes simplex virus-infected neurons and the number of viral genome copies per neuron correlate with latent viral load in ganglia, Virology 372(1):56-63.
Horvath, 2010, CRISPR/Cas, the immune system of bacteria and archaea, Science 327:167-170.
Hsu, 2013, DNA targeting specificity of RNA-guided Cas9 nucleases, Nature Biotechnology 31(9):827-832.
Hsu, 2014, Development and applications of CRISPR-Cas9 for genome engineering, Cell 157:1262.
Hu, 2014, Disruption of HPV16-E7 by CRISPR/Cas System Induces Apoptosis and Growth Inhibition in HPV16 Positive Human Cervical Cancer Cells, Biomed Res Int 31(3):209-9.
Hu, 2014, RNA-directed gene editing specifically eradicates latent and prevents new HIV-1 infection, PNAS 111:11461-11466.
Huang, 1994, The activity of the Pseudorabies virus latency-associated transcript promoter is dependent on its genomic location in Herpes Simplex Virus recombinatnats as well as on the type of cell infected, J Virol 68(3):1972-1976.
Hui, 1996, High-efficiency loading transfection and fusion of cells by electroporation in two-phase polymer systems, Biophys J 71:1123-1130.
International Search Report for Application No. PCT/US2014/011716 dated May 14, 2014.
Hwang, 2013, Efficient genome editing in zebrafish using a CRISPR-Cas system, Nat Biotech 31:227-229.
Jafari, 2012, Nonviral approach for targeted nucleic acid delivery, Curr Med Chem 19:197-208.
Jinek, 2012, A programmable dual-RNA-guided DNA endonuclease in adaptive bacterial immunity, Science 337:816-821.
Jinek, 2013, RNA-programmed genome editing in human cells, Elife 2:e00471.
Joung, 2013, TALENs: a widely applicable technology for targeted genome editing, Nat Rev Mol Cell Bio 14:49-55.
Kennedy, 2003, EBNA1, a Bifunctional Transcription Activator, Mol Cell Biol 23(19):6901-6908.
Kennedy, 2014, Inactivation of the Human Papillomavirus E6 or E7 Gene in Cervical Carcinoma Cells by Using a Bacterial CRISPR/Cas RNA-Guided Endonuclease, J Virol 88(20):11965-11972.
Kim, 1994, Chimeric restriction endonuclease, PNAS 91:883-887.
Kim, 2014, Highly efficient RNA-guided genome editing in human cells via delivery of purified Cas9 ribonucleoproteins, Genome Res 24(6):1012-1019.
Kuchta, 2012, Structural modelling and mutagenesis of Human Cytomegalovirus alkaline nuclease UL98, J Gen Virl 93(1):130-138.
Labrou, 2010, Random mutagenesis methods for in vitro directed enzyme evolution, Curr Protein Pep Sci 11(1):91-100.

Lee, 2001, Enhancing transfection efficiency using polyethylene glycol grafted polyethylenimine and fusogenic peptide, Biotechnol Bioprocess Eng 6:269-273.
Li, 1992, Functional domains in Fok I restriction endonuclease, PNAS 89:4275-4279.
Lin, 2001, Differential Expression of Tissue-Specific Promoters by Gene Gun, Brit J Derm 144(1):34-39.
Lin, 2014, The CRISPR/Cas9 system facilitates clearance of the intrahepatic HBV templates in vivo, Mol Ther Nucleic Acids 3:e186.
Liu, 2004, CMV enhancer/human PDGF-beta promoter for neuron specific transgene expression, Gene Ther 11(1):52-60.
Liu, 2006, Encapsulated ultrasound microbubbles: therapeutic application in drug/gene delivery, J Controlled Release 114(1):89-99.
Lorenceau, 2005, Generation of polymerosomes from double-emulsions, Langmuir 21(20):9183-6.
Ma, 2013, A guide RNA sequence design platform for the CRISPR/Cas9 system for model organisms, Biomed Res Int 270805.
Mali, 2013, RNA-guided human genome engineering via Cas9, Science 339:823-826.
Mali, 2013, Cas9 as a versatile tool for engineering biology, Nat Meth 10(10):957.
Marusawa, 2000, Latent hepatitis B virus infection in healthy individuals with antibodies to hepatitis core B antigen, Hepatology 31(2):488-495.
Munger, 2004, Mechanisms of human papillomavirus-induced oncogenesis, J Virol 78(21):11451-11460.
Nishimasu, 2014, Crystal structure of Cas9 in complex with guide RNA and target DNA, Cell 156:935-949.
Nozaki, 2003, Enhancement of ultrasound-mediated gene transfection by membrane modification, J Gene Med 5(12):1046-1055.
Prausnitz, 1993, Electroporation of mammalian skin: a mechanism to enhance transdermal drug delivery, PNAS 90:10504-10508.
Prausnitz, 2008, Transdermal drug delivery, Nat Biotech 26(11):1261-1268.
Puren, 2010, Laboratory operations, specimen processing, and handling for viral load testing and surveillance, J Inf Dis 201(Suppl 1):S27-36.
Qi, 2013, Repurposing CRISP as an RNA-guided platform for sequence-specific control of gene expression, Cell 152:1173-1183.
Qi, 2014, A versatile framework for microbial engineering using synthetic non-coding RNAs, Nat Rev Mic 12:341-354.
Qu, 2013, Zinc-finger-nucleases mediate specific and efficient excision of HIV-1 proviral DNA from infected and latently infected human T cells, Nucl Ac Res 41(16):7771-7782.
Qu, 2014, Zinc finger nuclease: a new approach for excising HIV-1 proviral DNA from infected human T cells, Mol Biol Rep 41:5819-5827.
Quarleri, 2014, Core promoter: a critical region where the hepatitis B virus maeks decisions, World J Gast 20(2):425-435.
Rojanasakul, 1994, Targeted gene delivery to alveolar macrophages via Fc receptor-mediated endocytosis, Pharm Res 11(12):1731-6.
Ruf, 2000, Epstein-Barr virus small RNAs potentiate tumorigenicity of Burkitt lymphoma cells independently of an effect on apoptosis, J Virol 74(21):10223-10228.
Sampson et al., "A CRISPR/Cas system mediates bacterial innate immune evasion and virulence", Nature, vol. 497, May 9, 2013, pp. 254-257.
Sapranauskas et al., "The *Streptococcus thermophiles* CRISPR/Cas system provides immunity in *Escherichia coli*", Nucleic Acids Research, 2011, vol. 39, No. 21, pp. 9275-9282.
Schiffer, 2012, Targeted DNA mutagenesis for the cure of chronic viral infections, J Virol 88(17):8920-8936.
Schiffer, 2013, Predictors of hepatitis B cure using gene therapy to deliver DNA cleavage enzymes: a mathematical modeling approach, PLoS Comp Biol 9(7):e1003131.
Schwank, 2013, Functional repair of CFTR by CRISPR/Cas9 in intestinal stem cell organoids of cystic fibrosis patients, Cell Stem Cell 13(6):653-8.
Seeger, 2014, Targeting Hepatitis B Virus with CRISPR/Cas9, Mol Ther Nucleic Acids 3:e216.
Silva, 2011, Meganucleases and other tools for targeted genome engineering, Curr Gene Ther 11(1):11-27.

(56) References Cited

OTHER PUBLICATIONS

Smith, 2007, Perspectives on transdermal ultrasound mediated drug delivery, Int J Nanomed 2(4):585-594.
Sternberg, 2014, DNA interrogation by the CRISPR RNA-guided endonuclease Cas9, Nature 507(7490):62-67.
Surovaya, 2010, Complex of the herpes simplex virus initiator protein UL9 with DNA as a platform for the design of a new type of antiviral drugs, Biophysics 55(2):204-214.
Terns, 2011, CRISPR-based adaptive immune systems, Curr Op Microb 14:321-327.
Turner, 2011, Administration of substances to laboratory animals: routes of administration and factors to consider, J Am Assoc Lab Anim Sci 50(5):600-613.
Wah, 1998, Structure of FokI has implications for DNA cleavage, PNAS 95:10564-10569.
Wang, 2013, One-step generation of mice carrying mutations in multiple genes by CRISPR/Cas-mediated genome engineering, Cell 153:910-918.
Wang, 2014, RNA-guided endonuclease provides a therapeutic strategy to cure latent herpesviridae infection, PNAS 111(36):13157-13162.
Wang, 2014, State-of-the-art human gene therapy: Part I. Gene delivery technologies, Discov Med 18(97):67-77.
Wang, 2014, State-of-the-art human gene therapy: Part II. Gene therapy strategies and applications, Discov Med 18(98):151-161.
Westergaard, 2001, Modulation of keratinocyte gene expression and differentiation by PPAR-selective ligands and tetradecyltheioacetic acid, J Invest Dermatol 116(5):702-12.
Wiedenheft, 2012, RNA-guided genetic silencing systems in bacteria and archaea, Nature 482:331-338.
Woodland, 2004, Jump-starting the immune system: prime-boosting comes of age, Trends Immunol 25(2):98.
Wu, 1987, Receptor-mediated in vitro gene transformation by a soluble DNA carrier system, J Biol Chem 262:4429.
Xiao, 2013, Chromosomal deletions and inversions mediated by TALENS and CRISPR/Cas in zebrafish, Nucl Acids Res 1-11.
Xue, 2014, Efficient gene knock-out and knock-in with transgenic Cas9 in *Drosophila*, G3 4:925-929.
Yang, 1990, In vivo and in vitro gene transfer to mammalian somatic cells by particle bombardment, PNAS 87:9568-9572.
Yang, 2013, One-step generation of mice carrying reporter and conditional alleles by CRISPR/Cas-mediated genome enginneering, Cell 154:1370-1379.
Young, 2003, Epstein-Barr Virus and oncogenesis: from latent genes to tumors, Oncogene 22(33):5108-5121.
Zensi, 2009, Albumin nanoparticles targeted with Apo E enter the CNS by transcytosis and are delivered to neurons, J Control Release 137:78-86.
Zhang, 2014, Gene transfection in complex media using PCBMAEE-PCBMA copolymer with both hydrolytic and zwitterionic blocks, Biomaterials 35(27):7909-18.
Zheng, 2006, Papillomavirus genome structure, expression, and post-transcriptional regulation, Front Biosci 11:2286-2302.
Godbole et al., "crispr-associated large prtein (provisional), putative [*Francisella tularensis* subsp. *novicida* FTE]", GenBank: EDX27228. 1, Jul. 23, 2008.
Jones et al., "Repression of bacterial lipoprotein production by Francisella novicida facilitates evasion of innate immune recognition", Cellular Microbiology (2012) 14(10), pp. 1531-1543.
Timothy R. Sampson et al., "Author Correction: A Crispr/Cas system mediates bacterial innate immune evasion and virulence", Nature, vol. 570, Jun. 13, 2019, pp. E30-E31 (2 pages).

* cited by examiner

Arginine-Rich Motif

S.pyogenes/1-1368
L.monocytogenes/1-1334
L.salivarius/1-1149
N.meningitidis/1-1082
L.pneumophila/1-1372
Burkholdariales/1-1428
C.jejuni/1-984
F.novicida/1-1629

```
TAEATRLKRTARRRYTRRKNR ICYLQEIFSNEMAKV--93
TAADRRMNRTARRRIERRRNR ISYLQEIFALEMANI--93
TAAERRGFRTQRRRLNRRKWRLKLLEEIFDPYMAEV--79
LAMARRLARSVRRLTRRRAHRLLRARRLLKREGVLQ--93
LSQAQ----RRATRHRVRNKKRNQFVKRVALQLFQ----82
FSSKS---RTAVRHRVRSYKGFDLRRRLLLLVAEYQLL 83
LALPRRLARSARKRLARRKARLNHLKHLIANEFKLN--79
LLMNN---RTARRHQRRGIDRKQLVKRLFKLIWTEQ--82
```

↑
R59

RuvC-III

```
750 VMGRHKPENIVIEMARENQTTQK---GQKNSR----ERMKRI
754 IMGY-PPQTIVVEMARENQTTVK---GKNNSR----PRYKSL
747 AMKC-EPTSIAIEFTREKRRSK-------LTN----TRYKKI
494 RYG--SPARIHIETAREVGKSFK---DRKEIEKRQEENRKDR
634 RMVQRLAYE IAMAKWEQIKHIP--DNSSLLIPIYLEQNRFEF
687 KAIDRNSWEVAKRIAEEVKKSVDFTNGTVKIPVAIEANSFNF
469 KYG--KVHKINIELAREVGKNHS---QRAKIEKEQNENYKAK
864 KMATILAKNIVDDNWQNIKQVLS-AKHQLHIPIITESNAFEF
```

↑
D876

RuvC-IV

```
Q---------FYKVREINNYHHAHDAYLNAVVGTALIKKYP- 1002
Q---------LYKVREVNDYHHAHDAYLNGVVANTLLKVYP- 1005
E---------LIKNREVNDYHHAIDGYLTTFVGQYLYKVYP- 992
G---------LRKVRAENDRHHALDAVVAGSTVAMQQKIT- 742
SKQEPK----LVKSRQQSFPSHAIDATLTMSIGLKEFPQFS- 927
AEYRPE----FRKPKVQPVASHSIDAMCIYLAACSD-PFKT- 976
G---------FSAKDRNNHLHHAIDAVIIAYANNSIVKAFS- 726
EKVDSDIQAYAKGDKPQASYSHLIDAMLAFCIAADEHRNDGS 1181
```

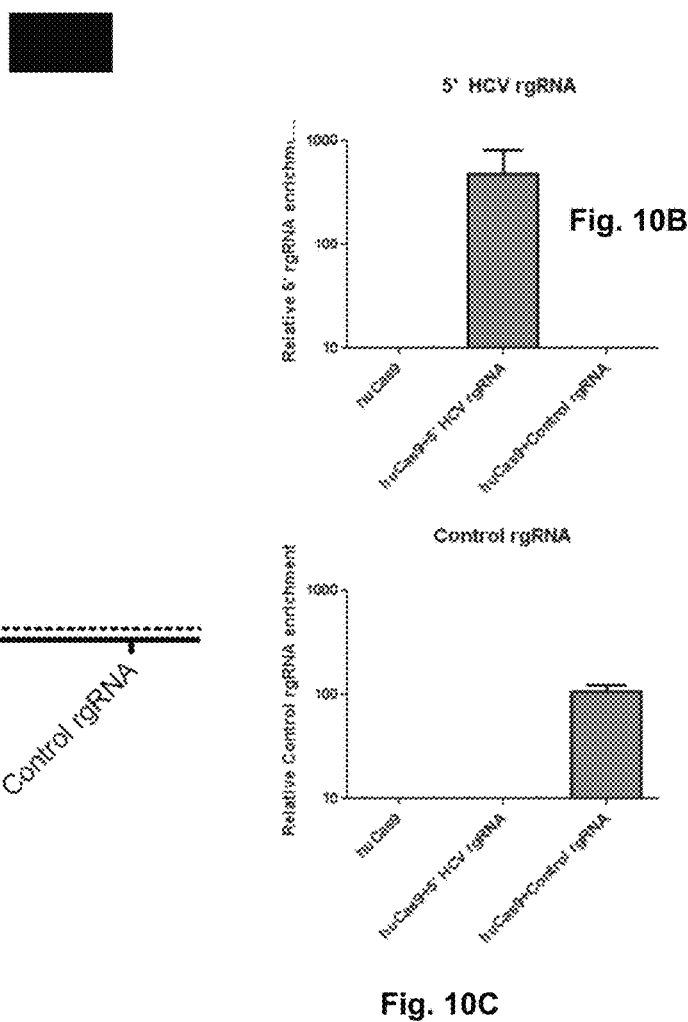

SEQUENCE LISTING

<160> NUMBER OF SEQ IDS NOS: 46

<210> SEQ ID NO 1
<211> LENGTH: 1629
<212> TYPE: PRT
<213> ORGANISM: Artificial Sequence
<220> FEATURE:
<223> OTHER INFORMATION: synthetic construct

<400> SEQUENCE: 1

Met Asn Phe Lys Ile Leu Pro Ile Ala Ile Asp Leu Gly Val Lys Asn
1               5                   10                  15

Thr Gly Val Phe Ser Ala Phe Tyr Gln Lys Gly Thr Ser Leu Glu Arg
            20                  25                  30

Leu Asp Asn Lys Asn Gly Lys Val Tyr Glu Leu Ser Lys Asp Ser Tyr
        35                  40                  45

Thr Leu Leu Met Asn Asn Arg Thr Ala Arg Arg His Gln Arg Arg Gly
    50                  55                  60

Ile Asp Arg Lys Gln Leu Val Lys Arg Leu Phe Lys Leu Ile Trp Thr
65                  70                  75                  80

Glu Gln Leu Asn Leu Glu Trp Asp Lys Asp Thr Gln Gln Ala Ile Ser
                85                  90                  95

Phe Leu Phe Asn Arg Arg Gly Phe Ser Phe Ile Thr Asp Gly Tyr Ser
            100                 105                 110

Pro Glu Tyr Leu Asn Ile Val Pro Glu Gln Val Lys Ala Ile Leu Met
        115                 120                 125

Asp Ile Phe Asp Asp Tyr Asn Gly Glu Asp Asp Leu Asp Ser Tyr Leu
    130                 135                 140

Lys Leu Ala Thr Glu Gln Glu Ser Lys Ile Ser Glu Ile Tyr Asn Lys
145                 150                 155                 160

Leu Met Gln Lys Ile Leu Glu Phe Lys Leu Met Lys Leu Cys Thr Asp
                165                 170                 175

Ile Lys Asp Asp Lys Val Ser Thr Lys Thr Leu Lys Glu Ile Thr Ser
            180                 185                 190

Tyr Glu Phe Glu Leu Leu Ala Asp Tyr Leu Ala Asn Tyr Ser Glu Ser
        195                 200                 205

Leu Lys Thr Gln Lys Phe Ser Tyr Thr Asp Lys Gln Gly Asn Leu Lys
    210                 215                 220

Glu Leu Ser Tyr Tyr His His Asp Lys Tyr Asn Ile Gln Glu Phe Leu
225                 230                 235                 240

Lys Arg His Ala Thr Ile Asn Asp Arg Ile Leu Asp Thr Leu Leu Thr
                245                 250                 255

Asp Asp Leu Asp Ile Trp Asn Phe Asn Phe Glu Lys Phe Asp Phe Asp
            260                 265                 270

Lys Asn Glu Glu Lys Leu Gln Asn Gln Glu Asp Lys Asp His Ile Gln
        275                 280                 285

Ala His Leu His His Phe Val Phe Ala Val Asn Lys Ile Lys Ser Glu
    290                 295                 300

Met Ala Ser Gly Gly Arg His Arg Ser Gln Tyr Phe Gln Glu Ile Thr
305                 310                 315                 320

Asn Val Leu Asp Glu Asn Asn His Gln Glu Gly Tyr Leu Lys Asn Phe
                325                 330                 335

Cys Glu Asn Leu His Asn Lys Lys Tyr Ser Asn Leu Ser Val Lys Asn
            340                 345                 350

Leu Val Asn Leu Ile Gly Asn Leu Ser Asn Leu Glu Leu Lys Pro Leu

-continued

```
              355                 360                 365
Arg Lys Tyr Phe Asn Asp Lys Ile His Ala Lys Ala Asp His Trp Asp
370                 375                 380

Glu Gln Lys Phe Thr Glu Thr Tyr Cys His Trp Ile Leu Gly Glu Trp
385                 390                 395                 400

Arg Val Gly Val Lys Asp Gln Asp Lys Lys Asp Gly Ala Lys Tyr Ser
                405                 410                 415

Tyr Lys Asp Leu Cys Asn Glu Leu Lys Gln Lys Val Thr Lys Ala Gly
                420                 425                 430

Leu Val Asp Phe Leu Leu Glu Leu Asp Pro Cys Arg Thr Ile Pro Pro
                435                 440                 445

Tyr Leu Asp Asn Asn Asn Arg Lys Pro Pro Lys Cys Gln Ser Leu Ile
450                 455                 460

Leu Asn Pro Lys Phe Leu Asp Asn Gln Tyr Pro Asn Trp Gln Gln Tyr
465                 470                 475                 480

Leu Gln Glu Leu Lys Lys Leu Gln Ser Ile Gln Asn Tyr Leu Asp Ser
                485                 490                 495

Phe Glu Thr Asp Leu Lys Val Leu Lys Ser Ser Lys Asp Gln Pro Tyr
                500                 505                 510

Phe Val Glu Tyr Lys Ser Ser Asn Gln Gln Ile Ala Ser Gly Gln Arg
                515                 520                 525

Asp Tyr Lys Asp Leu Asp Ala Arg Ile Leu Gln Phe Ile Phe Asp Arg
530                 535                 540

Val Lys Ala Ser Asp Glu Leu Leu Leu Asn Glu Ile Tyr Phe Gln Ala
545                 550                 555                 560

Lys Lys Leu Lys Gln Lys Ala Ser Ser Glu Leu Glu Lys Leu Glu Ser
                565                 570                 575

Ser Lys Lys Leu Asp Glu Val Ile Ala Asn Ser Gln Leu Ser Gln Ile
                580                 585                 590

Leu Lys Ser Gln His Thr Asn Gly Ile Phe Glu Gln Gly Thr Phe Leu
                595                 600                 605

His Leu Val Cys Lys Tyr Tyr Lys Gln Arg Gln Arg Ala Arg Asp Ser
        610                 615                 620

Arg Leu Tyr Ile Met Pro Glu Tyr Arg Tyr Asp Lys Lys Leu His Lys
625                 630                 635                 640

Tyr Asn Asn Thr Gly Arg Phe Asp Asp Asp Asn Gln Leu Leu Thr Tyr
                645                 650                 655

Cys Asn His Lys Pro Arg Gln Lys Arg Tyr Gln Leu Leu Asn Asp Leu
                660                 665                 670

Ala Gly Val Leu Gln Val Ser Pro Asn Phe Leu Lys Asp Lys Ile Gly
                675                 680                 685

Ser Asp Asp Asp Leu Phe Ile Ser Lys Trp Leu Val Glu His Ile Arg
690                 695                 700

Gly Phe Lys Lys Ala Cys Glu Asp Ser Leu Lys Ile Gln Lys Asp Asn
705                 710                 715                 720

Arg Gly Leu Leu Asn His Lys Ile Asn Ile Ala Arg Asn Thr Lys Gly
                725                 730                 735

Lys Cys Glu Lys Glu Ile Phe Asn Leu Ile Cys Lys Ile Glu Gly Ser
                740                 745                 750

Glu Asp Lys Lys Gly Asn Tyr Lys His Gly Leu Ala Tyr Glu Leu Gly
                755                 760                 765

Val Leu Leu Phe Gly Glu Pro Asn Glu Ala Ser Lys Pro Glu Phe Asp
770                 775                 780
```

-continued

Arg Lys Ile Lys Lys Phe Asn Ser Ile Tyr Ser Phe Ala Gln Ile Gln
785             790                 795                 800

Gln Ile Ala Phe Ala Glu Arg Lys Gly Asn Ala Asn Thr Cys Ala Val
            805                 810                 815

Cys Ser Ala Asp Asn Ala His Arg Met Gln Gln Ile Lys Ile Thr Glu
        820                 825                 830

Pro Val Glu Asp Asn Lys Asp Lys Ile Ile Leu Ser Ala Lys Ala Gln
            835                 840                 845

Arg Leu Pro Ala Ile Pro Thr Arg Ile Val Asp Gly Ala Val Lys Lys
        850                 855                 860

Met Ala Thr Ile Leu Ala Lys Asn Ile Val Asp Asp Asn Trp Gln Asn
865             870                 875                 880

Ile Lys Gln Val Leu Ser Ala Lys His Gln Leu His Ile Pro Ile Ile
                885                 890                 895

Thr Glu Ser Asn Ala Phe Glu Phe Glu Pro Ala Leu Ala Asp Val Lys
            900                 905                 910

Gly Lys Ser Leu Lys Asp Arg Lys Lys Ala Leu Glu Arg Ile Ser
        915                 920                 925

Pro Glu Asn Ile Phe Lys Asp Lys Asn Arg Ile Lys Glu Phe Ala
930             935                 940

Lys Gly Ile Ser Ala Tyr Ser Gly Ala Asn Leu Thr Asp Gly Asp Phe
945             950                 955                 960

Asp Gly Ala Lys Glu Glu Leu Asp His Ile Ile Pro Arg Ser His Lys
            965                 970                 975

Lys Tyr Gly Thr Leu Asn Asp Glu Ala Asn Leu Ile Cys Val Thr Arg
        980                 985                 990

Gly Asp Asn Lys Asn Lys Gly Asn Arg Ile Phe Cys Leu Arg Asp Leu
        995                 1000                1005

Ala Asp Asn Tyr Lys Leu Lys Gln Phe Glu Thr Thr Asp Asp Leu
    1010                1015                1020

Glu Ile Glu Lys Lys Ile Ala Asp Thr Ile Trp Asp Ala Asn Lys
    1025                1030                1035

Lys Asp Phe Lys Phe Gly Asn Tyr Arg Ser Phe Ile Asn Leu Thr
    1040                1045                1050

Pro Gln Glu Gln Lys Ala Phe Arg His Ala Leu Phe Leu Ala Asp
    1055                1060                1065

Glu Asn Pro Ile Lys Gln Ala Val Ile Arg Ala Ile Asn Asn Arg
    1070                1075                1080

Asn Arg Thr Phe Val Asn Gly Thr Gln Arg Tyr Phe Ala Glu Val
    1085                1090                1095

Leu Ala Asn Asn Ile Tyr Leu Arg Ala Lys Lys Glu Asn Leu Asn
    1100                1105                1110

Thr Asp Lys Ile Ser Phe Asp Tyr Phe Gly Ile Pro Thr Ile Gly
    1115                1120                1125

Asn Gly Arg Gly Ile Ala Glu Ile Arg Gln Leu Tyr Glu Lys Val
    1130                1135                1140

Asp Ser Asp Ile Gln Ala Tyr Ala Lys Gly Asp Lys Pro Gln Ala
    1145                1150                1155

Ser Tyr Ser His Leu Ile Asp Ala Met Leu Ala Phe Cys Ile Ala
    1160                1165                1170

Ala Asp Glu His Arg Asn Asp Gly Ser Ile Gly Leu Glu Ile Asp
    1175                1180                1185

-continued

```
Lys Asn Tyr Ser Leu Tyr Pro Leu Asp Lys Asn Thr Gly Glu Val
1190             1195             1200

Phe Thr Lys Asp Ile Phe Ser Gln Ile Lys Ile Thr Asp Asn Glu
1205             1210             1215

Phe Ser Asp Lys Lys Leu Val Arg Lys Lys Ala Ile Glu Gly Phe
1220             1225             1230

Asn Thr His Arg Gln Met Thr Arg Asp Gly Ile Tyr Ala Glu Asn
1235             1240             1245

Tyr Leu Pro Ile Leu Ile His Lys Glu Leu Asn Glu Val Arg Lys
1250             1255             1260

Gly Tyr Thr Trp Lys Asn Ser Glu Glu Ile Lys Ile Phe Lys Gly
1265             1270             1275

Lys Lys Tyr Asp Ile Gln Gln Leu Asn Asn Leu Val Tyr Cys Leu
1280             1285             1290

Lys Phe Val Asp Lys Pro Ile Ser Ile Asp Ile Gln Ile Ser Thr
1295             1300             1305

Leu Glu Glu Leu Arg Asn Ile Leu Thr Thr Asn Asn Ile Ala Ala
1310             1315             1320

Thr Ala Glu Tyr Tyr Ile Asn Leu Lys Thr Gln Lys Leu His
1325             1330             1335

Glu Tyr Tyr Ile Glu Asn Tyr Asn Thr Ala Leu Gly Tyr Lys Lys
1340             1345             1350

Tyr Ser Lys Glu Met Glu Phe Leu Arg Ser Leu Ala Tyr Arg Ser
1355             1360             1365

Glu Arg Val Lys Ile Lys Ser Ile Asp Asp Val Lys Gln Val Leu
1370             1375             1380

Asp Lys Asp Ser Asn Phe Ile Ile Gly Lys Ile Thr Leu Pro Phe
1385             1390             1395

Lys Lys Glu Trp Gln Arg Leu Tyr Arg Glu Trp Gln Asn Thr Thr
1400             1405             1410

Ile Lys Asp Asp Tyr Glu Phe Leu Lys Ser Phe Phe Asn Val Lys
1415             1420             1425

Ser Ile Thr Lys Leu His Lys Lys Val Arg Lys Asp Phe Ser Leu
1430             1435             1440

Pro Ile Ser Thr Asn Glu Gly Lys Phe Leu Val Lys Arg Lys Thr
1445             1450             1455

Trp Asp Asn Asn Phe Ile Tyr Gln Ile Leu Asn Asp Ser Asp Ser
1460             1465             1470

Arg Ala Asp Gly Thr Lys Pro Phe Ile Pro Ala Phe Asp Ile Ser
1475             1480             1485

Lys Asn Glu Ile Val Glu Ala Ile Ile Asp Ser Phe Thr Ser Lys
1490             1495             1500

Asn Ile Phe Trp Leu Pro Lys Asn Ile Glu Leu Gln Lys Val Asp
1505             1510             1515

Asn Lys Asn Ile Phe Ala Ile Asp Thr Ser Lys Trp Phe Glu Val
1520             1525             1530

Glu Thr Pro Ser Asp Leu Arg Asp Ile Gly Ile Ala Thr Ile Gln
1535             1540             1545

Tyr Lys Ile Asp Asn Asn Ser Arg Pro Lys Val Arg Val Lys Leu
1550             1555             1560

Asp Tyr Val Ile Asp Asp Asp Ser Lys Ile Asn Tyr Phe Met Asn
1565             1570             1575

His Ser Leu Leu Lys Ser Arg Tyr Pro Asp Lys Val Leu Glu Ile
```

```
                    1580              1585              1590
Leu Lys Gln Ser Thr Ile Ile Glu Phe Glu Ser Ser Gly Phe Asn
        1595              1600              1605

Lys Thr Ile Lys Glu Met Leu Gly Met Lys Leu Ala Gly Ile Tyr
    1610              1615              1620

Asn Glu Thr Ser Asn Asn
        1625

<210> SEQ ID NO 2
<211> LENGTH: 4890
<212> TYPE: DNA
<213> ORGANISM: Artificial Sequence
<220> FEATURE:
<223> OTHER INFORMATION: synthetic construct

<400> SEQUENCE: 2
atgaatttca aaatattgcc aatagcaata gatttaggtg ttaaaaatac tggtgtcttt      60
agcgcatttt atcaaaaagg aacttctctt gagagattgg ataataaaaa tggcaaagta     120
tatgaactat caaagattc ttatacttta ttgatgaata atagaacagc aagaagacat      180
caaagaagag ggatagatag aaagcagcta gtcaaaaggc tctttaagct tatttggaca     240
gagcagctaa atttagagtg ggataaagac actcaacaag caattagctt tttatttaat     300
cgtagaggtt ttagttttat tactgatggt tattcgcctg aatatttaaa tattgttcca     360
gagcaagtaa aagcgatact tatggatata tttgatgatt acaacggtga agatgattta     420
gacagttatt taaaattagc tactgagcaa gaaagcaaaa tttctgaaat ttataacaag     480
ctaatgcaaa aatattaga gtttaaatta atgaaattat gtactgatat taaggatgat     540
aaagtaagta ctaaaacgct taagaaatc acaagctatg aatttgagtt attagctgat     600
tatttagcaa actatagcga gagtttaaaa acacaaaaat ttagttatac agataaacaa     660
ggtaatttaa aagagctaag ctactatcat catgataaat ataatattca agaatttcta     720
aagcgacatg ctactataaa tgatcgaatt ttagatactc ttttaactga tgatttagat     780
atttggaatt taattttga aaatttgat tttgataaga tgaagaaaa gcttcagaat       840 caggaagata aagatcatat acaagcgcat ttacatcatt ttgttttgc agtaaataaa      900 ataaaaagtg aaatggcaag tggtggtcgt catcgtagcc aatattttca agagataaca     960
aatgtgctag atgaaaataa tcatcaagag ggatatctca agaatttctg tgaaaatttg    1020
cataataaaa aatattccaaa tttaagtgtt aaaaatttag ttaatctaat tggtaaccta    1080
agtaatttag agctaaaacc gctaagaaaa tatttaatg acaaaattca cgcaaaagct     1140
gatcattggg atgagcaaaa gtttacagaa acttattgcc actggatatt aggagagtgg    1200
cgagtaggtg tcaaagatca agataagaaa gatggcgcta atatagttaa aagatctg     1260 tgtaatgaat aaaacaaaa agttactaag gctggtttgg tagattttt attagagtta     1320 gatccatgta aactataccc accatatctg ataacaata accgtaaacc accaaaatgt     1380
caaagtttga ttttaaatcc gaagttttta gataatcaat atccaaactg gcaacaatat    1440
ttacaagaat taagaaaact acaaagtatt caaaattatt tagacagttt tgaaactgat    1500
ttaaaagtct taaagtcaag taagatcaa ccatatttg ttgaatacaa gagttcaaat     1560
cagcaaatag caagtggtca aagagattat aaagattag atgctcgaat attacagttt    1620
atatttgata gggtaaaagc tagtgatgag ttgcttttga atgagattta ttttcaggct    1680
aaaaaactta acaaaaagc tagctctgag ttagaaaaac tcgagtcgag caaaaagcta    1740
```

```
gatgaagtta tagcaaatag tcaactatca cagatactaa agtctcaaca tacaaatggt    1800
atttttgaac agggtacttt tttgcatttg gtttgtaaat attataaaca aagacaaaga    1860
gcgagagact ctaggctata tattatgcct gaatatcgtt atgataaaaa actacataaa    1920
tataacaata caggcaggtt tgatgatgat aatcagctgc taacatattg taatcataag    1980
ccaagacaaa aaagatacca attgttaaat gatttagctg gggtgttgca ggtatcacct    2040
aattttttga agataaaat tggttctgat gatgatctat ttattagcaa atggttggta    2100
gagcatatta gaggatttaa aaaagcttgt gaagatagtt taaaaataca aaagacaat    2160 agaggattat taaatcataa aataaatata gctaggaata caaaaggcaa atgtgaaaaa    2220
gaaatattta atttaatatg taaaatagaa ggttcagaag ataaaaaagg taattacaag    2280
catggtttag cttacgaatt aggagtactt ttatttggtg aacctaatga agctagtaaa    2340
cctgagttcg atagaaaaat taaaaaattt aactcaatat acagttttgc acagattcaa    2400
caaattgctt ttgcagagcg taaaggcaat gctaacactt gtgcagtttg tagtgctgat    2460
aatgctcata gaatgcaaca aattaagatc actgagcctg tagaggacaa taagataag    2520 ataatcttaa gtgccaaagc tcagagacta ccagcgattc caactagaat agttgacggt    2580
gcggttaaga aaatggcaac tatattagct aaaaatatag ttgatgataa ttggcagaat    2640
atcaaacaag ttttatcagc aaaacatcag ttacatatac ctattatcac agaatcaaat    2700
gcttttgagt ttgaaccagc attagctgat gtaaaaggta agagcctaaa agataggaga    2760
aaaaaagcat tagagagaat aagtcctgaa aatatattca aggataaaaa caatagaata    2820
aaagaatttg ctaaaggtat atcagcatat agtggtgcta atttaactga tggcgatttt    2880
gatggtgcaa aagaagaatt agatcatata atacctcgtt cacataaaaa atacggtact    2940
ctaaatgatg aagcaaatct aatttgtgta actcgtggtg ataataaaaa taaggtaat    3000 agaattttct gcctacgtga tcttgcagat aactataaac taaaacagtt tgagacaact    3060
gatgatttag aaattgaaaa gaagatagct gatacaatct gggatgctaa caagaaagat    3120
tttaaatttg gtaattatcg tagttttatt aacctaacac cacaagagca gaaagcattt    3180
cgtcacgcgc tatttctggc tgatgaaaat cctatcaaac aagcagtcat aagagcgata    3240
aataatcgta atcgtacatt tgtaaatggc actcaacgct attttgcaga agtactggca    3300
aacaatatct atctaagggc taaaaaagaa atctaaaata cagataaaat ttcatttgat    3360
tattttggta ttccaactat aggtaatggt agaggtattg ctgaaatccg tcaactttat    3420
gaaaaagttg atagtgatat acaagcttat gcaaaaggtg ataaacctca agctagctac    3480
tctcacctaa tagatgcgat gctggctttt tgtattgctg ctgatgaaca cagaaatgat    3540
ggaagtatag gtctagaaat cgataaaaat tatagtttat atccattaga taaaaataca    3600
ggagaagtct ttaccaaaga tatttttagt caaattaaaa ttactgataa tgagtttagc    3660
gataaaaaat tagtaagaaa aaagctata gagggcttta cacgcatag acaaatgact    3720 agagatggca tttatgcaga aaattaccta ccaatactaa tccataaaga actaaatgaa    3780
gttagaaaag gctatacttg gaaaatagt gaagaaataa aatattcaa aggtaaaaag    3840 tacgatatac aacaattgaa taaccttgtg tattgtctaa aatttgtaga taaacctata    3900
tctatagata tacaaattag taccttagaa gagttaagaa atatattaac aacaaataat    3960
atagctgcta cagcagaata ctattatata atctaaaaa cccaaaaatt acatgagtat    4020
tatatcgaaa actataatac tgccttaggt tataaaaat acagtaaaga aatggagttt    4080
ttgagaagct tagcttatcg tagcgaaagg gtaaaaatta aatcaataga tgatgtaaag    4140
```

```
caggttttgg ataaggatag taactttatc atcggtaaga ttactttacc atttaaaaaa    4200
gagtggcaaa gactatatcg tgagtggcaa aatacaacta tcaaagatga ttatgagttt    4260
ttaaaatcat tctttaatgt taaaagtatt actaagttgc ataaaaagt tagaaaagat     4320 ttctctttac ctatttctac aaatgaaggt aaattcctgg tcaaaagaaa acatgggat     4380 aacaatttta tctatcagat attaaatgat tctgattcta gagcagacgg aacaaagcca    4440
tttattccag cttttgacat ttctaaaaat gaaatagtcg aagccataat tgattcattt    4500
acatcaaaaa atattttttg gctgcctaaa aatatagaat tacaaaaggt ggataataaa    4560
aacatttttg ctatagatac tagtaaatgg ttcgaagtag aaacacctag tgatcttaga    4620
gacattggaa tagcaacaat tcaatacaag atagataata attctcgccc taaagtcaga    4680
gttaaacttg attatgttat cgatgatgat agtaagataa attattttat gaatcattct    4740
ttattaaaat caagatatcc tgacaaagtt ttagaaattt taaaacaatc aactattata    4800
gaatttgaaa gttcaggttt taataaaact atcaaagaaa tgcttggtat gaaattagca    4860
ggtatttata atgaaacatc taataattag                                     4890

<210> SEQ ID NO 3
<211> LENGTH: 76
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: where n is any nucleotide.
<220> FEATURE:
<221> NAME/KEY: misc_feature
<222> LOCATION: (45)..(46)
<223> OTHER INFORMATION: where n is any nucleotide.

<400> SEQUENCE: 3
guuguuagau uauuuggu au guacuugugu uaguuuaaag uagcuagaaa auucacuuuu    60
agaccuacuu auuuuu                                                    76

<210> SEQ ID NO 4
<211> LENGTH: 111
<212> TYPE: RNA
<213> ORGANISM: Artificial Sequence
<220> FEATURE:
<223> OTHER INFORMATION: synthetic construct

<400> SEQUENCE: 4
guaccaaaua auuaaugcuc uguaaucauu uaaaaguauu uugaacggac cucuguuuga    60
cacgucugaa uaacuaaaaa gcaaaaauuu gccaccuaag uggcuuuuuu u             111

<210> SEQ ID NO 5
<211> LENGTH: 13
<212> TYPE: RNA
<213> ORGANISM: Artificial Sequence
<220> FEATURE:
<223> OTHER INFORMATION: Synthetic construct

<400> SEQUENCE: 5
guaccaaaua auu                                                       13

<210> SEQ ID NO 6
<211> LENGTH: 21
<212> TYPE: PRT
```

<213> ORGANISM: Artificial Sequence
<220> FEATURE:
<223> OTHER INFORMATION: Synthetic construct

<400> SEQUENCE: 6

```
Met Asn Asn Arg Thr Ala Arg Arg His Gln Arg Arg Gly Ile Asp Arg
1               5                   10                  15
Lys Gln Leu Val Lys
            20
```

<210> SEQ ID NO 7
<211> LENGTH: 35
<212> TYPE: PRT
<213> ORGANISM: Artificial Sequence
<220> FEATURE:
<223> OTHER INFORMATION: Synthetic construct

<400> SEQUENCE: 7

```
Lys Asn Ile Val Asp Asp Asn Trp Gln Asn Ile Lys Gln Val Leu Ser
1               5                   10                  15
Ala Lys His Gln Leu His Ile Pro Ile Ile Thr Glu Ser Asn Ala Phe
            20                  25                  30
Glu Phe Glu
        35
```

<210> SEQ ID NO 8
<211> LENGTH: 31
<212> TYPE: PRT
<213> ORGANISM: Artificial Sequence
<220> FEATURE:
<223> OTHER INFORMATION: Synthetic construct

<400> SEQUENCE: 8

```
Ala Lys Gly Asp Lys Pro Gln Ala Ser Tyr Ser His Leu Ile Asp Ala
1               5                   10                  15
Met Leu Ala Phe Cys Ile Ala Ala Asp Glu His Arg Asn Asp Gly
            20                  25                  30
```

<210> SEQ ID NO 9
<211> LENGTH: 4887
<212> TYPE: DNA
<213> ORGANISM: Homo sapiens

<400> SEQUENCE: 9

```
atgaacttta agatcctccc tattgccatc gacctgggcg tgaagaacac cggcgtgttt      60
agcgcctttt accagaaggg caccagcctg gagagactgg ataataagaa cggcaaggtg     120
tatgagctca gcaaggacag ctatacactg ctcatgaata acaggaccgc tagaaggcac     180
caaagaagag gcatcgacag aaagcagctg gtcaagagac tgttcaaact gatttggaca     240
gagcaactga acctggagtg ggataaggac cccagcagg ctatctcctt cctcttcaac     300
aggagaggct tcagcttcat taccgacggc tactccctg agtatctgaa cattgtcccc     360
gaacaggtca aggccatcct gatggacatc tttgacgact acaacggaga ggatgatctc     420
gactcctatc tgaagctggc taccgaacag gaaagcaaga tttccgagat ctacaacaag     480
ctcatgcaaa agattctgga attcaagctc atgaagctgt gtaccgatat caggacgac     540 aaggtcagca ccaaaaccct caaagaaatc accagctatg aatttgagct gctggccgat     600
tacctggcta attacagcga gagcctgaag acccagaagt tcagctatac cgataagcaa     660
ggcaatctca aggagctgag ctactatcac atgacaagt acaatattca ggagtttctg     720
```

```
aagaggcatg ctaccatcaa tgataggatc ctcgacacac tgctcaccga tgacctggat    780
atctggaact ttaactttga gaaattcgac tttgataaga atgaagaaaa gctgcaaaat    840
caggaagaca aggatcacat tcaggctcac ctgcaccact tcgtcttcgc cgtcaacaag    900
atcaagagcg aaatggcttc cggaggcagg cacaggagcc agtacttcca ggaaatcacc    960
aacgtcctgg acgagaacaa ccaccaggaa ggctacctca agaatttctg tgagaacctg   1020
cacaacaaga aatatagcaa cctgtccgtg aaaaacctcg tcaacctcat cggcaacctg   1080
agcaatctgg agctgaagcc cctgaggaag tacttcaacg acaagattca tgccaaggct   1140
gaccactggg acgagcagaa gttcacagag acatactgtc actggatcct gggagaatgg   1200
agggtgggcg tcaaagacca ggacaaaaaa gatggagcta agtacagcta caaagatctg   1260
tgtaatgagc tcaaacagaa ggtgacaaaa gccggactgg tggacttcct gctggagctg   1320
gatccctgca ggacaattcc ccctatctc gacaacaata acaggaagcc tcccaagtgc   1380
caaagcctca tcctcaaccc caagttcctc gacaatcagt atcccaattg gcagcagtac   1440
ctgcaagaac tgaaaaaact gcaaagcatt caaaactacc tcgattcctt cgagaccgac   1500
ctcaaagtcc tcaaaagcag caaggaccaa ccctacttcg tcaatacaa gagcagcaac   1560 cagcagatcg cctccggaca gagagactac aaagacctcg acgccaggat tctgcaattc   1620
atcttcgaca gagtcaaggc ttccgacgaa ctgctgctga tgaaatcta ttttcaagct   1680 aaaaagctca agcagaaagc cagcagcgaa ctcgaaaaac tggagtcctc caagaaactc   1740
gacgaggtga ttgccaatag ccaactcagc cagatcctga agagccagca tacaaatggc   1800
atcttcgagc aaggcacatt tctgcatctg gtgtgtaaat actacaaaca aagacagagg   1860
gctagggaca gcagactcta tatcatgccc gagtacagat acgataaaaa actgcataaa   1920
tacaacaaca ccggcaggtt tgacgacgat aaccaactgc tcacctactg caaccacaag   1980
cctaggcaaa aaaggtatca gctgctgaac gacctggctg gagtgctcca agtctcccct   2040
aatttcctca aggataaaat tggatccgac gatgacctct tcatctccaa gtggctggtc   2100
gagcacatca gaggcttcaa gaaggcctgc gaagattccc tgaaaatcca gaaggacaac   2160
aggggactcc tgaatcataa gattaatatc gctagaaata ccaagggcaa atgcgagaag   2220
gagatcttca acctgatctg caaaatcgaa ggctccgagg ataagaaagg caactataag   2280
catggcctgg cttatgagct cggagtgctc ctgttcggag agcccaatga ggcctccaag   2340
cctgaatttg acaggaagat caagaagttt aatagcatct actccttcgc ccagatccaa   2400
caaatcgcct tcgctgaaag gaagggcaac gctaacacct cgccgtgtgt cagcgctgat   2460
aatgctcaca ggatgcagca gatcaagatc acagaacccg tggaagacaa taaagacaag   2520
atcatcctca gcgctaaggc tcagagactg cccgctattc ctacaagaat cgtgacggga   2580
gccgtcaaga aaatggccac catcctggcc aaaaacatcg tggatgataa ttggcaaaat   2640
attaaacagg tcctgtccgc caagcaccag ctccacattc ccatcatcac cgagtccaat   2700
gctttcgagt tcgaacccgc cctggctgac gtgaaaggca atccctcaa ggacagaaga   2760 aagaaggccc tggagagaat tcccctgag aacatcttta aggacaaaaa taacagaatt   2820
aaagagtttg ctaagggaat ttccgcctac agcggcgcca atctgacaga tggcgacttc   2880
gatggcgcta agaagagct cgaccacatc attcccagaa gccacaagaa gtatggaacc   2940
ctcaacgatg aggccaacct catctgcgtc accaggggcg acaataaaaa taaaggcaat   3000
aggatcttct gtctgagaga cctggccgat aactacaaac tgaaacagtt cgaaaccacc   3060
gacgacctgg agattgagaa gaaaatcgcc gacaccatct gggacgctaa taaaaagac   3120
```

-continued

```
tttaagttcg gaaactacag gagcttcatt aacctgacac cccaggaaca gaaagccttt    3180
aggcatgccc tctttctggc cgatgagaac cctatcaagc aagccgtcat cagggccatc    3240
aacaacagga ataggacctt cgtcaatggc acccagaggt actttgccga ggtgctggcc    3300
aataacatct atctcagggc taaaaaggag aatctcaata cagacaaaat ctcctttgac    3360
tattttggaa tccctaccat cggaaatggc aggggaatcg ctgagattag acagctgtac    3420
gagaaagtcg acagcgatat ccaagcctac gccaagggag ataagcctca ggcttcctat    3480
agccacctca tcgacgctat gctggccttt tgcatcgccg ccgacgagca cagaaatgat    3540
ggctccatcg gactggaaat cgacaagaat tacagcctct accccctcga caaaaacaca    3600
ggagaggtgt tcacaaaaga tattttcagc cagattaaga ttacagacaa cgaatttagc    3660
gataagaaac tggtgagaaa gaaagctatc gagggattta atacccatag caaatgacc     3720 agggacggca tttacgctga gaactatctc cccatcctca tccacaagga actgaacgaa    3780
gtcagaaaag gatatacctg gaaaaatagc gaggaaatta gattttcaa aggaaaaaag    3840 tatgacatcc agcagctcaa caacctcgtg tattgcctca gttcgtggaa caagcccatt    3900
tccatcgaca tccagatcag cacactggaa gagctgagga atatcctgac cacaaataac    3960
attgccgcta ccgctgagta ttattacatt aatctcaaaa cacagaaact gcatgaatat    4020
tacatcgaga actacaatac cgccctgggc tataagaagt attccaagga aatggagttc    4080
ctcaggtccc tcgcctatag gagcgagagg gtgaagatta agagcatcga cgatgtcaag    4140
caggtgctgg acaaggatag caacttcatt attggaaaaa tcacactccc ctttaagaag    4200
gagtggcaga ggctgtacag ggagtggcaa aacaccacaa tcaaggacga ttacgagttc    4260
ctgaagagct tctttaacgt gaagagcatt acaaagctgc acaagaaggt caggaaagac    4320
ttcagcctcc ccattagcac aacgaggga aagttcctgg tgaagaggaa gacctgggac    4380
aacaacttca tctaccagat cctcaatgac tccgacagca gggccgacgg cacaaagccc    4440
tttatccctg ccttcgacat cagcaagaac gaaatcgtgg aggccatcat cgattccttt    4500
accagcaaaa acattttctg gctgcccaaa aatattgaac tccagaaggt cgacaacaaa    4560
aacatctttg ctatcgacac atccaaatgg tttgaagtcg agacaccttc cgacctgagg    4620
gatatcggaa ttgccaccat tcaatataag atcgacaata atagcaggcc taaagtgagg    4680
gtcaaactcg actacgtgat cgacgacgac agcaagatca actacttcat gaaccacagc    4740
ctgctgaagt ccaggtatcc cgacaaggtc ctcgaaatcc tcaagcagag caccatcatt    4800
gaatttgagt ccagcggatt caacaagaca atcaaagaga tgctgggcat gaaactcgcc    4860
ggcatctata acgagaccag caataac                                       4887
```

<210> SEQ ID NO 10
<211> LENGTH: 63
<212> TYPE: RNA
<213> ORGANISM: Homo sapiens

<400> SEQUENCE: 10

```
uaucaggcag uaccacaagc ucguaauuaa uaaaccauga aaguaugguu uauuagauug    60
uug                                                                 63
```

<210> SEQ ID NO 11
<211> LENGTH: 44
<212> TYPE: RNA
<213> ORGANISM: Homo sapiens -continued

```
<400> SEQUENCE: 11
cucguaauua auaaaccaug aaaguauggu uuauuagauu guug          44

<210> SEQ ID NO 12
<211> LENGTH: 87
<212> TYPE: RNA
<213> ORGANISM: Homo sapiens

<400> SEQUENCE: 12
guaucaggca guaccacaag cucguaauua auaaaccaug aaaguauggu uuauuagauu   60
guugaaggcu aguccguuau caacuug                                      87

<210> SEQ ID NO 13
<211> LENGTH: 46
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: where n is any nucleotide
<220> FEATURE:
<221> NAME/KEY: misc_feature
<222> LOCATION: (46)..(46)
<223> OTHER INFORMATION: where n is any nucleotide

<400> SEQUENCE: 13
ncucguaauu aauaaaccau gaaaguaugg uuuauuagau uguugn          46

<210> SEQ ID NO 14
<211> LENGTH: 14
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (14)..(14)
<223> OTHER INFORMATION: where n is any nucleaotide

<400> SEQUENCE: 14
guaccaaaua auun                                           14

<210> SEQ ID NO 15
<211> LENGTH: 16
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (9)..(13)
<223> OTHER INFORMATION: n is a, c, g, or u

<400> SEQUENCE: 15
aaauaugann nnnggu                                         16

<210> SEQ ID NO 16
<211> LENGTH: 111
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(47)
<223> OTHER INFORMATION: n is a, c, g, or u
```

```
<220> FEATURE:
<221> NAME/KEY: misc_feature
<222> LOCATION: (59)..(111)
<223> OTHER INFORMATION: n is a, c, g, or u

<400> SEQUENCE: 16
guaccaaaua auuaaugcuc unnnnnnnnn nnnnnnnnnn nnnnnnngac cucuguuunn      60
nnnnnnnnnn nnnnnnnnnn nnnnnnnnnn nnnnnnnnnn nnnnnnnnnn n             111

<210> SEQ ID NO 17
<211> LENGTH: 20
<212> TYPE: RNA
<213> ORGANISM: Artificial Sequence
<220> FEATURE:
<223> OTHER INFORMATION: synthetic construct

<400> SEQUENCE: 17
guuguuagau uauuugguau                                                  20

<210> SEQ ID NO 18
<211> LENGTH: 36
<212> TYPE: PRT
<213> ORGANISM: Streptococcus pyogenes

<400> SEQUENCE: 18

Thr Ala Glu Ala Thr Arg Leu Lys Arg Thr Ala Arg Arg Arg Tyr Thr
1               5                   10                  15

Arg Arg Lys Asn Arg Ile Cys Tyr Leu Gln Glu Ile Phe Ser Asn Glu
                20                  25                  30

Met Ala Lys Val
        35

<210> SEQ ID NO 19
<211> LENGTH: 36
<212> TYPE: PRT
<213> ORGANISM: Listeria monocytogenes

<400> SEQUENCE: 19

Thr Ala Ala Asp Arg Arg Met Asn Arg Thr Ala Arg Arg Arg Ile Glu
1               5                   10                  15

Arg Arg Arg Asn Arg Ile Ser Tyr Leu Gln Glu Ile Phe Ala Leu Glu
                20                  25                  30

Met Ala Asn Ile
        35

<210> SEQ ID NO 20
<211> LENGTH: 36
<212> TYPE: PRT
<213> ORGANISM: Lactobacillus salivarius

<400> SEQUENCE: 20

Thr Ala Ala Glu Arg Arg Gly Phe Arg Thr Gln Arg Arg Arg Leu Asn
1               5                   10                  15

Arg Arg Lys Trp Arg Leu Lys Leu Leu Glu Glu Ile Phe Asp Pro Tyr
                20                  25                  30

Met Ala Glu Val
        35

<210> SEQ ID NO 21
<211> LENGTH: 36
<212> TYPE: PRT
<213> ORGANISM: Neisseria meningitidis
```

<400> SEQUENCE: 21

Leu Ala Met Ala Arg Arg Leu Ala Arg Ser Val Arg Arg Leu Thr Arg
1               5                   10                  15

Arg Arg Ala His Arg Leu Leu Arg Ala Arg Arg Leu Leu Lys Arg Glu
                20                  25                  30

Gly Val Leu Gln
        35

<210> SEQ ID NO 22
<211> LENGTH: 31
<212> TYPE: PRT
<213> ORGANISM: Legionella pneumophilia

<400> SEQUENCE: 22

Leu Ser Gln Ala Gln Arg Arg Ala Thr Arg His Arg Val Arg Asn Lys
1               5                   10                  15

Lys Arg Asn Gln Phe Val Lys Arg Val Ala Leu Gln Leu Phe Gln
                20                  25                  30

<210> SEQ ID NO 23
<211> LENGTH: 35
<212> TYPE: PRT
<213> ORGANISM: Burkholderiales spp.

<400> SEQUENCE: 23

Phe Ser Ser Lys Ser Arg Thr Ala Val Arg His Arg Val Arg Ser Tyr
1               5                   10                  15

Lys Gly Phe Asp Leu Arg Arg Arg Leu Leu Leu Leu Val Ala Glu Tyr
            20                  25                  30

Gln Leu Leu
        35

<210> SEQ ID NO 24
<211> LENGTH: 36
<212> TYPE: PRT
<213> ORGANISM: Campylobacter jejuni

<400> SEQUENCE: 24

Leu Ala Leu Pro Arg Arg Leu Ala Arg Ser Ala Arg Lys Arg Leu Ala
1               5                   10                  15

Arg Arg Lys Ala Arg Leu Asn His Leu Lys His Leu Ile Ala Asn Glu
            20                  25                  30

Phe Lys Leu Asn
        35

<210> SEQ ID NO 25
<211> LENGTH: 33
<212> TYPE: PRT
<213> ORGANISM: Francisella novicida

<400> SEQUENCE: 25

Leu Leu Met Asn Asn Arg Thr Ala Arg Arg His Gln Arg Arg Gly Ile
1               5                   10                  15

Asp Arg Lys Gln Leu Val Lys Arg Leu Phe Lys Leu Ile Trp Thr Glu
            20                  25                  30

Gln

<210> SEQ ID NO 26
<211> LENGTH: 35

```
<212> TYPE: PRT
<213> ORGANISM: Streptococcus pyogenes

<400> SEQUENCE: 26

Val Met Gly Arg His Lys Pro Glu Asn Ile Val Ile Glu Met Ala Arg
1               5                   10                  15

Glu Asn Gln Thr Thr Gln Lys Gly Gln Lys Asn Ser Arg Glu Arg Met
            20                  25                  30

Lys Arg Ile
        35

<210> SEQ ID NO 27
<211> LENGTH: 34
<212> TYPE: PRT
<213> ORGANISM: Listeria monocytogenes

<400> SEQUENCE: 27

Ile Met Gly Tyr Pro Pro Gln Thr Ile Val Val Glu Met Ala Arg Glu
1               5                   10                  15

Asn Gln Thr Thr Val Lys Gly Lys Asn Asn Ser Arg Pro Arg Tyr Lys
            20                  25                  30

Ser Leu

<210> SEQ ID NO 28
<211> LENGTH: 30
<212> TYPE: PRT
<213> ORGANISM: Lactobacillus salivarius

<400> SEQUENCE: 28

Ala Met Lys Cys Glu Pro Thr Ser Ile Ala Ile Glu Phe Thr Arg Glu
1               5                   10                  15

Lys Arg Lys Ser Lys Leu Thr Asn Thr Arg Tyr Lys Lys Ile
            20                  25                  30

<210> SEQ ID NO 29
<211> LENGTH: 37
<212> TYPE: PRT
<213> ORGANISM: Neisseria meningitidis

<400> SEQUENCE: 29

Arg Tyr Gly Ser Pro Ala Arg Ile His Ile Glu Thr Ala Arg Glu Val
1               5                   10                  15

Gly Lys Ser Phe Lys Asp Arg Lys Glu Ile Glu Lys Arg Gln Glu Glu
            20                  25                  30

Asn Arg Lys Asp Arg
        35

<210> SEQ ID NO 30
<211> LENGTH: 40
<212> TYPE: PRT
<213> ORGANISM: Legionella pneumophilia

<400> SEQUENCE: 30

Arg Met Met Gln Arg Leu Ala Tyr Glu Ile Ala Met Ala Lys Trp Glu
1               5                   10                  15

Gln Ile Lys His Ile Pro Asp Asn Ser Ser Leu Leu Ile Pro Ile Tyr
            20                  25                  30

Leu Glu Gln Asn Arg Phe Glu Phe
        35                  40
```

```
<210> SEQ ID NO 31
<211> LENGTH: 42
<212> TYPE: PRT
<213> ORGANISM: Burkholderiales spp.

<400> SEQUENCE: 31
```

Lys Ala Ile Asp Arg Asn Ser Trp Glu Val Ala Lys Arg Ile Ala Glu
1               5                   10                  15

Glu Val Lys Lys Ser Val Asp Phe Thr Asn Gly Thr Val Lys Ile Pro
            20                  25                  30

Val Ala Ile Glu Ala Asn Ser Phe Asn Phe
        35                  40

```
<210> SEQ ID NO 32
<211> LENGTH: 37
<212> TYPE: PRT
<213> ORGANISM: Campylobacter jejuni

<400> SEQUENCE: 32
```

Lys Tyr Gly Lys Val His Lys Ile Asn Ile Glu Leu Ala Arg Glu Val
1               5                   10                  15

Gly Lys Asn His Ser Gln Arg Ala Lys Ile Glu Lys Glu Gln Asn Glu
            20                  25                  30

Asn Tyr Lys Ala Lys
        35

```
<210> SEQ ID NO 33
<211> LENGTH: 41
<212> TYPE: PRT
<213> ORGANISM: Francisella novicida

<400> SEQUENCE: 33
```

Lys Met Ala Thr Ile Leu Ala Lys Asn Ile Val Asp Asp Asn Trp Gln
1               5                   10                  15

Asn Ile Lys Gln Val Leu Ser Ala Lys His Gln Leu His Ile Pro Ile
            20                  25                  30

Ile Thr Glu Ser Asn Ala Phe Glu Phe
        35                  40

```
<210> SEQ ID NO 34
<211> LENGTH: 31
<212> TYPE: PRT
<213> ORGANISM: Streptococcus pyogenes

<400> SEQUENCE: 34
```

Phe Tyr Lys Val Arg Glu Ile Asn Asn Tyr His His Ala His Asp Ala
1               5                   10                  15

Tyr Leu Asn Ala Val Val Gly Thr Ala Leu Ile Lys Lys Tyr Pro
            20                  25                  30

```
<210> SEQ ID NO 35
<211> LENGTH: 31
<212> TYPE: PRT
<213> ORGANISM: Listeria monocytogenes

<400> SEQUENCE: 35
```

Leu Tyr Lys Val Arg Glu Val Asn Asp Tyr His His Ala His Asp Ala
1               5                   10                  15

Tyr Leu Asn Gly Val Val Ala Asn Thr Leu Leu Lys Val Tyr Pro
            20                  25                  30

```
<210> SEQ ID NO 36
<211> LENGTH: 31
<212> TYPE: PRT
<213> ORGANISM: Lactobacillus salivarius

<400> SEQUENCE: 36

Leu Ile Lys Asn Arg Glu Val Asn Asp Tyr His His Ala Ile Asp Gly
1               5                   10                  15

Tyr Leu Thr Thr Phe Val Gly Gln Tyr Leu Tyr Lys Val Tyr Pro
            20                  25                  30

<210> SEQ ID NO 37
<211> LENGTH: 31
<212> TYPE: PRT
<213> ORGANISM: Neisseria meningitidis

<400> SEQUENCE: 37

Leu Arg Lys Val Arg Ala Glu Asn Asp Arg His His Ala Leu Asp Ala
1               5                   10                  15

Val Val Val Ala Cys Ser Thr Val Ala Met Gln Gln Lys Ile Thr
            20                  25                  30

<210> SEQ ID NO 38
<211> LENGTH: 31
<212> TYPE: PRT
<213> ORGANISM: Legionella pneumophilia

<400> SEQUENCE: 38

Leu Val Lys Ser Arg Gln Gln Ser Phe Pro Ser His Ala Ile Asp Ala
1               5                   10                  15

Thr Leu Thr Met Ser Ile Gly Leu Lys Glu Phe Pro Gln Phe Ser
            20                  25                  30

<210> SEQ ID NO 39
<211> LENGTH: 30
<212> TYPE: PRT
<213> ORGANISM: Burkholderiales spp.

<400> SEQUENCE: 39

Phe Arg Lys Pro Lys Val Gln Pro Val Ala Ser His Ser Ile Asp Ala
1               5                   10                  15

Met Cys Ile Tyr Leu Ala Ala Cys Ser Asp Pro Phe Lys Thr
            20                  25                  30

<210> SEQ ID NO 40
<211> LENGTH: 31
<212> TYPE: PRT
<213> ORGANISM: Campylobacter jejuni

<400> SEQUENCE: 40

Phe Ser Ala Lys Asp Arg Asn Asn His Leu His His Ala Ile Asp Ala
1               5                   10                  15

Val Ile Ile Ala Tyr Ala Asn Asn Ser Ile Val Lys Ala Phe Ser
            20                  25                  30

<210> SEQ ID NO 41
<211> LENGTH: 33
<212> TYPE: PRT
<213> ORGANISM: Francisella novicida

<400> SEQUENCE: 41

Tyr Ala Lys Gly Asp Lys Pro Gln Ala Ser Tyr Ser His Leu Ile Asp
1               5                   10                  15
```

-continued

Ala Met Leu Ala Phe Cys Ile Ala Ala Asp Glu His Arg Asn Asp Gly
            20                  25                  30

Ser

<210> SEQ ID NO 42
<211> LENGTH: 39
<212> TYPE: RNA
<213> ORGANISM: HCV
<220> FEATURE:
<221> NAME/KEY: misc_feature
<222> LOCATION: (1)..(39)
<223> OTHER INFORMATION: 5' UTR

<400> SEQUENCE: 42
ugcgaaaggc cuugggguac ugccugauag ggcgcuugc                        39

<210> SEQ ID NO 43
<211> LENGTH: 87
<212> TYPE: RNA
<213> ORGANISM: HCV
<220> FEATURE:
<221> NAME/KEY: misc_feature
<222> LOCATION: (1)..(87)
<223> OTHER INFORMATION: 5' UTR rgRNA

<400> SEQUENCE: 43
guaucaggca guaccacaag cucguaauua auaaaccaug aaaguauggu uuauuagauu    60
guugaaggcu aguccguuau caacuug                                       87

<210> SEQ ID NO 44
<211> LENGTH: 40
<212> TYPE: RNA
<213> ORGANISM: HCV
<220> FEATURE:
<221> NAME/KEY: misc_feature
<222> LOCATION: (1)..(44)
<223> OTHER INFORMATION: 3' UTR

<400> SEQUENCE: 44
uucuuggugg cuccaucuua gcccuaguca cggcuagcug                        40

<210> SEQ ID NO 45
<211> LENGTH: 87
<212> TYPE: RNA
<213> ORGANISM: HCV
<220> FEATURE:
<221> NAME/KEY: misc_feature
<222> LOCATION: (1)..(87)
<223> OTHER INFORMATION: 3' UTR rgRNA

<400> SEQUENCE: 45
ugacuagggg cuaagaugga cucguaauua auaaaccaug aaaguauggu uuauuagauu    60
guugaaggcu aguccguuau caacuug                                       87

<210> SEQ ID NO 46
<211> LENGTH: 78
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (6)..(6)
<223> OTHER INFORMATION: n is any nucleotide
<220> FEATURE:
<221> NAME/KEY: misc_feature

```
<222> LOCATION: (45)..(46)
<223> OTHER INFORMATION: n is any nucleotide

<400> SEQUENCE: 46
guugunuaga uuauuuggua uguacuugug uuaguuuaaa guagnncuag aaaauucacu        60
uuuagaccua cuuauuuu                                                      78
```

CAS9-NUCLEIC ACID COMPLEXES AND USES RELATED THERETO

CROSS-REFERENCE TO RELATED APPLICATIONS

This application is a 371 U.S.C. of PCT International Patent Application filed Jan. 15, 20014 and assigned Serial No. PCT/US2014/011716, which claims the benefit of priority to U.S. Provisional Application No. 61/753,046 filed Jan. 16, 2013, and U.S. Provisional Application No. 61/905,368 filed Nov. 18, 2013, which applications are hereby incorporated by reference in their entireties.

STATEMENT REGARDING FEDERALLY FUNDED RESEARCH

This invention was made with government support under Grants U54-AI057157 and R56-AI087673 awarded by the National Institutes of Health. The Government has certain rights in the invention.

FIELD

This disclosure relates to Cas9-nucleic acid complexes and uses related thereto. In certain embodiments, the disclosure contemplates transgenic plants and animals genetically engineered to express Cas9-nucleic acid complexes disclosed herein. In certain embodiments, the disclosure relates to methods of treating or preventing, diseases, conditions, cancer, viral infections, or other pathogenic infection using vectors configured to express a Cas9-nucleic acid complex disclosed herein.

BACKGROUND

CRISPR (Clustered Regularly Interspaced Short Palindromic Repeats)-CAS (CRISPR-associated) genes provide defense against foreign nucleic acids. These systems utilize an array of small CRISPR RNAs (crRNAs) consisting of repetitive sequences flanking spacers to recognize their targets, and certain CAS proteins to mediate targeted degradation. See Hale et al., Cell, 2009, 139, 945-956; Gasiunas et al., Proc Natl Acad Sci USA, 2012, 109, E2579-2586; Jinek et al., Science, 2012, 337, 816-821; and Datsenko et al., Nat Commun, 2012, 3, 945. Garneau et al., Nature, 2010, 468, 67-71, report the CRISPR/Cas bacterial immune system cleaves bacteriophage and plasmid DNA. Barrangou et al., Science, 2007, 315, 1709-1712, report that CRISPR provides acquired resistance against viruses in prokaryotes. Marraffini & Sontheimer, Science, 2008, 322, 1843-1845, report CRISPR interference limits horizontal gene transfer in staphylococci by targeting DNA.

Horvath et al., WO2007025097, report the use of one or more Cas genes or proteins for modulating the resistance of a cell against a target nucleic acid or a transcription product thereof.

Hale et al. report essential features and rational design of CRISPR RNAs that function with the Cas RAMP module complex to cleave RNAs. Molecular Cell, 2012 45, 292-302.

Cho et al. report targeted genome engineering in human cells with the Cas9 RNA-guided endonuclease. Nature Biotechnology, 2013, 31, 230-232.

Mali et al. report RNA-guided human genome engineering via Cas9. Science, 2013, 339:823-26. See also Jinek et al., eLife, 2013, 2:e00471.

Nekrasov et al., report targeted mutagenesis in the model plant *Nicotiana benthamiana* using Cas9 RNA-guided endonuclease. Nat Biotechnol., 2013, 31(8):691-3.

References cited herein are not an admission of prior art.

SUMMARY

This disclosure relates to Cas9-nucleic acid complexes and uses related thereto. In certain embodiments, the disclosure contemplates transgenic plants and animals genetically engineered to express Cas9-nucleic acid complexes disclosed herein. In certain embodiments, the disclosure relates to methods of treating or preventing, diseases, conditions, cancer, viral infections or other pathogenic infection using vectors configured to express a Cas9-nucleic acid complex disclosed herein.

In certain embodiments, the disclosure relates to methods of treating or preventing cancer or viral infections or other pathogenic infection or other genetic diseases using vectors configured to express a Cas9-nucleic acid complex that targets viral or pathogenic nucleic acids or RNA associated with oncogenes. In certain embodiments, the disclosure contemplates transgenic plants and animals genetically engineered to express Cas9-nucleic acid complexes disclosed herein for the purpose of cancer, genetic diseases, preventing or treating viral or other pathogenic infections.

In certain embodiments, the disclosure relates to isolated or recombinant nucleic acids, cloning vectors, and recombinant cells containing the same. In certain embodiments, the disclosure relates to methods of treating or preventing viral infections or cancer or other genetic diseases comprising administering an effective amount of vector configured to express Cas9-nucleic acid complexes that target viral nucleic acids or RNA associated with oncogenes to a subject in need thereof.

In certain embodiments, the disclosure contemplates compositions and methods of knocking down endogenous bacterial or other genes or preventing the production of a target protein in a prokaryotic, eukaryotic, mammalian, human, insect or plant cell. In certain embodiments, the disclosure relates to immune stimulating compositions and uses as described herein.

In certain embodiments, the disclosure relates to recombinant nucleic acids comprising: a sequence comprising a Cas9 or bacterial Cas9 gene, a sequence encoding an RNA, wherein the RNA comprises a first segment that is configured to bind with the Cas9 after transcription and a second segment that is configured to bind a target nucleic acid. In certain embodiments, the bacterial Cas9 mRNA translates a Cas9 having SEQ ID NO: 1 or conserved variants thereof. In certain embodiments, the Cas9 has an arginine-rich, RuvC-III, and RuvC-IV motif. In certain embodiments, the Cas9 mRNA translates a Cas9 of greater than about 5% identity to SEQ ID NO: 1, a segment with 10% identity to SEQ ID NO: 6, a segment with 10% identity to SEQ ID NO: 7, and a segment with 10% identity to SEQ ID NO: 8. In certain embodiments, the first segment comprises SEQ ID NO: 5 or SEQ ID NO: 11 or 60% or more identity thereto.

In certain embodiments, the first segment comprises a bacterial derived sequence associated with tracrRNA or scaRNA configured to bind the bacterial Cas9. In certain embodiments, the first segment forms a hairpin structure. In certain embodiments, the target sequence is a viral genome or viral RNA, or mRNA or microRNA associated with an oncogene. In certain embodiments, the second segment of RNA is single stranded. In certain embodiments, the second segment comprises more than 10, 15, 20, 25, 30, 50, or 100 continuous nucleotides configured to hybridize to a target sequence. In certain embodiments, the Cas9 gene is a human, animal, or plant code optimized sequence. In certain embodiments, the Cas9 gene comprises (SEQ ID NO: 9) or 60% or more identity thereto.

In certain embodiments, the disclosure contemplates recombinant nucleic acids comprising: a sequence comprising a Cas9 or bacterial Cas9 gene, a sequence encoding SEQ ID NO: 5 or SEQ ID NO: 11 or 10%, 30%, 60%, 70%, 80%, 90%, 95% or more identity thereto conjugated a sequence encoding an third RNA, wherein the third RNA comprises more than 8 continuous nucleotides configured to hybridizes to a target sequence.

In certain embodiments the disclosure contemplates a recombinant nucleic acids comprising: a sequence encoding a single chimeric RNA 5'-[X]$_n$ CUCGUAAUUAAUAAACCAUGAAAGUAUGGUUUA UUAGAUUGUUG[Y]$_m$-3' (SEQ ID NO: 13), wherein X and Y are individually at each occurrence any nucleotide an n and m are individually 8, 10, 15, 20, 25, 30, 50, or 100 more continuous nucleotides and typically less than 50, 100, or 200 nucleotide, a targeting sequencing or non-targeting sequence, typically at least one targeting sequence, typically Y is a non-targeting sequence, and/or one of n or m is less than 10 nucleotides, wherein the recombinant nucleic acid also optionally encodes a sequence comprising a Cas9 or bacterial Cas9 gene.

In certain embodiments, the target sequence is a viral genome or mRNA or microRNA associated with an oncogene. In certain embodiments, the third RNA comprises more than 10, 15, 20, 25, 30, 50, or 100 continuous nucleotides configured to hybridize to a target sequence. In certain embodiments, the Cas9 or bacterial Cas9 gene is a human codon optimized sequence. In certain embodiments, the Cas9 gene comprises (SEQ ID NO: 9) or 10%, 30%, 50%, 60%, 70%, 80%, 90%, 95%, 98% or more identity thereto.

In certain embodiments, the disclosure relates to recombinant vectors comprising a nucleic acid disclosed herein. The recombinant vector may be selected from a genetically engineered plasmid, bacteriophage, bacterial artificial chromosome, yeast artificial chromosome, or a genetically engineered virus.

In certain embodiments, the disclosure relates to a bacterial, prokaryotic, eukaryotic, insect, mammalian, or plant cell transformed with the recombinant vector disclosed herein.

In certain embodiments, the disclosure relates to isolated or recombinant nucleic acids comprising: a sequence encoding a bacterial or any Cas9 mRNA, a sequence encoding a bacterial scaRNA, and a sequence encoding an third RNA in operable combination with promoter sequences, wherein a portion of the sequence encoding the third RNA hybridizes to the scaRNA and wherein a second portion of the sequence encoding the third RNA hybridizes to a target sequence.

In certain embodiments, the disclosure relates to isolated or recombinant nucleic acids comprising: a sequence encoding a Cas9 or bacterial Cas9 mRNA and a sequence encoding a portion of a bacterial scaRNA connected to a sequence encoding a third RNA that hybridizes to a target sequence to provide a RNA chimera, wherein the RNA chimera provides the function of both the scaRNA and the targeting RNA.

In certain embodiments, the isolated nucleic acid is a cDNA.

In certain embodiments, the Cas9 mRNA translates a Cas9 having SEQ ID NO: 1 or variants thereof.

In certain embodiments, the Cas9 has an arginine-rich, RuvC-III and RuvC-IV motif.

In certain embodiments, the Cas9 mRNA translates a Cas9 of greater than about 5%, 10%, 20%, 30%, 40%, 50%, 60%, 70%, 80%, 90%, or 95% identity to SEQ ID NO: 1.

In certain embodiments, the Cas9 has an arginine rich motif has greater than about 10%, 20%, 30%, 40%, 50%, 60%, 80%, 90%, or 95% identity to MNNRTARRHQR-RGIDRKQLVK (SEQ ID NO: 6).

In certain embodiments, the Cas9 has an RuvC-III motif with greater than about 10%, 20%, 30%, 40%, 50%, 60%, 80%, 90%, or 95% identity to KNIVDDNWQNIKQVL-SAKHQLHIPIITESNAFEFE (SEQ ID NO: 7).

In certain embodiments, the Cas9 has an RuvC-IV motif with greater than about 10%, 20%, 30%, 40%, 50%, 60%, 80%, 90%, or 95% identity to AKGDKPQASYSHLIDAM-LAFCIAADEHRNDG (SEQ ID NO: 8).

In certain embodiments, the scaRNA comprises GUU GUXUAGAUUAUUUGGUAUGUACUUGU-GUUAGUUUAAAGUAGXXCUAGAAAAU UCAC-UUUUAGACCUACUUAUUUU (SEQ ID NO: 46) wherein X is, individually at each occurrence any nucleotide.

In certain embodiments, the scaRNA has greater than about 50%, 60%, 70%, 80%, 90%, or 95% identity to SEQ ID NO: 46.

In certain embodiments, the portion of the RNA that hybridizes to the scaRNA comprises GUACCAAAUAAUU (SEQ ID NO: 5).

In certain embodiments, the RNA comprises GUAC-CAAAUAAUU[X]$_n$ (SEQ ID NO: 14) wherein X is, individually at each occurrence any nucleotide, and n is 10, 20, 50, 100, 200, or more nucleotides, typically less than 100, 200, or 500 nucleotides.

In certain embodiments, the disclosure contemplates a recombinant vector comprising any of the nucleic acid sequences disclosed herein.

In certain embodiments, the second portion of RNA that hybridizes to a target sequence, e.g., [X]$_n$, is greater than about 10, 20, 50, 100, 200, 400, or 800 nucleotides.

In certain embodiments, the disclosure relates to isolated nucleic acids disclosed herein further encoding a marker polypeptide such as an antibody epitope, ligand, polyhistidine, protein that confers resistance to an antibiotic, enzyme that breaks down an antibiotic such as beta-lactamase, or fluorescent protein such as green fluorescent protein.

In certain embodiments, the disclosure relates to cloning vectors comprising a nucleic acid disclosed herein. In certain embodiments, the cloning vector is selected from a genetically engineered plasmid, bacteriophage, bacterial artificial chromosome, yeast artificial chromosome, or a virus.

In certain embodiments, the disclosure relates to recombinant bacterial cell transformed with cloning vectors disclosed herein.

In certain embodiments, the disclosure contemplates methods of making recombinant bacterial cells comprising mixing a cloning vector disclosed herein with a bacterial cell under conditions such that nucleic acids of the cloning vector comprising the encoding sequences integrate into the genome of the bacteria cells.

In certain embodiments, the disclosure relates to methods of reducing translation of a target polypeptide comprising mixing a bacterial, prokaryotic, eukaryotic, plant, insect, or mammalian cell, wherein the bacterial, prokaryotic, eukaryotic, plant, insect, or mammalian cell translates the target polypeptide, with a cloning vector disclosed herein under conditions such that transcription of the encoded sequences occurs, translation of Cas9 occurs, and a nucleic acid complex forms, wherein the second portion of the third RNA that hybridizes to a target RNA, e.g., rRNA, non-coding RNA, or mRNA encoding the target polypeptide and translation of the target protein is reduced or the targeted RNA is degraded.

In certain embodiments, the target polypeptide has a function that is unknown. In certain embodiments, the disclosure contemplates that libraries and arrays of targeting RNAs and/or bacteria can be generated to determine the function of unknown RNA transcripts. The second portion of third RNA can be engineered to hybridize to a target RNA sequence of unknown function, e.g., mRNA, rRNA, or non-coding RNA.

In certain embodiments the disclosure relates to a vector encoding the protein-nucleic acid complex comprising: a Cas9 polypeptide, a scaRNA that forms a double stranded hairpin and comprises a portion of single stranded RNA; an RNA with a portion comprising the complement to the portion of single stranded RNA, and a second portion of the RNA that hybridizes to a target sequence, e.g., RNA. In certain embodiments, the vector can be transferred into a bacteria or prokaryotic or eukaryotic cells under conditions such that the complex is formed. Hybridization of the targeting sequence prevents the RNA transcripts, e.g., mRNA, of unknown function from performing its intended function, and the phenotype of the bacteria is analyzed to determine the effect of the knock-down. In certain embodiments, targeting by the third RNA and scaRNA and Cas9 complex leads to the degradation of the targeted RNA or hybridization prevents translation. Randomly screening large numbers of RNA transcripts of unknown function individually can be used to identify RNA transcripts that are necessary for growth, replication, or other traits.

In certain embodiments, the disclosure relates to isolated protein-nucleic acid complexes comprising: a Cas9 or bacterial Cas9 polypeptide, a scaRNA that forms a double stranded hairpin and comprises a portion of single stranded RNA; an RNA with a portion comprising the complement to the portion of single stranded RNA, and a second portion of the RNA that hybridizes to a target sequence, wherein the portion of single stranded RNA hybridized to the complement to form a RNA complex; and wherein the Cas9 or bacterial Cas9 binds with the RNA complex to form a protein-nucleic acid complex.

In certain embodiments, the disclosure relates to immune stimulating compositions comprising a bacterial strain with a mutated cas9, scaRNA, or tracrRNA gene, or combinations thereof. In certain embodiments, the mutation is in the Cas9 or bacterial Cas9 arginine-rich, RuvC-III and RuvC-IV motif. In certain embodiments, the mutation is a change or deletion of an amino acid, polypeptide, or segment. In certain embodiments, the mutation is a deletion of the scaRNA or segment, a deletion of the tracrRNA or segment, a deletion of Cas9 or segment, or creates a reverse complement in scaRNA or a reverse complement mutation in tracrRNA.

In certain embodiments, the disclosure relates to methods of immunizing a subject against a bacterial strain comprising administering of an immune stimulating composition disclosed herein to a subject in an effective amount.

In certain embodiments, the disclosure contemplates the use of a Cas9 system disclosed herein in any prokaryotic, eukaryotic, human, mammalian, or plant cell.

BRIEF DESCRIPTION OF THE FIGURES

FIG. 1A shows the schematic of the *F. novicida* Type II CRISPR-CAS locus, containing cas9, cas1, cas2, and cas4, as well as the crRNA array (repeats indicated by vertical red lines), tracrRNA (blue), scaRNA (gray), and predicted promoters (black arrows).

FIG. 1B is the relative expression of FTN_1103 in wild-type (WT), Δcas9, Δcas1, Δcas2, and Δcas4 strains.

FIG. 1C shows the relative expression of FTN_1103 in WT, Δcas9, ΔscaRNA, ΔcrRNA, and ΔtracrRNA strains (n=4, bars represent the standard deviation).

FIG. 2A is a Schematic of Cas9 domain architecture, indicating the five endonuclease domains (RuvC-I-RuvC-IV, HNH) and the ARM (arginine-rich motif).

FIG. 2B is a Relative expression of FTN_1103 in 354 wild-type (WT), Δcas9, Cas9:D11A (RuvC-I), Cas9:R59A (ARM), Cas9:E86A (RuvC-II), Cas9:R102A (RuvC-II), Cas9:D876A (RuvC-III), Cas9:H969A (HNH region), Cas9: H1162A (RuvC-IV), and Cas9:D1165A (RuvC-IV) strains (n=4, bars represent the standard deviation).

FIG. 2C shows the time course of FTN_1103 degradation following rifampin treatment in WT (black circles), Δcas9 (blue squares), ΔscaRNA (yellow triangles), and ΔtracrRNA (green diamonds) strains (n=3, points represent the mean and bars the standard deviation, $p \leq 0.05$ for all mutants at the 30 minute time point compared to wild-type).

FIG. 2D shows a schematic representing predicted hybridization between tracrRNA (beige; SEQ ID NO: 17) and scaRNA (green; SEQ ID NO:16), and scaRNA and FTN_1103 (purple; SEQ ID NO:15). Green bases distinguished by adjacent black bars represent base pairs altered in specific tracrRNA and scaRNA mutants, and red bases indicate the start codon and RBS of FTN_1103.

FIG. 2E shows Anti-FLAG immunoprecipitation was performed on lysates from WT, a strain encoding Cas9-FLAG, or Cas9:R59A-FLAG, and qRT-PCR performed on RNA from the precipitate for scaRNA FIG. 2F shows Anti-FLAG immunoprecipitation was performed on lysates from WT, a strain encoding Cas9-FLAG, or Cas9:R59A-FLAG, and qRT-PCR performed on RNA from the precipitate for tracrRNA.

FIG. 2G shows relative expression of FTN_1103 in WT, ΔscaRNA, scaRNA:rc4-8 (expressing reverse complement of bases 4-8), scaRNA:rc48-54 (expressing reverse complement of bases 48-54), ΔtracrRNA, and tracrRNA:rc13-17 (expressing reverse complement of bases 13-17) strains (n=4, bars represent the standard deviation).

FIG. 6 illustrates embodiments of bacterial Cas9 arginine-rich, ruvC-III, and RuvC-IV motifs. (*S. pyogenes* SEQ ID NOs:18, 26 and 34; *L. monocytogenes* SEQ ID NO:18, 27, and 35; *L. salivarius* SEQ ID NOs:20, 28, and 36; *N. meningitidis* SEQ ID NOs:21, 29, and 37; *L. pneumophila* SEQ ID NOs:22, 30, and 38; *Burkholdariales* SEQ ID NOs:23, 31, and 39; *C. jejuni* SEQ ID NOs:24, 32, and 40; and *F. novicida* SEQ ID NOs:25, 33, and 41).

FIG. 10A shows data FnCas9 is targeted to the HCV viral RNA. Huh7.5 cells were transfected with the HA-epitope tagged FnCas9 alone, or in conjunction with the HCV 5'UTR targeting rgRNA, or a non-specific control RNA. Transfected cells were then infected with HCV as above. At 48 hours post infection, cells were lysed and the lysate subjected to immunoprecipitation (IP) for HA. Following IP, RNA was extracted from the precipitate and analyzed for total HCV genomes by Taqman qRT-PCR, and normalized by GAPDH levels. Significant enrichment of HCV genomes are seen in the precipitate when FnCas9 is directed by an HCV specific rgRNA, but not with the non-specific control.

FIG. 10B—precipitated RNA was analyzed for the presence of the targeting rgRNAs by Syber Green qRT-PCR, normalizing to gapdh.

FIG. 10C—precipitated RNA was analyzed for the presence of the targeting rgRNAs by Syber Green qRT-PCR, normalizing to gapdh

DETAILED DESCRIPTION

Figure 1A:
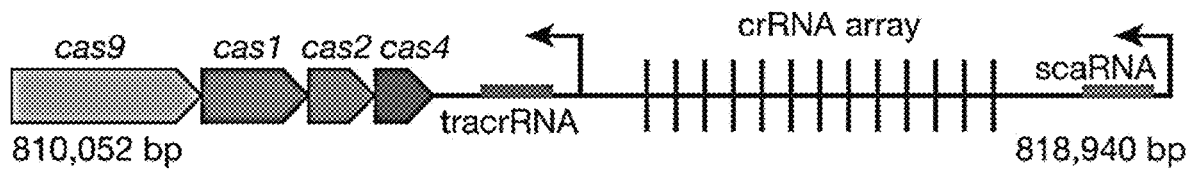
FIGS. 1A, 1B and 1C show data indicating Cas9, tracrRNA, and scaRNA are important for FTN_1103 repression.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure.

Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, "subject" refers to any animal, preferably a human patient, livestock, or domestic pet.

As used herein, the term "nucleic acid" refers to a single or double-stranded polymer of deoxyribonucleotide or ribonucleotide bases read from the 5' to the 3' end. The "nucleic acid" may also optionally contain non-naturally occurring or altered nucleotide bases that permit correct read through by a polymerase and do not reduce expression of a polypeptide encoded by that nucleic acid. The term "nucleotide sequence" or "nucleic acid sequence" refers to both the sense and antisense strands of a nucleic acid as either individual single strands or in the duplex. The term "ribonucleic acid" (RNA) is inclusive of RNAi (inhibitory RNA), dsRNA (double stranded RNA), siRNA (small interfering RNA), mRNA (messenger RNA), miRNA (micro-RNA), tRNA (transfer RNA, whether charged or discharged with a corresponding acylated amino acid), and cRNA (complementary RNA) and the term "deoxyribonucleic acid" (DNA) is inclusive of cDNA and genomic DNA and DNA-RNA hybrids. The words "nucleic acid segment", "nucleotide sequence segment", or more generally "segment" will be understood by those in the art as a functional term that includes both genomic sequences, ribosomal RNA sequences, transfer RNA sequences, messenger RNA sequences, small regulatory RNAs, operon sequences and smaller engineered nucleotide sequences that express or may be adapted to express, proteins, polypeptides or peptides.

Nucleic acids of the present disclosure may also be synthesized, either completely or in part, especially where it is desirable to provide plant-preferred sequences, by methods known in the art. Thus, all or a portion of the nucleic acids of the present codons may be synthesized using codons preferred by a selected host. Species-preferred codons may be determined, for example, from the codons used most frequently in the proteins expressed in a particular host species. Other modifications of the nucleotide sequences may result in mutants having slightly altered activity.

The term "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present disclosure may contain endogenous enhancers/promoters, splice junctions, intervening sequences, polyadenylation signals, etc. or a combination of both endogenous and exogenous control elements.

The term "cDNA" refers to complementary DNA (cDNA), i.e., DNA synthesized from a RNA (e.g. mRNA) template typically catalyzed by the enzymes reverse transcriptase and DNA polymerase.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene. The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (mRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "heterologous gene" refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise bacterial gene sequences that comprise cDNA forms of a bacterial gene; the cDNA sequences may be expressed in either a sense (to produce mRNA) or anti-sense orientation (to produce an anti-sense RNA transcript that is complementary to the mRNA transcript).

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The nucleic acid molecules or guided or targeting RNA disclosed herein are capable of specifically hybridizing to the target nucleic acid under certain circumstances. As used herein, two nucleic acid molecules are said to be capable of specifically hybridizing to one another if the two molecules are capable of forming a hydrogen bonding nucleic acid structure. A nucleic acid molecule may exhibit complete complementarity. Two molecules are said to be "minimally complementary" if they can hybridize to one another with sufficient stability to permit them to remain annealed to one another under at least conventional "low-stringency" conditions. Similarly, the molecules are said to be complementary if they can hybridize to one another with sufficient stability to permit them to remain annealed to one another under conventional "high-stringency" conditions. Conventional stringency conditions are described by Sambrook, et al. (1989), and by Haymes et al. (1985).

Departures from complete complementarity are therefore permissible, as long as such departures do not completely preclude the capacity of the RNA molecules to form a hydrogen bonding structure with the target. Thus, in order for an RNA to serve as a guide to the target, the RNA needs only be sufficiently complementary in sequence to be able to form a stable hydrogen bonding structure under the physiological conditions of the cell expressing the RNA.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

A "cloning vector" or "vector" refers to a nucleic acid molecule used as a vehicle to carry foreign genetic material into another cell, where it can be replicated and/or expressed. A cloning vector containing foreign nucleic acid is termed a recombinant vector. Examples of vectors are plasmids, viral vectors, cosmids, and artificial chromosomes. Recombinant vectors typically contain an origin of replication, a multicloning site, and a selectable marker. The nucleic acid sequence typically consists of an insert (recombinant nucleic acid or transgene) and a larger sequence that serves as the "backbone" of the vector. The purpose of a vector which transfers genetic information to another cell is typically to isolate, multiply, or express the insert in the target cell. Expression vectors (expression constructs) are for the expression of the transgene in the target cell, and generally have a promoter sequence that drives expression of the transgene. Insertion of a vector into the target cell is referred to transformation or transfection for bacterial and eukaryotic cells, although insertion of a viral vector is often called transduction.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. In contrast, a "regulatable" or "inducible" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene.

Efficient expression of recombinant DNA sequences in eukaryotic cells is believed to include the expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene.

The term "marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotransferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See, e.g., deWet et al., Mol. Cell. Biol. 7:725 (1987) and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from ClonTech Laboratories, Palo Alto, Calif.), chloramphenicol acetyltransferase, .beta.-galactosidase, alkaline phosphatase, and horse radish peroxidase.

"Sequence identity" refers to a measure of relatedness between two or more nucleic acids or proteins, and is typically given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.) using default parameters. In certain embodiments, sequence "identity" refers to the number of exactly matching residues (expressed as a percentage) in a sequence alignment between two sequences of the alignment. In certain embodiments, percentage identity of an alignment may be calculated using the number of identical positions divided by the greater of the shortest sequence or the number of equivalent positions excluding overhangs wherein internal gaps are counted as an equivalent position. For example the polypeptides GGGGGG and GGGGT have a sequence identity of 4 out of 5 or 80%. For example, the polypeptides GGGPPP and GGGAPPP have a sequence identity of 6 out of 7 or 85%.

In certain embodiments, for any contemplated percentage sequence identity, it is also contemplated that the sequence may have the same percentage of sequence similarity. Percent "similarity" is used to quantify the extent of similarity, e.g., hydrophobicity, hydrogen bonding potential, electrostatic charge, of amino acids between two sequences of the alignment. This method is similar to determining the identity except that certain amino acids do not have to be identical to have a match. In certain embodiments, sequence similarity may be calculated with well-known computer programs using default parameters. Typically, amino acids are classified as matches if they are among a group with similar properties, e.g., according to the following amino acid groups: Aromatic—F Y W; hydrophobic—A V I L; Charged positive: R K H; Charged negative—D E; Polar—S T N Q.

A partially complementary sequence is one that at least partially inhibits (or competes with) a completely complementary sequence from hybridizing to a target nucleic acid—also referred to as "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math. 2: 482 (1981)) by the homology alignment algorithm of Needleman and Wunsch (Needleman and Wunsch, J. Mol. Biol. 48:443 (1970)), by the search for similarity method of Pearson and Lipman (Pearson and Lipman, Proc. Natl. Acad. Sci. (U.S.) 85:2444 (1988)), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. In certain embodiment, the term "sequence identity" refers to two polynucleotide sequences are identical (i.e., on a nucleotide-by-nucleotide basis) over the window of comparison. In some embodiments, the term "percentage of sequence identity" over a comparison window is calculated by comparing two optimally aligned sequences over the window of comparison, determining the number of positions at which the identical nucleic acid base (e.g., A, T/U, C, G, or I) occurs in both sequences to yield the number of matched positions, dividing the number of matched positions by the total number of positions in the window of comparison (i.e., the window size), and multiplying the result by 100 to yield the percentage of sequence identity.

The terms "variant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Certain variants have less than 10%, and preferably less than 5%, and still more preferably less than 2% changes (whether substitutions, deletions, and so on).

A CRISPR-CAS System Mediates Bacterial Innate Immune Evasion and Virulence

It has been discovered that the CAS protein Cas9 of *Francisella novicida* utilizes a unique, small, CRISPR-CAS-associated RNA (scaRNA) to mediate the repression of an endogenous transcript encoding a bacterial lipoprotein (BLP). As BLPs trigger a proinflammatory innate immune response aimed at combating pathogens, CRISPR-CAS mediated repression of BLP is critical for *F. novicida* to dampen the host inflammatory response and promote virulence. Cas9 proteins are highly enriched in pathogenic and commensal bacteria. Studies disclosed herein indicate that CRISPR-CAS-mediated gene regulation may broadly contribute to the interaction of such bacteria with eukaryotic hosts.

*F. novicida* is an intracellular pathogen that evades host defenses as it traffics through the phagosome of eukaryotic cells to replicate to high numbers within the cytosol. It has developed mechanisms to prevent recognition by a variety of pattern recognition receptors (PRR) that detect bacteria and localize to the surface and phagosomes of host phagocytic cells. One PRR, Toll-like Receptor 2 (TLR2), recognizes BLP and is important for defense against *F. novicida*. By dampening TLR2 activation, *F. novicida* reaches its replicative niche in the cytosol without inducing significant inflammatory signaling, promoting its pathogenesis.

Figure 5:
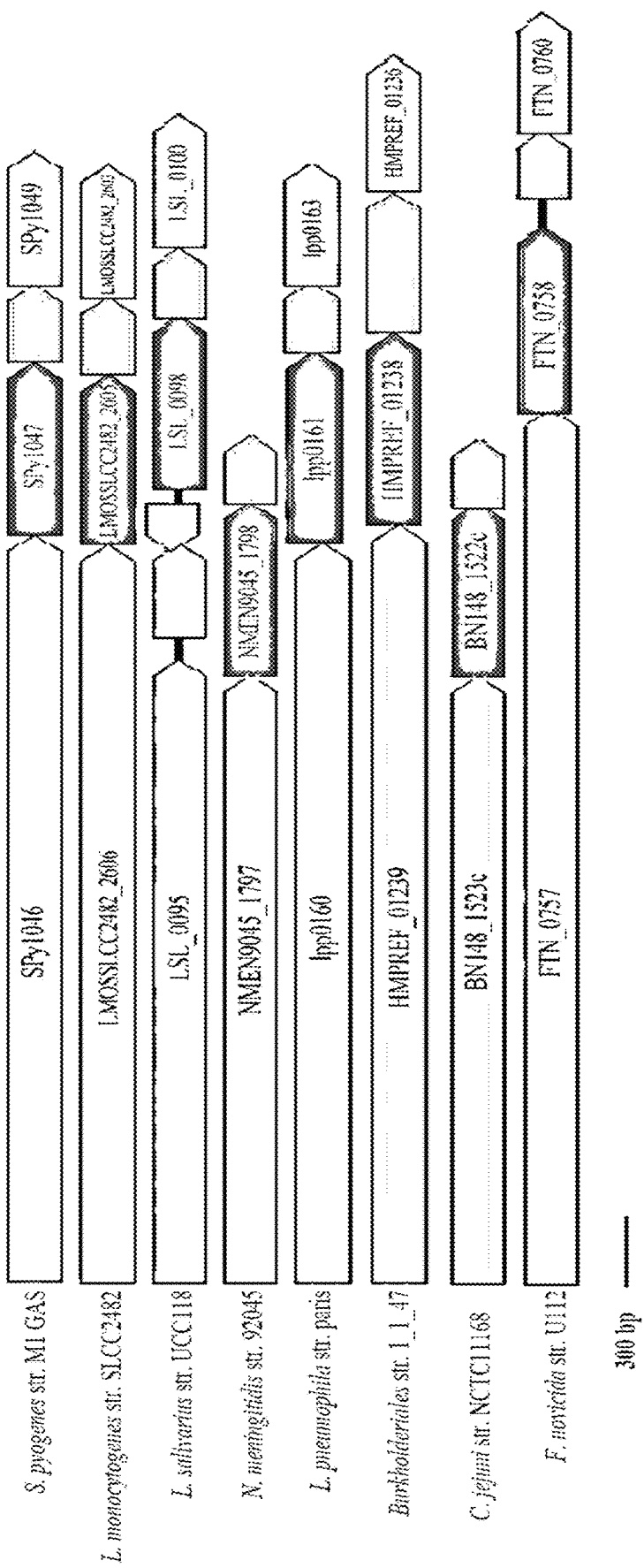
FIG. 5 illustrates embodiments of certain bacterial Cas9, tracrRNA, and scaRNA.

*F. novicida* gene FTN_0757 is involved in the repression of a BLP encoded by the gene FTN_1103 although its mechanism of action was unclear. See Jones et al., entitled "Repression of bacterial lipoprotein production by *Francisella novicida* facilitates evasion of innate immune recognition," Cell Microbiol, 2012. Unexpectedly, bioinformatics analysis revealed that FTN_0757 has significant sequence similarity to the CRISPR-CAS system protein Cas9, (See FIG. 5) typically known to mediate the degradation of foreign DNA and not currently known to play a role in endogenous gene regulation.

Furthermore, FTN_0757 is present in a complete Type II CRISPR-CAS system locus. The Type II CRISPR-CAS system is found in the genomes of pathogens and commensals such as *Streptococcus* spp., *Listeria* spp., *Neisseria* spp., and *Lactobacillus* spp. See FIG. 6. The locus contains Cas1, Cas2, and Cas4, all predicted to be involved in adaptive resistance by acquiring new targeting crRNAs as well as a predicted trans-activating RNA (tracrRNA), an accessory small RNA necessary for crRNA activity. It also contains a unique small RNA previously undescribed in a CRISPR locus, distinct from the crRNAs and tracrRNA, referred to herein as Small CRISPR-CAS-associated RNA (scaRNA) (FIG. 1A). Bacterial Cas9 homologs including those mentioned in (Chylinski, 2013, *RNA Biol*) and those listed below:

| | |
|---|---|
| *Bacteroides fragilis* | *Campylobacter lari* |
| *Bifidobacterium dentium* | *Capnocytophaga ochracea* |
| *Campylobacter jejuni* | *Clostridium botulinum* |

-continued

| | |
|---|---|
| Corynebacterium diphtheriae | Rhodococcus erythropolis |
| Corynebacterium kroppenstedtii | Scardovia wiggsiae |
| Enterococcus faecalis | Sphingobacterium spiritivorum |
| Facklamia hominis | Staphylococcus aureus |
| Finegoldia magna | Streptobacillus moniliformis |
| Flavobacterium psychrophilum | Streptococcus agalactiae |
| Francisella holarctica | Streptococcus dysgalactiae equisimili |
| Francisella novicida | Streptococcus equi zooepidemicus |
| Francisella tularensis | Streptococcus gallolyticus |
| Gemella haemolysans | Streptococcus gordonii |
| Haemophilus parainfluenzae | Streptococcus macedonicus |
| Haemophilus pittmaniae | Streptococcus mitis |
| Helicobacter hepaticus | Streptococcus mutans |
| Lactobacillus casei | Streptococcus oralis |
| Lactobacillus fermentum | Streptococcus parasanguinis |
| Lactobacillus rhamnosus | Streptococcus pasteurianus |
| Legionella pneumophila | Streptococcus pseudoporcinus |
| Leptospira inadai serovar Lyme | Streptococcus pyogenes |
| Listeria innocua | Treponema denticola |
| Listeria monocytogenes | Veillonella parvula |
| Mycobacterium abscessus | Weeksella virosa |
| Mycoplasma gallisepticum | Actinobacillus succinogenes |
| Mycoplasma mobile | Akkermansia muciniphila |
| Mycoplasma penetrans | Azospirillum B510 |
| Mycoplasma synoviae | Barnesiella intestinihominis |
| Myroides odoratus | Bifidobacterium longum |
| Neisseria cinerea | Bradyrhizobium |
| Neisseria flavescens | Burkholderiales bacterium |
| Neisseria lactamica | Butyrivibrio fibrisolvens |
| Neisseria meningitidis | Dinoroseobacter shibae |
| Nocardia farcinica | Eubacterium rectale |
| Olsenella uli | Eubacterium yurii subsp. margaretiae |
| Pasteurella multocida | Fibrobacter succinogenes |
| Pseudoalteromonas atlantica | Gluconacetobacter diazotrophicus |
| Lactobacillus salivarius | |
| Parasutterella excrementihominis | |
| Roseburia intestinalis | |
| Roseburia inulinivorans | |
| Slackia heliotrinireducens | |
| Streptococcus thermophilus | |
| Sutterella parvirubra | |
| Sutterella wadsworthensis | |
| uncultured Termite group 1 bacterium | |
| Verminephrobacter eiseniae | |
| Acidothermus cellulolyticus | |
| Alicyclobacillus hesperidum | |
| Arthrobacter chlorophenolicus | |
| Clostridium cellulolyticum | |
| Corynebacterium efficiens | |
| Corynebacterium glutamicum | |
| Desulfovibrio salexigens | |
| Diaphorobacter TPSY | |
| Elusimicrobium minutum | |
| Kribbella flavida | |
| Nitrobacter hamburgensis | |
| Parvibaculum lavamentivorans | |
| Persephonella marina | |
| putative gamma proteobacterium HTCC5015 | |
| Rhodococcus jostii | |
| Rhodococcus opacus | |
| Rhodospirillum rubrum | |
| Roseiflexus castenholzii | |
| Roseiflexus RS-1 | |
| Synechocystis PCC6803 | |
| Thermomonospora curvata | |
| Tolumonas auensis | |
| Wolinella succinogenes. | |

Figure 7A:
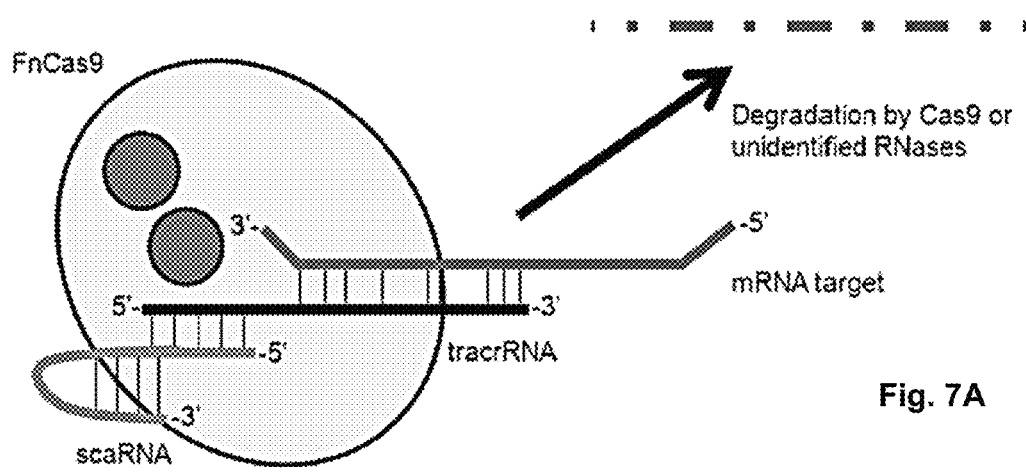
FIG. 7A schematically illustrates FnCas9 interaction with an RNA target. FnCas9 associates with a dsRNA complex formed by two small RNAs, tracrRNA and the scaRNA. Together, this allows tracrRNA to target an mRNA transcript. Subsequently, the mRNA target's stability is reduced and the transcript lost. This occurs by either currently unidentified FnCas9 activity or by the action of endogenous RNases.
Figure 7B:
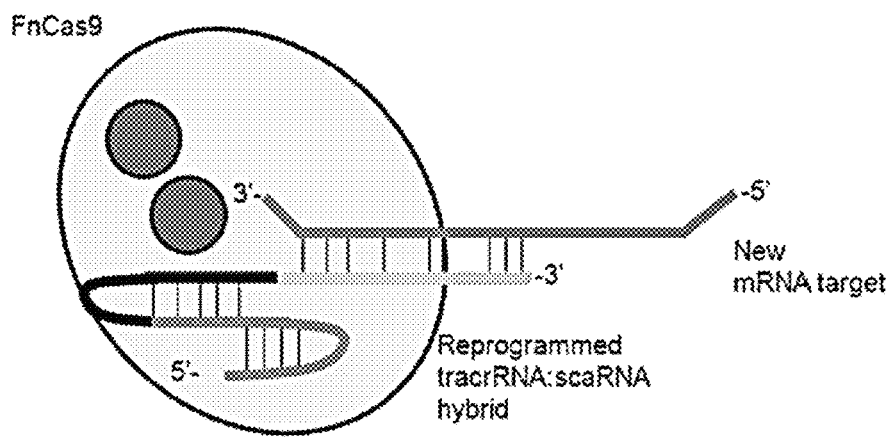
FIG. 7B is a schematic representative of a hypothetical tracrRNA:scaRNA hybrid which has been reprogrammed to target a new mRNA.
Figure 8A:
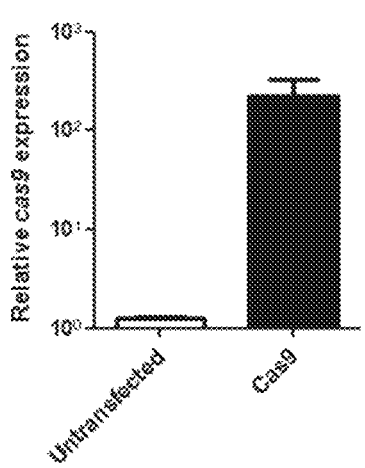
FIG. 8 shows data indicating *Francisella novicida* Cas9 is expressed and produced in human cells. Human hepatocellular carcinoma cells (Huh7.5 cells) were transfected with the pcDNA3.3 eukaryotic expression vector, containing the open reading frame for an HA epitope tagged *F. novicida* Cas9 (FnCas9), driven by the CMV promoter. A) Total RNA was extracted and qRT-PCR was performed for FnCas9 transcript and normalized to gapdh. B) Total protein was extracted, separated by SDS-PAGE, and analyzed by western blot using anti-HA to detect FnCas9 and anti-GAPDH, as a loading control.
Figure 8B:
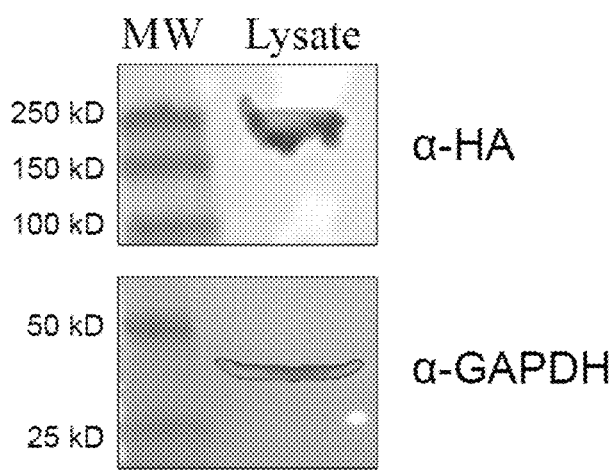

Studies herein indicate that the Cas9 system has a non-canonical function beyond the current paradigm of foreign DNA defense to act with a non-crRNA, the tracrRNA as well as the scaRNA, to regulate gene expression via targeting of endogenous mRNA, leading to innate immune evasion and virulence. See FIG. 7. This surprising observation shows that CRISPR-CAS components have been co-opted to perform functions distinct from defense against foreign nucleic acids. -CAS components are actively induced during infection of host cells by an intracellular pathogen. By activating Cas9, tracrRNA, and the scaRNA to repress FTN_1103 when F. novicida is present in the host phagosome, this pathogen temporally represses its BLP expression and thereby evades TLR2 signaling. Eighty-five of a group of 109 bacteria that are known to encode Cas9 are pathogens or commensals indicating that the CRISPR-CAS component-mediated regulatory mechanism may function in other organisms that interact with eukaryotic cells.

Cas9 and Targeting Nucleic Acid Complexes for Use to Alter Gene Expression in Various Biological Systems In certain embodiments, the disclosure relates to compositions and methods that use Cas9 systems disclosed herein, e.g., Cas9, tracrRNA, and scaRNA, to target RNAs of interest in the context of various biological systems. This allows the Cas9 system to function as a form of RNA interference. Cas9 is capable of functioning in the eukaryotic cytosol. By using longer targeting RNAs one can increase specificity. In certain embodiments, the disclosure contemplates a segment of a targeting RNA of greater than 10, 20, 30, 40, 50, 60, 70, 80, 90, or 100 nucleotides. Cas9 systems disclosed herein leads to lower levels of protein from an RNA that is targeted. With regard to the claimed embodiments, it is not intended that reduction of protein result by any particular mechanism. It is believed that in some cases the RNA is likely degraded, but it is also possible that Cas9 simply sits on the target RNA blocking access by the ribosome, thereby blocking translation or by some other unappreciated mechanism.

It is believed that Cas9 does not rely on any canonical RNAi host factors, such as Dicer or the components of the RISC complex, allowing use in systems which may have intrinsic inhibition of RNAi. Therefore, engineering of Cas9 as programmable RNA-directed RNA targeting systems is beneficial in numerous biological systems. While in some instances Cas9 is directed to its binding site by a "guide RNA" (gRNA or targeting RNA, or RNA-targeting guide RNA or rgRNA) that hybridizes to a target sequence, it is contemplated that the guide may contain a certain number of mismatches or secondary structures. In certain embodiments, the rgRNA is a fusion of the tracrRNA and scaRNAs or variant sequences thereof. In order to combat non-target interactions, certain strategies maybe used, e.g., creating rgRNA secondary structures that inhibit non-target interactions or altering the length of the rgRNA.

Cas9 in mammalian cells targeted to recognize viral RNAs prevents productive viral replication. Cas9 can be targeted to any RNA by changing the sequence of the RNA-targeting guide RNA as an anti-viral strategy capable of combating any virus. Cas9 system offer superiority with regard to conventional RNAi for treating or preventing viral infections. Viruses can mutate to evade conventional RNAi systems. The host RNAi machinery relies on sequences of 19-21 bp to interact with the targets to be degraded. In some cases even single base pair mutations in the target can completely abrogate degradation by the host RNAi machinery. RNAi with Cas9 RNA-targeting guide RNA does not rely on endogenous RNA silencing machinery of the host, i.e., self-sufficient.

Viruses can directly suppress the RNAi machinery, but are not believed to suppress Cas9 activity because Cas9 is derived from bacteria, i.e., because viral pathogens have not evolved with Cas9, viruses likely cannot escape this system. In certain embodiments, it is contemplated that multiple rgRNAs targeting different regions of viral RNA, e.g., HCV RNA, simultaneously (multiplexing), can be utilized limiting the chances that viral mutations would facilitate escape from this targeting system.

Suitable methods for transformation of host cells for use with the disclosure are believed to include virtually any method by which nucleic acids, e.g., DNA can be introduced into a cell, such as by transformation of protoplasts (U.S. Pat. No. 5,508,184), by desiccation/inhibition-mediated DNA uptake, by electroporation, by agitation with silicon carbide fibers U.S. Pat. Nos. 5,302,523; and 5,464,765), by Agrobacterium-mediated transformation (U.S. Pat. Nos. 5,563,055; 5,591,616; 5,693,512; 5,824,877; 5,981,840; 6,384,301) and by acceleration of DNA coated particles (U.S. Pat. Nos. 5,015,580; 5,550,318; 5,538,880; 6,160,208; 6,399,861; 6,403,865), etc. Through the application of techniques such as these, the cells of virtually any species may be stably transformed. In the case of multicellular species, the transgenic cells may be regenerated into transgenic plants and organisms.

Plants and animals genetically engineered to express Cas9 with RNA targeting (rgRNA) or multiple RNA-targeting RNAs specific for different viruses or pests can used to create pest-resistant progeny. In certain embodiments, the disclosure relates to generating transgenic insect vectors that are resistant to viral infection.

In certain embodiments, the disclosure contemplates the expression of Cas9 and a gRNA in eukaryotic cells used to target viruses, e.g., Hepatitis C (HCV) RNA, and prevent viral replication. Targeting Cas9 to the eukaryotic cell cytosol was done in order to target HCV RNA (HCV is an RNA virus, and has no DNA stage). Cas9 engineering studies in mammalian cells typically include NLS (nuclear localization signal) to the protein and targeted it to the nucleus in order to target DNA. In certain embodiments, a recombinantly produce Cas9 of this disclosure does not contain a NLS sequence. Cas9 has activity in the cytosol of a eukaryotic cell. Cas9 in the cytosol of eukaryotic cells may be used to target RNA or may be used to prevent its translation into protein. A Cas9 nucleic acid complex may be configured to target any RNA by changing the sequence of the "guide" RNA.

Targeting of mRNA by the Cas9 system can use a much larger region of complementarity (in the range of 50 bp) that can also tolerate imperfect hybridization (mismatches, loops, etc.). This may be used to generate a "tunable" system in which one can control how much of a given RNA is knocked down. In certain embodiments, the disclosure contemplates single stranded targeting nucleic acids in the range of 25 to 50 nucleotides, or 25 to 100 or more nucleotides, or 35 to 65 nucleotides or more nucleotides, or 40 to 60 nucleotides or more nucleotides.

In certain embodiments, the disclosure contemplates targeting numerous genes or target RNAs at the same time, e.g., host genes at the same time, viral genes at the same time, or viral and host genes at the same time. In certain embodiments, the disclosure contemplates that the Cas9 system can be used to target host RNAs. In certain embodiments, a combination of targeting viral RNA and host RNAs encoding factors that promote viral infection.

In certain embodiments, the disclosure contemplates that one may skew the immune response (e.g. to a Th1, Th2, or Th17 phenotype). One may treat an infection with a pathogen that induces a Th2 response with an rgRNA that will skew the response back to Th1 and lead to clearance of the pathogen.

Transgenic Plants Expressing Cas9 and Targeting Nucleic Acid Complexes

In certain embodiments, the disclosure contemplates plants genetically engineered to express Cas9-nucleic acid complexes disclosed herein, e.g., for the purpose of preventing infections from viral or other pests. In certain embodiments, the present disclosure relates to genetically modifying a plant to confer pest resistance by transforming a host plant cell with a heterologous nucleic acid configured to express a Cas9-nucleic acid complex disclosed herein.

In certain embodiments, the disclosure provides recombinant nucleic acid constructs for use in achieving stable transformation of particular host targets, e.g., plants and plant cells. Transformed host targets may express effective levels of Cas9 systems disclosed herein from the recombinant nucleic acid constructs. Provided according to the disclosure are nucleic acids that express certain Cas9 or bacterial Cas9 nucleotide sequences and RNA that binds the Cas9 conjugated to a nucleic acid sequences that hybridizes to an RNA molecule of a targeted gene in a plant or plant pest or combinations thereof.

In certain embodiment, the disclosure provides nucleic acid sequences capable of being expressed as RNA in a cell to inhibit target gene expression in a cell or tissue of a plant, plant pest or combinations thereof. The sequences comprise a nucleic acid molecule coding for one or more different nucleotide sequences, wherein each of the different nucleotide sequences target a plant pest RNA molecule. The sequences may be connected by a spacer sequence. The nucleic acid molecule that encodes the Cas9 and targeting RNA may be placed operably under the control of a promoter sequence that functions in the cell or tissue of the host.

In certain embodiments, a targeted sequence is in the genome of the pest or the RNA of a gene in the genome of the pest. In certain embodiments, a targeted sequence is selected that is essentially involved in the growth and development of a pest, for example, mRNA of proteins that play important roles in viability, growth, development, infectivity and of the pest. These mRNA targets may be one of the house keeping genes, transcription factors and the like.

In certain embodiments, the disclosure provides a nucleic acid sequence for expression in a cell of a plant that, upon expression of the Cas9 and targeting RNA and ingestion by a plant pest, achieves suppression of a target in a cell or tissue. Methods to express a gene suppression molecule in plants are known (e.g. WO06073727 A2; US Publication 2006/0200878 A1), and may be used to express a nucleotide sequence disclosed herein.

A nucleic acid sequence may be cloned between two tissue specific promoters, such as two root specific promoters which are operable in a transgenic plant cell and therein expressed to produce mRNA in the transgenic plant cell. Examples of root specific promoters are known in the art (e.g. the nematode-induced RB7 promoter; U.S. Pat. No. 5,459,252).

Promoters that function in different plant species are also well known in the art. Promoters useful for expression of polypeptides in plants include those that are inducible, viral, synthetic, or constitutive, and/or promoters that are temporally regulated, spatially regulated, and spatio-temporally regulated. Preferred promoters include the enhanced CaMV35S promoters, and the FMV35S promoter. A fragment of the CaMV35S promoter exhibiting root-specificity may also be preferred. For the purpose of the present disclosure, it may be preferable to achieve the highest levels of expression of these genes within the root tissues of plants.

A number of root-specific promoters have been identified and are known in the art (e.g. U.S. Pat. Nos. 5,110,732; 5,837,848; 5,459,252).

A recombinant vector or cloning vector of the present disclosure may also include a screenable marker. Screenable markers may be used to monitor expression. Exemplary screenable markers include a beta-glucuronidase or uidA gene (GUS) which encodes an enzyme for which various chromogenic substrates are known; an R-locus gene, which encodes a product that regulates the production of anthocyanin pigments (red color) in plant tissues; a beta-lactamase gene, a gene which encodes an enzyme for which various chromogenic substrates are known (e.g., PADAC, a chromogenic cephalosporin); a luciferase gene a xylE gene which encodes a catechol dioxygenase that can convert chromogenic catechols; an alpha-amylase gene; a tyrosinase gene which encodes an enzyme capable of oxidizing tyrosine to DOPA and dopaquinone which in turn condenses to melanin; an alpha-galactosidase, which catalyzes a chromogenic alpha-galactose substrate.

Preferred plant cloning or transformation vectors include those derived from a Ti plasmid of *Agrobacterium tumefaciens* (e.g. U.S. Pat. Nos. 4,536,475, 4,693,977, 4,886,937, 5,501,967 and EP 0 122 791). *Agrobacterium rhizogenes* plasmids (or "Ri") are also useful and known in the art. A transgenic plant formed using *Agrobacterium* transformation methods typically contains a single simple recombinant DNA sequence inserted into one chromosome and is referred to as a transgenic event. Such transgenic plants can be referred to as being heterozygous for the inserted exogenous sequence. A transgenic plant homozygous with respect to a transgene can be obtained by sexually mating (selfing) an independent segregant transgenic plant that contains a single exogenous gene sequence to itself, for example an F0 plant, to produce F1 seed. One fourth of the F1 seed produced will be homozygous with respect to the transgene. Germinating F1 seed results in plants that can be tested for heterozygosity, typically using a SNP assay or a thermal amplification assay that allows for the distinction between heterozygotes and homozygotes (i.e., a zygosity assay). Crossing a heterozygous plant with itself or another heterozygous plant typically results in only heterozygous progeny.

In general it may be preferred to introduce a functional recombinant DNA at a non-specific location in a plant genome. In special cases it may be useful to insert a recombinant nucleic acid construct by site-specific integration. Several site-specific recombination systems exist which are known to function in plants include cre-lox as disclosed in U.S. Pat. No. 4,959,317 and FLP-FRT as disclosed in U.S. Pat. No. 5,527,695.

In certain embodiments, a seed having the ability to express a Cas9 system disclosed herein also has a transgenic event that provides herbicide tolerance. One beneficial example of a herbicide tolerance gene provides resistance to glyphosate, N-(phosphonomethyl)glycine, including the isopropylamine salt form of such herbicide.

In addition to direct transformation of a plant with a recombinant DNA construct, transgenic plants can be prepared by crossing a first plant having a recombinant DNA construct with a second plant lacking the construct. For example, recombinant DNA for gene suppression can be introduced into first plant line that is amenable to transformation to produce a transgenic plant that can be crossed with a second plant line to introgress the recombinant DNA for gene suppression into the second plant line.

In certain embodiments, the present disclosure may be used for transformation of any plant, including, but not limited to, corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassaya (*Manihot esculenta*), coffee (*Cofea* ssp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidental*), macadamia (*Macadamia integrifolia*), almond (*Prunus amygdalus*), sugar beets (*Beta vulgaris*), oats, barley, vegetables, ornamentals, and conifers.

In certain embodiments, crop plants are contemplated (for example, cereals and pulses, maize, wheat, potatoes, tapioca, rice, *sorghum*, millet, cassaya, barley, pea, and other root, tuber, or seed crops. Important seed crops for the present disclosure are oil-seed rape, sugar beet, maize, sunflower, soybean, and *sorghum*. In certain embodiments, horticultural plants are contemplated including lettuce, endive, and vegetable brassicas including cabbage, broccoli, and cauliflower, and carnations, geraniums, petunias, and begonias. The present disclosure may be applied to tobacco, cucurbits, carrot, strawberry, sunflower, tomato, pepper, *chrysanthemum*, poplar, *eucalyptus*, and pine. In certain embodiments, plants such as grain seeds, such as corn, wheat, barley, rice, *sorghum*, rye are contemplated. In certain embodiments, plants such as oil-seed plants are contemplated. Oil seed plants include canola, cotton, soybean, safflower, sunflower, *Brassica*, maize, alfalfa, palm, coconut, etc. In certain embodiments, plants such as leguminous plants are contemplated. Leguminous plants include beans and peas. Beans include guar, locust bean, fenugreek, soybean, garden beans, cowpea, mung bean, lima bean, fava bean, lentils, chickpea, etc.

In certain embodiments, the plants are monocots and/or dicots. Non-limiting examples of useful monocots are rice, corn, wheat, palm trees, turf grasses, barley, and oats. Non-limiting examples of useful dicots are soybean, cotton, alfalfa, canola, flax, tomato, sugar beet, sunflower, potato, tobacco, corn, wheat, rice, lettuce, celery, cucumber, carrot, cauliflower, grape, and turf grasses. In certain embodiments, plants such as flowering plants, trees, grasses, shade plants, and flowering and non-flowering ornamental plants are contemplated.

Plant pests useful in the present disclosure (i.e., can be rendered non-pathogenic or reduced pathogenicity), include fungi, nematodes, bacteria, and parasitic plants such as *striga*, dodder and mistletoe. Plant pests usefully treated by the present disclosure include the downy mildews.

The skilled artisan can readily identify pest genes to target. Such a gene could be any pest gene that serves a direct or indirect role in such a pest's deleterious effects on a host plant. By way of example only, such a gene may be one that serves a role in pest growth, development, replication and reproduction, and invasion or infection.

In certain embodiments, the pest is a plant virus. Exemplary of such plant viruses are soybean mosaic virus, bean pod mottle virus, tobacco ring spot virus, barley yellow dwarf virus, wheat spindle streak virus, soil born mosaic virus, wheat streak virus in maize, maize dwarf mosaic virus, maize chlorotic dwarf virus, cucumber mosaic virus, tobacco mosaic virus, alfalfa mosaic virus, potato virus X, potato virus Y, potato leaf roll virus and tomato golden mosaic virus. Among these, protection against maize dwarf mosaic virus, barley yellow dwarf virus, wheat streak mosaic virus, soil born mosaic virus, potato leafroll virus and cucumber mosaic virus is particularly important.

In certain embodiments, the pest is *Botrytis cinerea*, a necrotrophic pathogenic fungus with an exceptionally wide host range. The cultivated tomato (predominantly *Lycopersicon esculentum*) is also susceptible to infection by *Botrytis* and the fungus generally affects stem, leaves and fruit of the tomato plant.

Transgenic Animals Expressing Cas9 and Targeting Nucleic Acid Complexes

In addition to transgenic plant, certain embodiments the disclosure contemplates transgenic animals that express Cas9 systems disclosed herein to prevent pathogenic infections, e.g., viruses. Non-limiting examples of contemplated transgenic animals include fish, livestock, and pets. In certain embodiments, the disclosure contemplates transforming embryonic stem cells (ES cells) growing in tissue culture with the desired nucleic acids that encode or express a Cas9 system disclosed herein. In certain embodiments, the disclosure contemplates injecting a cloning vector disclosed herein into isolated embryonic stem cells of a human or non-human animal.

One can transform ES cells in culture by mixing embryonic stem cells with a vector that encodes Cas9 systems disclosed herein under conditions that the ES cells incorporated the nucleic acids into the genome of the ES cell. One can isolate and select successfully transformed cells by injecting transformed cells into the inner cell mass (ICM) of a blastocyst, followed by preparing a pseudopregnant animal, e.g., by mating a female with a vasectomized male. The stimulus of mating elicits the hormonal changes typically needed to make the uterus receptive. Alternatively, direct administration of hormones may be utilized. Implanting the embryos into the uterus provides conditions to develop a transgenic animal with nucleic acids that express Cas9 systems disclosed herein.

As an alternative method to create a transgenic animal, one can transform fertilized eggs by injecting a cloning vector into the sperm pronucleus. After fusion the zygote will divide to form two embryo cells. One can implant the embryos in a pseudopregnant foster as described above.

In certain embodiments, the disclosure contemplates a transgenic animal comprising a nucleic acid that express Cas9 systems disclosed herein in combination with another protein, e.g., growth hormone. The cloning vectors disclosed herein may be configured to replace a target gene.

In certain embodiments, the disclosure relates to transgenic sheep or goats comprising nucleic acids that express Cas9 systems disclosed herein and nucleic acids that express a recombinant protein in their milk.

In certain embodiments, the disclosure contemplates a transgenic chicken comprising nucleic acids that express Cas9 systems disclosed herein and nucleic acids that express a recombinant protein in their eggs, e.g., whites.

Gene Therapies

In certain embodiments, the disclosure relates to methods of treating or preventing diseases, conditions, or infections comprising administering an effective amount recombinant vectors to a subject that encode Cas9 and nucleic acid complexes disclosed herein, to a subject in need thereof.

In certain embodiments, the disclosure relates to methods of treating or preventing viral infections or other pathogenic infection comprising administering an effective amount of vector configured to express a Cas9-nucleic acid complex that targets viral or pathogenic nucleic acids.

In certain embodiment, the disclosure contemplates administration in combination with other therapeutic agents, anti-pathogenic agents, anti-viral agents, anti-bacterial agents or vaccines. In certain embodiments, the antiviral agent(s) are selected from abacavir, acyclovir, acyclovir, adefovir, amantadine, amprenavir, ampligen, arbidol, atazanavir, atripla, boceprevir, cidofovir, combivir, complera, darunavir, delavirdine, didanosine, docosanol, dolutegravir, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, stavudine, stribild, tenofovir, tenofovir disoproxil, tenofovir alafenamide fumarate (TAF), tipranavir, trifluridine, trizivir, tromantadine, truvada, valaciclovir, valganciclovir, vicriviroc, vidarabine, viramidine, zalcitabine, zanamivir, or zidovudine, and combinations thereof.

In certain embodiments, the disclosure contemplates treating and/or preventing viral infections by targeting both RNA and DNA viruses, e.g., targeting the genome of and/or transcript of RNA viruses or the viral transcript of DNA viruses. In some embodiments, the virus is or a subject is diagnosed with influenza A virus including subtype H1N1, influenza B virus, influenza C virus, rotavirus A, rotavirus B, rotavirus C, rotavirus D, rotavirus E, SARS coronavirus, human adenovirus types (HAdV-1 to 55), human papillomavirus (HPV) Types 16, 18, 31, 33, 35, 39, 45, 51, 52, 56, 58, 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, respiratory syncytial virus, rinderpest virus, California encephalitis virus, hantavirus, rabies virus, ebola virus, marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, Kaposi's sarcoma-associated herpesvirus, hepatitis A (HAV), hepatitis B (HBV), hepatitis C (HCV), hepatitis D (HDV), hepatitis E (HEV), human immunodeficiency virus (HIV), The Human T-lymphotropic virus Type I (HTLV-1), Friend spleen focus-forming virus (SFFV) or Xenotropic MuLV-Related Virus (XMRV).

In certain embodiments, the disclosure contemplates targeting multiple sites in the RNA genome of an RNA virus, or RNA transcript of a DNA virus for the purpose of preventing development of resistance by viruses.

In certain embodiments, the disclosure contemplates Cas9 and a cocktail of gRNAs targeting different viruses could be used as a "one-shot" therapeutic.

In certain embodiments, the disclosure contemplates using the Cas9 system disclosed herein to improve the ability of a subject to process and respond to a vaccine by administering a cloning vector disclosed herein in combination with a vaccine wherein a Cac9 nucleic acid complex is configuring with gRNA to target mRNA expression of IL-10 and/or other anti-inflammatory cytokines, and/or targeting mRNA expression PD-1/PD-L1.

In certain embodiments, the disclosure contemplates using the Cas9 system for treating cancer. For example, gRNA may be configured to target mRNA or microRNA that is overexpressed in cancer cells or control the expression of oncogenes. Some cancers suppress the RNAi machinery, but would likely be unable to do the same with Cas9 systems disclosed herein. Targeting mRNA with Cas9 systems disclosed herein typically results in decreased expression of the gene product, while targeting microRNA typically results in increased expression of gene product.

In certain embodiments, the disclosure relates to treating or preventing cancer comprising administering a vector that expresses Cas9 and guided nucleic acid complexes disclosed herein wherein the cancer is selected from brain, lung, cervical, ovarian, colon, breast, gastric, skin, ovarian, pancreatic, prostate, neck, and renal cancer.

In certain embodiments, the disclosure relates to methods of treating cancer comprising administering an effective amount of cloning vector disclosed herein that is configure to express Cas9 and a guided nucleic acid complex that targets mRNA or microRNA associated with an oncogene. In certain embodiments, target mRNA or microRNA are associated with K-ras, baculoviral IAP repeat containing 3, baculoviral IAP repeat containing 7, tumor protein p53, tumor protein p53 regulated apoptosis inducing protein 1, tumor protein p73, vascular endothelial growth factor A, v-akt murine thymoma viral oncogene, phosphatase and tensin, B-cell CLL/lymphoma 2, signal transducer and activator of transcription 3, epidermal growth factor receptor, v-erb-b2 avian erythroblastic leukemia viral oncogene, tumor necrosis factor, tumor necrosis factor superfamily member 14, nuclear factor of kappa light polypeptide gene enhancer in B-cells 1, catenin (cadherin-associated protein) beta 1, transforming growth factor beta 1, cyclin-dependent kinase inhibitor 1A, caspase 3, caspase 8, caspase 9, telomerase reverse transcriptase, hypoxia inducible factor 1 alpha subunit, ATP-binding cassette sub-family B, cyclin-dependent kinase inhibitor 2A, v-myc avian myelocytomatosis viral oncogene, insulin-like growth factor 1, matrix metallopeptidase 7, matrix metallopeptidase 9, interleukin 8, cyclin B1, cyclin D1, chemokine (C-C motif) ligand 2, cadherin 1, E-cadherin, mitogen-activated protein kinase 1, interferon gamma, tumor necrosis factor (ligand) superfamily member 10, microtubule-associated protein tau, X-linked inhibitor of apoptosis, Fas cell surface death receptor, retinoblastoma 1, Bcl-2, BCL2-like 2, BCL2-associated X protein, BCL2-antagonist/killer 1, caveolin 1, caveolae protein, mechanistic target of rapamycin, v-kit Hardy-Zuckerman 4 feline sarcoma viral oncogene, mitogen-activated protein kinase 14, adenomatous polyposis coli, aurora kinase B, cyclin-dependent kinase 1, cyclin-dependent kinase 4, cyclin-dependent kinase inhibitor 1B, heme oxygenase (decycling) 1, notch 1, notch 2, secreted phosphoprotein 1, mitogen-activated protein kinase 3, runt-related transcription factor 1, forkhead box 03, forkhead box P3, jun proto-oncogene, poly (ADP-ribose) polymerase 1, Harvey rat sarcoma viral oncogene, glycogen synthase kinase 3 beta, nitric oxide synthase 2, ras-related C3 botulinum toxin substrate 1, E1A binding protein p300, Fas ligand, ATP-binding cassette G2, CREB binding protein, protein kinase C alpha, fms-related tyrosine kinase 3, fibroblast growth factor 2, O-6-methylguanine-DNA methyltransferase, checkpoint kinase 2, diablo IAP-binding mitochondrial protein, parkinson protein 2, polo-like kinase 1, transcription factor 7-like 2, E2F transcription factor 1, high mobility group box 1, promyelocytic leukemia, BCL2-like 1, urokinase plasminogen activator, tumor necrosis factor superfamily member 1A, proliferating cell nuclear antigen, urokinase receptor plasminogen activator, APEX nuclease, lectin galactoside-binding soluble 3, myeloid cell leukemia sequence 1, cannabinoid receptor 1, gap junction protein alpha 1, antigen identified by monoclonal antibody Ki-67, calcium-sensing receptor, thrombospondin 1, POU class 5 homeobox 1, hepatocyte nuclear factor 4 alpha, transforming growth factor beta receptor II, platelet-derived growth factor receptor alpha polypeptide, runt-related transcription factor 2, vascular endothelial growth factor C, early growth response 1, angiopoietin 2, BMI1 polycomb ring finger oncogen, parkinson protein 7, v-myc avian myelocytomatosis viral oncogene neuroblastoma, v-akt murine thymoma viral oncogene homolog 2, H2A histone family member X, tuberous sclerosis 2, exportin 1, peptidylprolyl cis/trans isomerase NIMA-interacting 1, dickkopf WNT signaling pathway inhibitor 1, beclin 1, platelet-derived growth factor beta polypeptide, cortactin, colony stimulating factor 2, fused in sarcoma, ets variant 6, GATA binding protein 1, RAN member RAS oncogene, Kruppel-like factor 4, Kruppel-like factor 5, lymphoid enhancer-binding factor 1, histone deacetylase 6, stathmin 1, folate hydrolase 1, RAS p21 protein activator 1, serine/arginine-rich splicing factor 1, glypican 3, cell adhesion molecule 1, wingless-type MMTV integration site family, member 1, platelet-derived growth factor alpha polypeptide, junction plakoglobin, protein arginine methyltransferase 1, interleukin 11, retinoblastoma-like 2, E2F transcription factor 3, tumor-associated calcium signal transducer 2, XIAP associated factor 1, microtubule-associated protein 4, sirtuin 6, Wilms tumor 1 associated protein, or combinations thereof.

In certain embodiments, the disclosure relates to methods of treating cancer comprising administering an effective amount of cloning vector disclosed herein that is configure to express Cas9 and a guided nucleic acid complex that targets mRNA or microRNA associated with growth factors, or mitogens, e.g. c-Sis, to a subject in need thereof. In certain embodiments, the cancer is selected from or the subject is diagnosed with glioblastoma, fibrosarcoma, osteosarcoma, breast carcinoma, or melanoma.

In certain embodiments, the disclosure relates to methods of treating cancer comprising administering an effective amount of cloning vector disclosed herein that is configure to express Cas9 and a guided nucleic acid complex that targets mRNA or microRNA associated with receptor tyrosine kinases, e.g., epidermal growth factor receptor (EGFR), platelet-derived growth factor receptor (PDGFR), and vascular endothelial growth factor receptor (VEGFR), HER2/neu, to a subject in need thereof. In certain embodiments, the cancer is selected from or the subject is diagnosed with breast cancer, gastrointestinal stromal tumors, non-small-cell lung cancer, or pancreatic cancer.

In certain embodiments, the disclosure relates to methods of treating cancer comprising administering an effective amount of cloning vector disclosed herein that is configure to express Cas9 and a guided nucleic acid complex that targets mRNA or microRNA associated with cytoplasmic tyrosine kinases, e.g., Src-family, Syk-ZAP-70 family, and BTK family of tyrosine kinases, Abl, to a subject in need thereof. In certain embodiments, the cancer is selected from or the subject is diagnosed with colorectal, breast cancers, melanomas, ovarian cancers, gastric cancers, head and neck cancers, pancreatice cancer, lung cancer, brain cancers, or blood cancers.

In certain embodiments, the disclosure relates to methods of treating cancer comprising administering an effective amount of cloning vector disclosed herein that is configure to express Cas9 and a guided nucleic acid complex that targets mRNA or microRNA associated with cytoplasmic Serine/threonine kinases and their regulatory subunits, e.g., Raf kinase, and cyclin-dependent kinases, to a subject in need thereof. In certain embodiments, the cancer is selected from or the subject is diagnosed with malignant melanoma, papillary thyroid cancer, colorectal cancer, or ovarian cancer.

In certain embodiments, the disclosure relates to methods of treating cancer comprising administering an effective amount of cloning vector disclosed herein that is configure to express Cas9 and a guided nucleic acid complex that targets mRNA or microRNA associated with regulatory GTPases, e.g., Ras protein, to a subject in need thereof. In certain embodiments, the cancer is selected from or the subject is diagnosed with adenocarcinomas of the pancreas and colon, thyroid tumors, or myeloid leukemia In certain embodiments, the disclosure relates to methods of treating cancer comprising administering an effective amount of cloning vector disclosed herein that is configure to express Cas9 and a guided nucleic acid complex that targets mRNA or microRNA associated with transcription factors, e.g., myc, to a subject in need thereof. In certain embodiments, the cancer is selected from or the subject is diagnosed with malignant T-cell lymphomas and acute myeloid leukemias, breast cancer, pancreatic cancer, retinoblastoma, and small cell lung cancer In certain embodiments, the disclosure contemplates targeting multiple sites in a cancer oncogene, or any gene desirable to knockdown in cancer cells for the purpose of preventing the development of resistance in the cancer cells.

In certain embodiments, the disclosure relates to methods of treating cancer comprising administering an effective amount of cloning vector disclosed herein that is configure to express Cas9 and a guided nucleic acid complex in combination with chemotherapies. In certain embodiments, the chemotherapy includes that administration of In certain embodiments, the disclosure contemplates using the Cas9 system disclosed herein to improve the ability of a subject to process and respond to chemotherapies by administering a cloning vector disclosed herein in combination with a chemotherapies wherein a Cas9 nucleic acid complex is configuring with gRNA to target mRNA expression of IL-10 and/or other anti-inflammatory cytokines, and/or targeting mRNA expression PD-1/PD-L1.

EXAMPLES

Bacteria and Macrophage Infections

*Francisella novicida* U112 and mutant strains were constructed by allelic replacement using primers. Mutant strains grew similarly to wild-type in broth. Murine bone marrow-derived macrophages were prepared from wild-type and TLR2-/- C57BL/6 mice and cultured. Macrophages were infected with bacteria at a multiplicity of infection (MOI) of 20:1 bacteria per macrophage. The concentration of IL-6 in culture supernatants was quantified by ELISA (BD Biosciences). For stimulation with bacterial membrane protein fractions, cells were washed gently and media containing membrane protein fractions at a relative MOI of 20:1 were added and IL-6 was quantified.

Bacterial Cas9 (FTN_0757) is in a CRISPR-CAS Locus

Figure 1B:
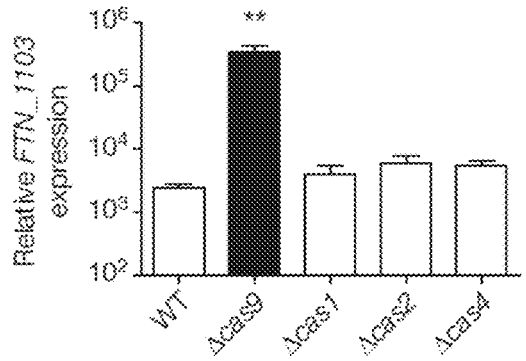
Figure 1C:
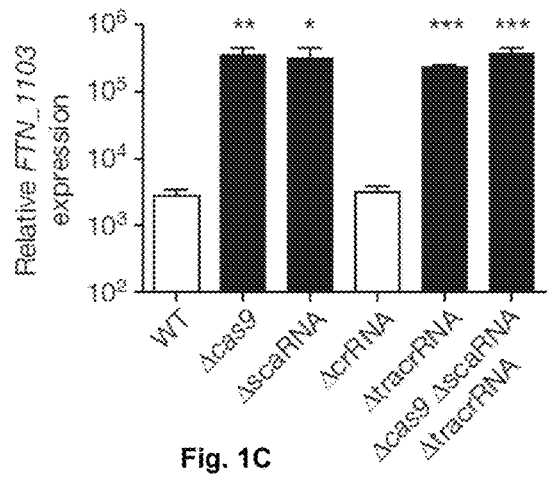

Whether FTN_0757 requires the canonical CRISPR-CAS system to repress expression of FTN_1103 (bacterial lipoprotein, BLP) was tested (FIG. 1a). Deletion of cas9, but not other CAS genes, led to 100-fold increased levels of FTN_1103 transcript (FIG. 1b). Because Cas9 degrades DNA targeted by crRNAs, whether the crRNA array or the tracrRNA were necessary for repression of FTN_1103 was tested. Deletion of the crRNA array did not alter FTN_1103 transcript levels (FIG. 1c); however, deletion of the tracrRNA resulted in increased FTN_1103 transcript, similar to the cas9 mutant (FIG. 1c). Additionally, deletion of the scaRNA resulted in increased FTN_1103 transcript, indicating that it is also important for FTN_1103 repression. Complementation of the cas9, tracrRNA, and scaRNA mutants restored FTN_1103 expression to near wild-type levels, and levels of FTN_1103 transcript in the mutants correlated with an increase in protein production. Furthermore, a triple mutant lacking cas9, tracrRNA, and scaRNA expressed similar levels of FTN_1103 mRNA as the single mutants, providing genetic evidence that these components may work together within the same regulatory pathway to repress expression of FTN_1103.

Mutant Cas9, tracrRNA, and scaRNA and Motifs in Cas9 are Involved in the Repression of BLP mRNA FTN_1103

Figure 2A:
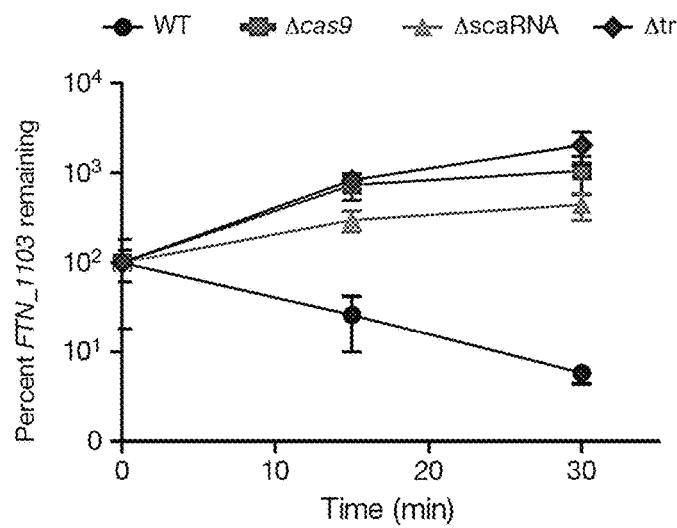
FIG. 2A-G shows data indicating Cas9, tracrRNA, and scaRNA associate and mediate FTN_1103 degradation.
Figure 2B:
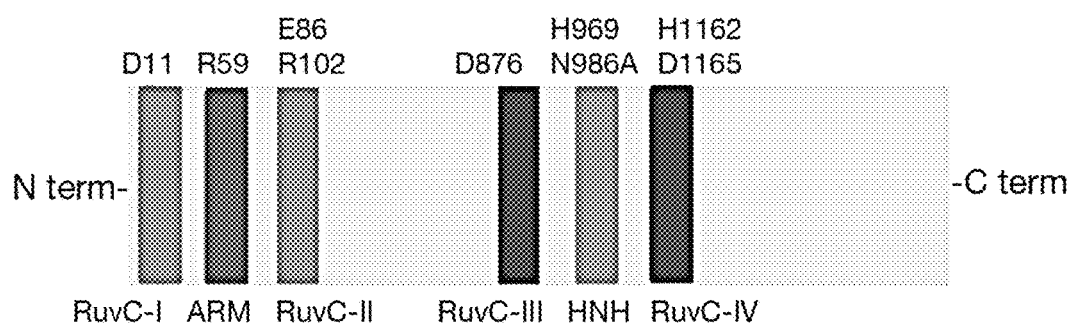

Cas9 proteins contain four RuvC endonuclease domains (RuvC-I through RuvC-IV), as well as an HNH endonuclease domain (FIG. 6). While RuvC-I and the HNH are known to be necessary for degradation of target DNA, the functions of the other domains were unknown. In order to determine which of these domains is necessary for the repression of FTN_1103 mRNA, point mutant strains lacking conserved residues were constructed in each domain (FIG. 2a). Surprisingly, RuvC-I and HNH catalytic mutants maintained wild-type ability to repress FTN_1103, demonstrating that Cas9-mediated repression of FTN_1103 does not require these domains, and differentiating this process from the targeting of DNA. While RuvC-II point mutants also had wild-type levels of FTN_1103 transcript (FIG. 2b). Additionally, no role for distinct RNase proteins in FTN_1103 repression was found, supporting the hypothesis that Cas9 is capable of mediating the degradation of targeted mRNA. Thus, the ability to repress FTN_1103 requires two Cas9 endonuclease domains distinct from those that mediate target DNA degradation.

Figure 2C:
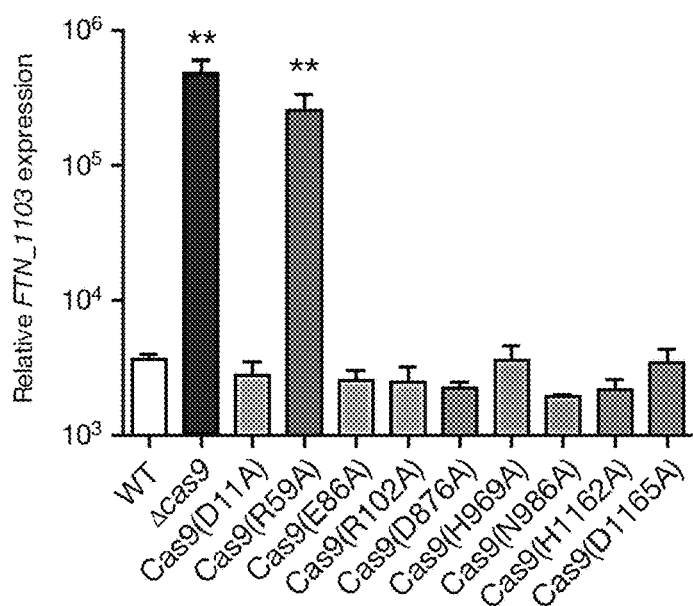

Since targeting by Cas9 can lead to degradation of DNA, whether Cas9, tracrRNA, and the scaRNA were involved in the silencing of FTN_1103 mRNA was next analyzed through degradation. Following treatment with rifampin to block transcription and prevent production of mRNA, FTN_1103 transcript was rapidly depleted in wild-type cells (FIG. 2c). In contrast, FTN_1103 transcript was not degraded in mutants lacking Cas9, tracrRNA, or the scaRNA (FIG. 2c). Therefore, each of these three CRISPR-CAS system components is involved in the repression of FTN_1103 mRNA by promoting its degradation.

Figure 2D:
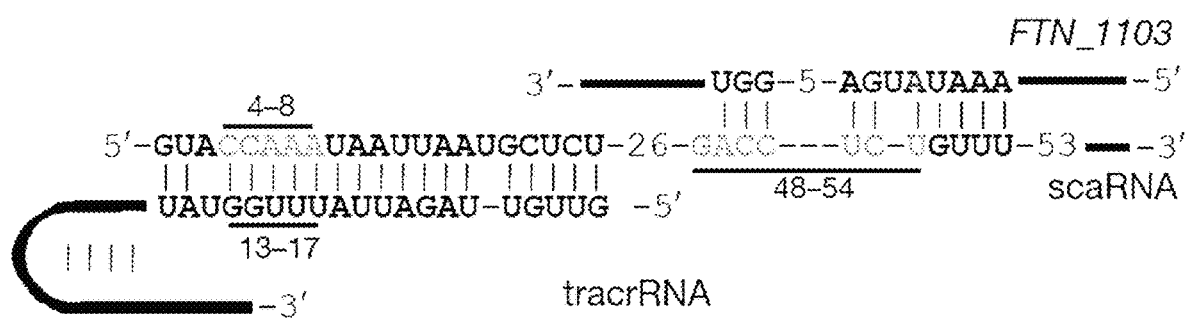
Figure 2E:
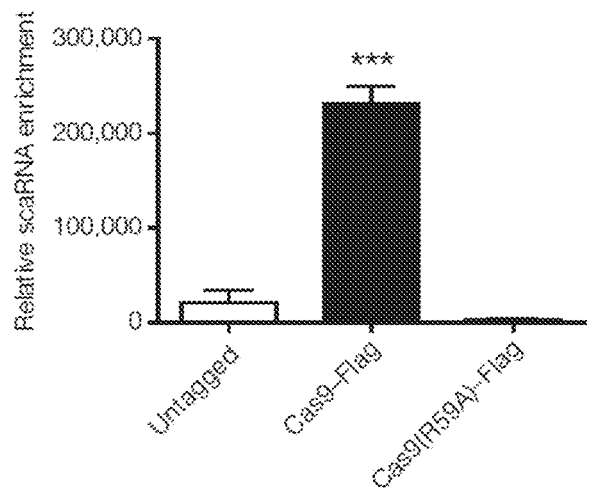
Figure 2F:
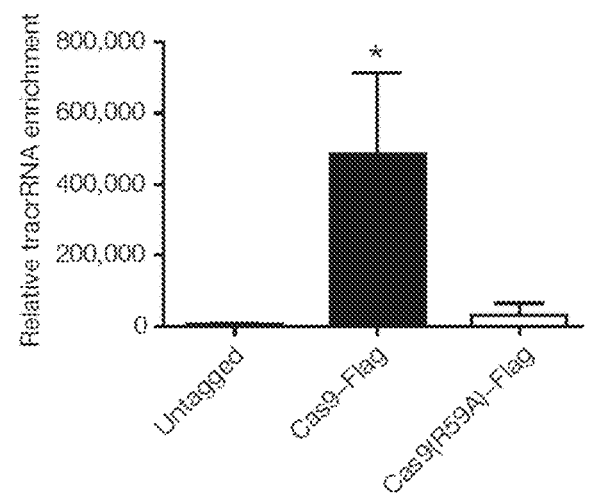

Cas9 contains a previously uncharacterized, conserved, arginine-rich motif (ARM)(FIG. 6). Since Cas9 and two sRNAs (tracrRNA and scaRNA) were involved in the repression and degradation of FTN_1103 mRNA, this putative RNA binding region might be important for Cas9 function. Indeed, a point mutation in the ARM completely abrogated the ability of Cas9 to repress FTN_1103 expression (FIG. 2b), implicating this region in the ability of Cas9 to interact with RNAs. The sequences of the tracrRNA and scaRNA were analyzed and it was determined that the tracrRNA could hybridize to a degenerate repeat region in the scaRNA (FIG. 2d), similar to the interaction between the tracrRNA and the repeat region of a crRNA, which is necessary for targeting DNA. Analysis also indicated that a distinct region of the tracrRNA could hybridize to a region of the FTN_1103 transcript encompassing the start codon and ribosomal binding site (RBS)(FIG. 2d). To determine whether Cas9 and the RNAs associated together, we immunoprecipitated Cas9 from a strain expressing a FLAGtagged version of this protein. tracrRNA, scaRNA, and FTN_1103 mRNA were significantly enriched in association with Cas9 (FIG. 2e, f). However, this association was abrogated in the Cas9 ARM mutant (R59A), implicating this RNA-binding domain of Cas9 in the interaction with these RNAs.

Figure 2G:
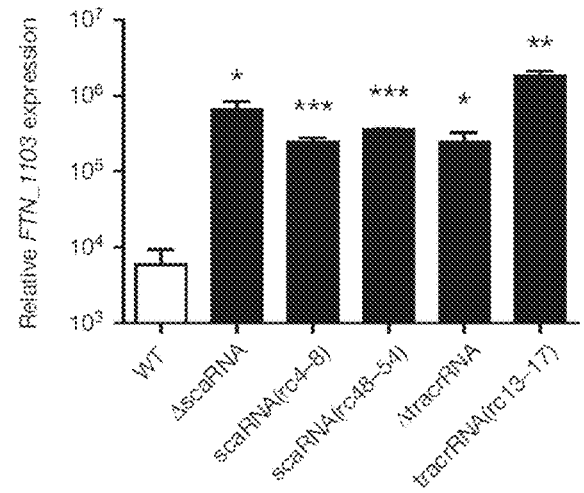

In order to further determine whether the predicted interactions between these components were required for formation of the complex, reverse complement mutations were generated in the tracrRNA region (bases 13-17) predicted to interact with the scaRNA, as well as the scaRNA regions predicted to interact with the tracrRNA (bases 4-8) or $FTN_{1103}$ mRNA (bases 48-54). All three mutations resulted in a complete inability to repress $FTN_{1103}$ transcript (FIG. 2g). Additionally, the mutations indicated to disrupt the interaction between scaRNA and tracrRNA significantly dampened the ability of either small RNA to associate with Cas9. Thus, the sequence specific association of Cas9, tracrRNA, and scaRNA is important for the targeting and repression transcript.

```
Cas9 amino acid sequence
                                (SEQ ID NO: 1)
MNFKILPIAIDLGVKNTGVFSAFYQKGTSLERLDNKNGKVYELSKDSYTL
LMNNRTARRHQRRGIDRKQLVKRLFKLIWTEQLNLEWDKDTQQAISFLFN
RRGFSFITDGYSPEYLNIVPEQVKAILMDIFDDYNGEDDLDSYLKLATEQ
ESKISEIYNKLMQKILEFKLMKLCTDIKDDKVSTKTLKEITSYEFELLAD
YLANYSESLKTQKFSYTDKQGNLKELSYYHHDKYNIQEFLKRHATINDRI
LDTLLTDDLDIWNFNFEKFDFDKNEEKLQNQEDKDHIQAHLHHFVFAVNK
IKSEMASGGRHRSQYFQEITNVLDENNHQEGYLKNFCENLHNKKYSNLSV
KNLVNLIGNLSNLELKPLRKYFNDKIHAKADHWDEQKFTETYCHWILGEW
RVGVKDQDKKDGAKYSYKDLCNELKQKVTKAGLVDFLLELDPCRTIPPYL
DNNNRKPPKCQSLILNPKFLDNQYPNWQQYLQELKKLQSIQNYLDSFETD
LKVLKSSKDQPYFVEYKSSNQQIASGQRDYKDLDARILQFIFDRVKASDE
LLLNEIYFQAKKLKQKASSELEKLESSKKLDEVIANSQLSQILKSQHTNG
IFEQGTFLHLVCKYYKQRQRARDSRLYIMPEYRYDKKLHKYNNTGRFDDD
NQLLTYCNHKPRQKRYQLLNDLAGVLQVSPNFLKDKIGSDDDLFISKWVE
HIRGFKKACEDSLKIQKDNRGLLNHKINIARNTKGKCEKEIFNLICKIEG
SEDKKGNYKHGLAYELGVLLFGEPNEASKPEFDRKIKKFNSIYSFAQIQQ
IAFAERKGNANTCAVCSADNAHRMQQIKITEPVEDNKDKIILSAKAQRLP
AIPTRIVDGAVKKMATILAKNIVDDNWQNIKQVLSAKHQLHIPIITESNA
FEFEPALADVKGKSLKDRRKKALERISPENIFKDKNNRIKEFAKGISAYS
GANLTDGDFDGAKEELDHIIPRSHKKYGTLNDEANLICVTRGDNKNKGNR
IFCLRDLADNYKLKQFETTDDLEIEKKIADTIWDANKKDFKFGNYRSFIN
LTPQEQKAFRHALFLADENPIKQAVIRAINNRNRTFVNGTQRYFAEVLAN
NIYLRAKKENLNTDKISFDYFGIPTIGNGRGIAEIRQLYEKVDSDIQAYA
KGDKPQASYSHLIDAMLAFCIAADEHRNDGSIGLEIDKNYSLYPLDKNTG
EVFTKDIFSQIKITDNEFSDKKLVRKKAIEGFNTHRQMTRDGIYAENYLP
ILIHKELNEVRKGYTWKNSEEIKIFKGKKYDIQQLNNLVYCLKFVDKPIS
IDIQISTLEELRNILTTNNIAATALYYYINLKTQKLHEYYIENYNTALGY
KKYSKEMEFLRSLAYRSERVKIKSIDDVKQVLDKDSNFIIGKITLPFKKE
WQRLYREWQNTTIKDDYEFLKSFFNVKSITKLHKKVRKDFSLPISTNEGK
FLVKRKTWDNNFIYQILNDSDSRADGTKPFIPAFDISKNEIVEAIIDSFT
SKNIFWLPKNIELQKVDNKNIFAIDTSKWFEVETPSDLRDIGIATIQYKI
DNNSRPKVRVKLDYVIDDDSKINYFMNHSLLKSRYPDKVLEILKQSTIIE
FESSGFNKTIKEMLGMKLAGIYNETSNN Cas9 Nucleotide
                                (SEQ ID NO: 2)
ATGAATTTCAAAATATTGCCAATAGCAATAGATTTAGGTGTTAAAAATAC
TGGTGTCTTTAGCGCATTTTATCAAAAAGGAACTTCTCTTGAGAGATTGG
ATAATAAAAATGGCAAAGTATATGAACTATCAAAAGATTCTTATACTTTA
TTGATGAATAATAGAACAGCAAGAAGACATCAAAGAAGAGGGATAGATAG
AAAGCAGCTAGTCAAAAGGCTCTTTAAGCTTATTTGGACAGAGCAGCTAA
ATTTAGAGTGGGATAAAGACACTCAACAAGCAATTAGCTTTTTATTTAAT
CGTAGAGGTTTTAGTTTTATTACTGATGGTTATTCGCCTGAATATTTAAA
TATTGTTCCAGAGCAAGTAAAAGCGATACTTATGGATATATTTGATGATT
ACAACGGTGAAGATGATTTAGACAGTTATTTAAAATTAGCTACTGAGCAA
GAAAGCAAAATTTCTGAAATTTATAACAAGCTAATGCAAAAAATATTAGA
GTTTAAATTAATGAAATTATGTACTGATATTAAGGATGATAAAGTAAGTA
CTAAAACGCTTAAAGAAATCACAAGCTATGAATTTGAGTTATTAGCTGAT
TATTTAGCAAACTATAGCGAGAGTTTAAAAACACAAAAATTTAGTTATAC
AGATAAACAAGGTAATTTAAAAGAGCTAAGCTACTATCATCATGATAAAT
ATAATATTCAAGAATTTCTAAAGCGACATGCTACTATAAATGATCGAATT
TTAGATACTCTTTTAACTGATGATTTAGATATTTGGAATTTTAATTTTGA
GAAATTTGATTTTGATAAGAATGAAGAAAAGCTTCAGAATCAGGAAGATA
AAGATCATATACAAGCGCATTTACATCATTTTGTTTTTGCAGTAAATAAA
ATAAAAAGTGAAATGGCAAGTGGTGGTCGTCATCGTAGCCAATATTTTCA
AGAGATAACAAATGTGCTAGATGAAAATAATCATCAAGAGGGATATCTCA
AGAATTTCTGTGAAAATTTGCATAATAAAAAATATTCAAATTTAAGTGTT
AAAAATTTAGTTAATCTAATTGGTAACCTAAGTAATTTAGAGCTAAAACC
GCTAAGAAAATATTTTAATGACAAAATTCACGCAAAAGCTGATCATTGGG
ATGAGCAAAAGTTTACAGAAACTTATTGCCACTGGATATTAGGAGAGTGG
CGAGTAGGTGTCAAAGATCAAGATAAGAAAGATGGCGCTAAATATAGTTA
TAAAGATCTGTGTAATGAATTAAAACAAAAAGTTACTAAGGCTGGTTTGG
TAGATTTTTTATTAGAGTTAGATCCATGTAGAACTATACCACCATATCTG
GATAACAATAACCGTAAACCACCAAAATGTCAAAGTTTGATTTTAAATCC
GAAGTTTTTAGATAATCAATATCCAAACTGGCAACAATATTTACAAGAAT
TAAAGAAACTACAAAGTATTCAAAATTATTTAGACAGTTTTGAAACTGAT
TTAAAAGTCTTAAAGTCAAGTAAAGATCAACCATATTTTGTTGAATACAA
GAGTTCAAATCAGCAAATAGCAAGTGGTCAAAGAGATTATAAAGATTTAG
ATGCTCGAATATTACAGTTTATATTTGATAGGGTAAAAGCTAGTGATGAG
```

-continued

Figure 3A:
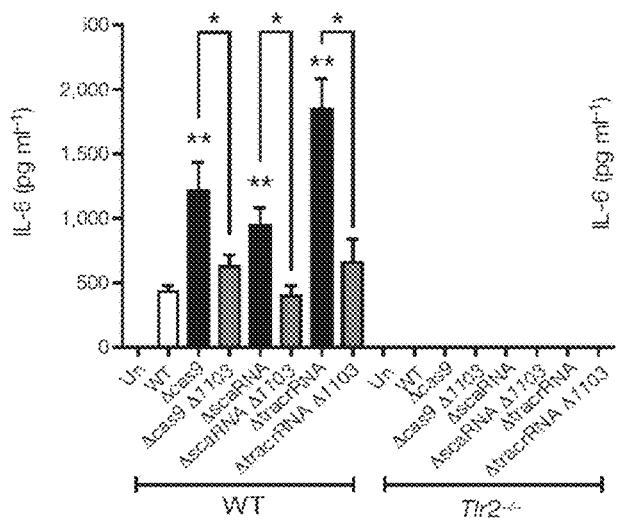
FIG. 3A shows data indicating Cas9, tracrRNA, and scaRNA facilitate evasion of TLR2 signaling by temporal repression of FTN_1103. (IL-6 secretion from wild-type (WT) and TLR2-/- bone marrow derived macrophages (BMDM) unstimulated (Un) or stimulated with membrane protein preparations at a relative MOI of 20:1 for 5 hours from wild-type (WT), Δcas9, ΔscaRNA, and ΔtracrRNA strains, or with double deletion strains also lacking FTN_1103 (Δcas9/1103, ΔscaRNA/1103, and ΔtracrRNA/1103) (n=3).
Figure 3B:
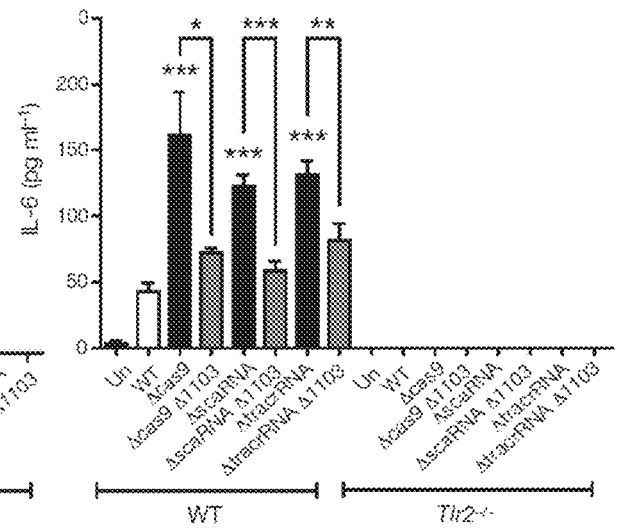
FIG. 3B shows IL-6 secretion from WT or TLR2-/- BMDM that were uninfected, or infected with wild-type (WT), Δcas9, ΔscaRNA, and ΔtracrRNA strains, or with double deletion strains Δcas9/1103, ΔscaRNA/1103, and ΔtracrRNA/1103 at an MOI of 20:1 for 5 hours (n=6). Relative expression levels of FIG. 3C shows FTN_1103 as described above.
Figure 3C:
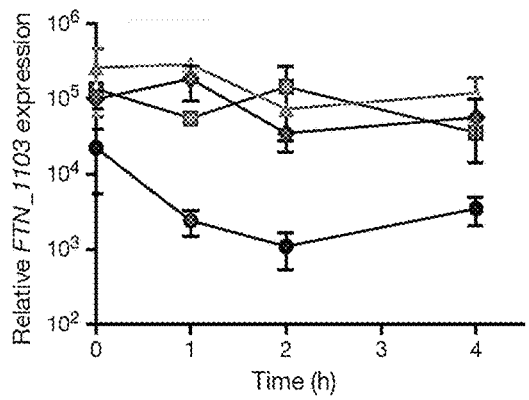
FIG. 3D shows cas9 as described above.
FIG. 3E shows scaRNA as described above.
FIG. 3F shows tracrRNA over the course of infection of BMDM by WT (black circles), Δcas9 (blue squares), ΔscaRNA (yellow triangles), and ΔtracrRNA (green diamonds) strains (n=3, points represent the mean and bars the standard deviation, p≤0.05 for all mutants compared to wildtype).
Figure 3D:
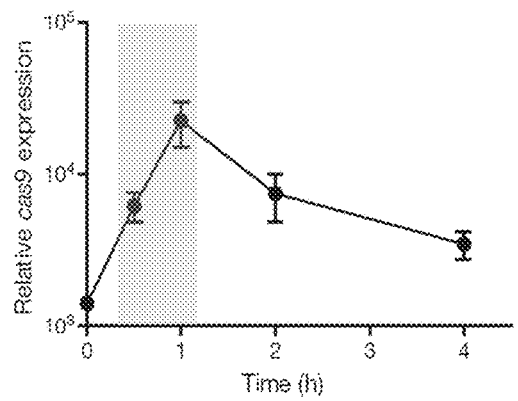
Figure 3E:
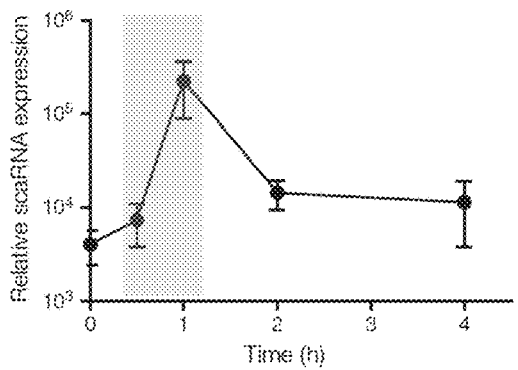
Figure 3F:
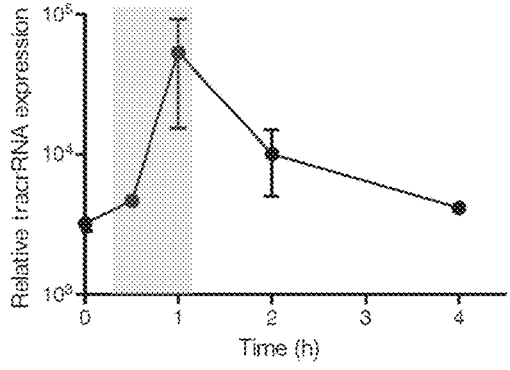
Figure 4A:
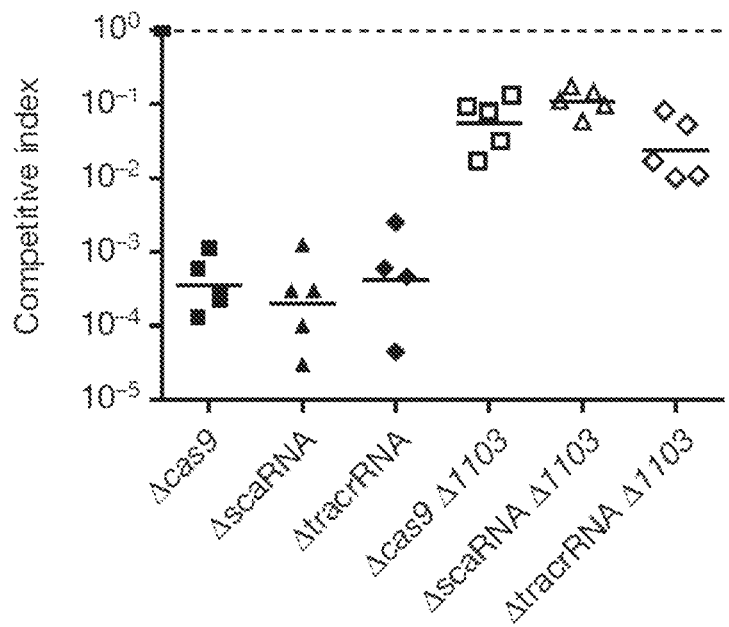
FIG. 4A shows data indicating Cas9, tracrRNA, and scaRNA are important for virulence. Competitive indices of wild-type and the indicated mutant or double mutant strains from murine spleens, 48 hours post-infection. Bars represent the geometric mean.
Figure 4B:
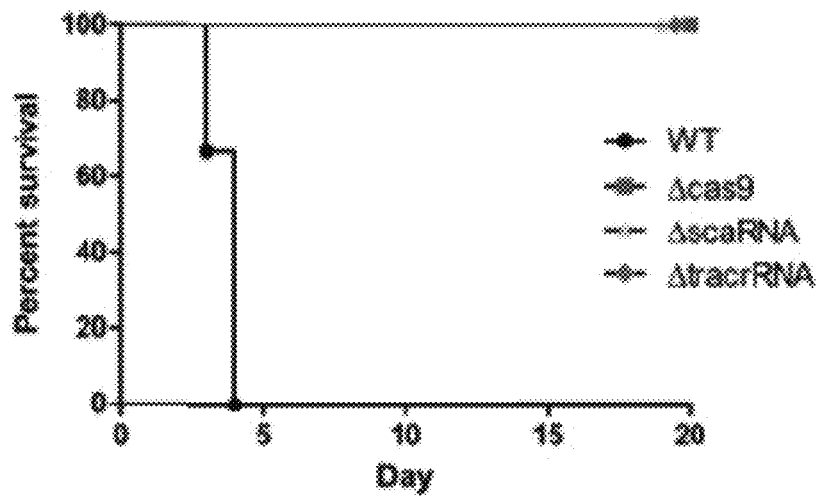
FIG. 4B shows mice were infected with $10^7$ cfu of either wild-type, Δcas9, ΔscaRNA, or ΔtracrRNA strains, and survival monitored over time.
Figure 4C:
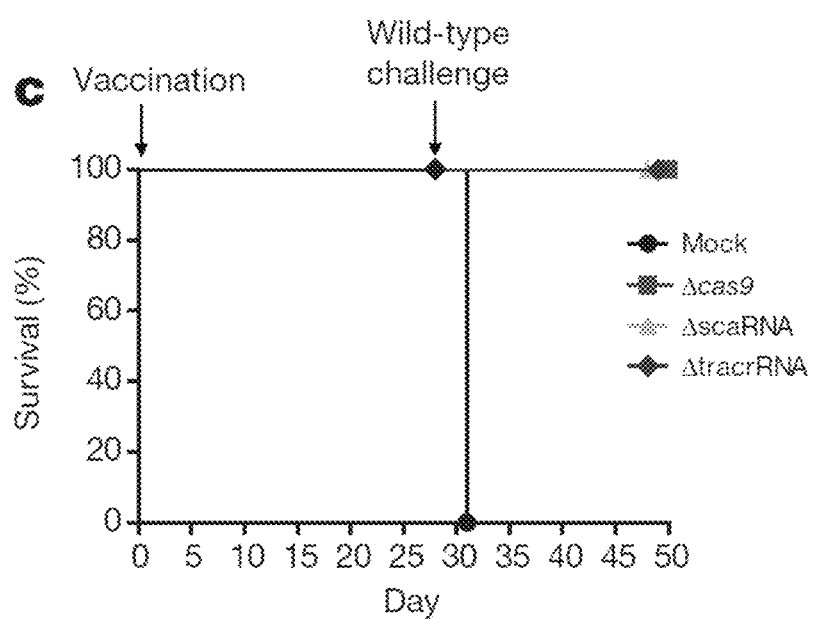
FIG. 4C shows mice were vaccinated with $10^4$ cfu of either Δcas9, ΔscaRNA, or ΔtracrRNA strains, or PBS. Twenty-eight days later, mice were challenged with $10^7$ cfu wild-type.

```
TTGCTTTTGAATGAGATTTATTTTCAGGCTAAAAAACTTAAACAAAAAGC
TAGCTCTGAGTTAGAAAAACTCGAGTCGAGCAAAAAGCTAGATGAAGTTA
TAGCAAATAGTCAACTATCACAGATACTAAAGTCTCAACATACAAATGGT
ATTTTTGAACAGGGTACTTTTTTGCATTTGGTTTGTAAATATTATAAACA
AAGACAAAGAGCGAGAGACTCTAGGCTATATATTATGCCTGAATATCGTT

ATGATAAAAAACTACATAAATATAACAATACAGGCAGGTTTGATGATGAT

AATCAGCTGCTAACATATTGTAATCATAAGCCAAGACAAAAAAGATACCA

ATTGTTAAATGATTTAGCTGGGGTGTTGCAGGTATCACCTAATTTTTTGA

AAGATAAAATTGGTTCTGATGATGATCTATTTATTAGCAAATGGTTGGTA

GAGCATATTAGAGGATTTAAAAAAGCTTGTGAAGATAGTTTAAAAAATACA

AAAAGACAATAGAGGATTATTAAATCATAAAATAAATATAGCTAGGAATA

CAAAAGGCAAATGTGAAAAAGAAATATTTAATTTAATATGTAAAATAGAA

GGTTCAGAAGATAAAAAAGGTAATTACAAGCATGGTTTAGCTTACGAATT

AGGAGTACTTTTATTTGGTGAACCTAATGAAGCTAGTAAACCTGAGTTCG

ATAGAAAAATTAAAAAATTTAACTCAATATACAGTTTTGCACAGATTCAA

CAAATTGCTTTTGCAGAGCGTAAAGGCAATGCTAACACTTGTGCAGTTTG

TAGTGCTGATAATGCTCATAGAATGCAACAAATTAAGATCACTGAGCCTG

TAGAGGACAATAAAGATAGATAATCTTAAGTGCCAAAGCTCAGAGACTAC

CAGCGATTCCAACTAGAATAGTTGACGGTGCGGTTAAGAAAATGGCAACT

ATATTAGCTAAAAATATAGTTGATGATAATTGGCAGAATATCAAACAAGT

TTTATCAGCAAAACATCAGTTACATATACCTATTATCACAGAATCAAATG

CTTTTGAGTTTGAACCAGCATTAGCTGATGTAAAAGGTAAGAGCCTAAAA

GATAGGAGAAAAAAAGCATTAGAGAGAATAAGTCCTGAAAATATATTCAA

GGATAAAAACAATAGAATAAAAGAATTTGCTAAAGGTATATCAGCATATA

GTGGTGCTAATTTAACTGATGGCGATTTTGATGGTGCAAAAGAAGAATTA

GATCATATAATACCTCGTTCACATAAAAAATACGGTACTCTAAATGATGA

AGCAAATCTAATTTGTGTAACTCGTGGTGATAATAAAAATAAAGGTAATA

GAATTTTCTGCCTACGTGATCTTGCAGATAACTATAAACTAAAACAGTTT

GAGACAACTGATGATTTAGAAATTGAAAAGAAGATAGCTGATACAATCTG

GGATGCTAACAAGAAAGATTTTAAATTTGGTAATTATCGTAGTTTTATTA

ACCTAACACCACAAGAGCAGAAAGCATTTCGTCACGCGCTATTTCTGGCT

GATGAAAATCCTATCAAACAAGCAGTCATAAGAGCGATAAATAATCGTAA

TCGTACATTTGTAAATGGCACTCAACGCTATTTTGCAGAAGTACTGGCAA

ACAATATCTATCTAAGGGCTAAAAAAGAAAATCTAAATACAGATAAAATT

TCATTTGATTATTTTGGTATTCCAACTATAGGTAATGGTAGAGGTATTGC

TGAAATCCGTCAACTTTATGAAAAAGTTGATAGTGATATACAAGCTTATG

CAAAAGGTGATAAACCTCAAGCTAGCTACTCTCACCTAATAGATGCGATG

CTGGCTTTTTGTATTGCTGCTGATGAACACAGAAATGATGGAAGTATAGG

TCTAGAAATCGATAAAAATTATAGTTTATATCCATTAGATAAAAATACAG

GAGAAGTCTTTACCAAAGATATTTTTAGTCAAATTAAAATTACTGATAAT

GAGTTTAGCGATAAAAAATTAGTAAGAAAAAAAGCTATAGAGGGCTTTAA
```

-continued

```
CACGCATAGACAAATGACTAGAGATGGCATTTATGCAGAAAATTACCTAC

CAATACTAATCCATAAAGAACTAAATGAAGTTAGAAAAGGCTATACTTGG

AAAAATAGTGAAGAAATAAAAATATTCAAAGGTAAAAAGTACGATATACA

ACAATTGAATAACCTTGTGTATTGTCTAAAATTTGTAGATAAACCTATAT

CTATAGATATACAAATTAGTACCTTAGAAGAGTTAAGAAATATATTAACA

ACAAATAATATAGCTGCTACAGCAGAATACTATTATATAAATCTAAAAAC

CCAAAAATTACATGAGTATTATATCGAAAACTATAATACTGCCTTAGGTT

ATAAAAAATACAGTAAAGAAATGGAGTTTTTGAGAAGCTTAGCTTATCGT

AGCGAAAGGGTAAAAATTAAATCAATAGATGATGTAAAGCAGGTTTTGGA

TAAGGATAGTAACTTTATCATCGGTAAGATTACTTTACCATTTAAAAAAG

AGTGGCAAAGACTATATCGTGAGTGGCAAAATACAACTATCAAAGATGAT

TATGAGTTTTTAAAATCATTCTTTAATGTTAAAAGTATTACTAAGTTGCA

TAAAAAAGTTAGAAAAGATTTCTCTTTACCTATTTCTACAAATGAAGGTA

AATTCCTGGTCAAAAGAAAAACATGGGATAACAATTTTATCTATCAGATA

TTAAATGATTCTGATTCTAGAGCAGACGGAACAAAGCCATTTATTCCAGC

TTTTGACATTTCTAAAAATGAAATAGTCGAAGCCATAATTGATTCATTTA

CATCAAAAAATATTTTTTGGCTGCCTAAAAATATAGAATTACAAAAGGTG

GATAATAAAAACATTTTTGCTATAGATACTAGTAAATGGTTCGAAGTAGA

AACACCTAGTGATCTTAGAGACATTGGAATAGCAACAATTCAATACAAGA

TAGATAATAATTCTCGCCCTAAAGTCAGAGTTAAACTTGATTATGTTATC

GATGATGATAGTAAGATAAATTATTTTATGAATCATTCTTTATTAAAATC

AAGATATCCTGACAAAGTTTTAGAAATTTTAAAACAATCAACTATTATAG

AATTTGAAAGTTCAGGTTTTAATAAAACTATCAAAGAAATGCTTGGTATG

AAATTAGCAGGTATTTTATAATGAAACATCTAATAATTAG
``` scaRNA sequence (SEQ ID NO: 3)

```
GUUGUUAGAUUAUUUGGUAUGUACUUGUGUUAGUUUAAAGUAGCUAGAAA

AUUCACUUUUAGACCUACUUAUUUUU
``` tracrRNA sequence (SEQ ID NO: 4)

```
GUACCAAAUAAUUAAUGCUCUGUAAUCAUUUAAAAGUAUUUUGAACGGAC

CUCUGUUUGACACGUCUGAAUAACUAAAAAGCAAAAAUUUGCCACCUAAG

UGGCUUUUUUU
```

CRISPR-CAS Components are Involved in Evasion of TLR2

Because Cas9, the tracrRNA, and the scaRNA regulate the expression of the BLP FTN_1103, and BLPs are ligands for host TLR2, whether these CRISPR-CAS components were involved in evasion of TLR2 were studied. Membrane protein fractions of the tracrRNA and scaRNA mutants stimulated increased TLR2-dependent secretion of the proinflammatory cytokine IL-6, similar to those from the cas9 mutant (FIG. 3*a*). This response was rescued in double mutants lacking FTN_1103, indicating that overexpression of FTN_1103 in these strains was largely responsible for the increased TLR2 signaling (FIG. 3*a*). Mutants lacking cas9, tracrRNA, or the scaRNA also elicited enhanced TLR2-dependent IL-6 secretion during macrophage infection compared to wild-type *F. novicida*, which was dependent on FTN_1103 (FIG. 3*b*). This is in contrast to mutants in other CAS genes, the crRNA array, or a mutant lacking only FTN_1103, which did not alter TLR2 signaling. Together these data indicate that CRISPR-CAS component-mediated suppression of BLP facilitates evasion of TLR2.

Induction of Cas9, tracrRNA, and scaRNA Expression when the Bacteria are in the Phagosome To determine if repression of FTN_1103 was an active evasion process, we analyzed the temporal expression of CRISPR-CAS components during intracellular infection. We found that FTN_1103 expression significantly decreased when the bacteria were in the phagosome (FIG. 3*c*), directly correlating with the roughly 100-fold induction of cas9, tracrRNA, and scaRNA (FIG. 3*d-f*). In the absence of Cas9, tracrRNA, or scaRNA, the temporal repression of FTN_1103 was abrogated (FIG. 3*c*). These data indicate that together, cas9, tracrRNA, and scaRNA are induced during intracellular infection, allowing temporal repression of FTN_1103 when the bacteria are in the proximity of TLR2 in the phagosome, thus facilitating evasion of this innate immune pathway.

Bacteria with Mutant Cas9 as Vaccines

Competitive infections with wild-type *F. novicida*, were performed with cas9, tracrRNA or scaRNA deletion mutants. Female C57BL/6 mice were infected subcutaneously with $1\times10^5$ cfu of wildtype and the indicated mutant strain of *F. novicida* at a 1:1 ratio in sterile PBS. At 48 hours postinfection, spleens were harvested and bacteria enumerated. For survival experiments, mice were infected subcutaneously with $1\times10^5$ cfu and sacrificed when they appeared moribund. For vaccination experiments, mice were infected subcutaneously with $1\times10^5$ cfu of the indicated mutant strain of *F. novicida* in sterile PBS, and challenged subcutaneously with $1\times10^7$ cfu wildtype *F. novicida* 28 days later.

All three mutants were highly attenuated (1,000 to 10,000 fold) compared to wildtype (FIG. 4*a*), indicating that all three components are important for *F. novicida* virulence. This attenuation was significantly rescued by deletion of FTN_1103 from the mutants. Notably, mutants lacking the crRNA array or other CAS genes were not attenuated, correlating with their ability to repress FTN_1103. The cas9, tracrRNA, and scaRNA mutants were also highly attenuated when inoculated individually, as they were unable to cause lethality even at 100×LD50 doses, while mice infected with wild-type rapidly succumbed to disease (FIG. 4*b*). The mice surviving this initial infection might be protected against subsequent lethal challenge with *F. novicida*. While naïve mice rapidly succumbed to a challenge, mice immunized with cas9, tracrRNA or scaRNA mutants were completely protected (FIG. 4*c*). This demonstrates that mutants lacking these CRISPR-CAS components can efficiently vaccinate mice. Given that CRISPR systems of other pathogens may also contribute to virulence by regulating endogenous mRNA, mutants of these genes may represent attractive vaccine strains in numerous virulent bacteria.

*Francisella novicida* Cas9 is Expressed and Produced in Human Cells

Human hepatocellular carcinoma cells (Huh7.5 cells) were transfected with the pcDNA3.3 eukaryotic expression vector, containing the open reading frame for an HA epitope tagged human codon optimized *F. novicida* Cas9 (FnCas9), driven by the CMV promoter. A) Total RNA was extracted and qRT-PCR was performed for FnCas9 transcript and normalized the gapdh. B) Total protein was extracted, separated by SDS-PAGE, and analyzed by western blot using anti-HA to detect FnCas9 and anti-GAPDH, as a loading control.

```
Human Codon Optimized Francisella novicida Cas9
(gene locus FTN_0757)
                                      (SEQ ID NO: 9)
ATGAACTTTAAGATCCTCCCTATTGCCATCGACCTGGGCGTGAAGAACAC

CGGCGTGTTTAGCGCCTTTTACCAGAAGGGCACCAGCCTGGAGAGACTGG

ATAATAAGAACGGCAAGGTGTATGAGCTCAGCAAGGACAGCTATACCCTG

CTCATGAATAACAGGACCGCTAGAAGGCACCAAAGAAGAGGCATCGACAG

AAAGCAGCTGGTCAAGAGACTGTTCAAACTGATTTGGACAGAGCAACTGA

ACCTGGAGTGGGATAAGGACACCCAGCAGGCTATCTCCTTCCTCTTCAAC

AGGAGAGGCTTCAGCTTCATTACCGACGGCTACTCCCCTGAGTATCTGAA

CATTGTCCCCGAACAGGTCAAGGCCATCCTGATGGACATCTTTGACGACT

ACAACGGAGAGGATGATCTCGACTCCTATCTGAAGCTGGCTACCGAACAG

GAAAGCAAGATTTCCGAGATCTACAACAAGCTCATGCAAAAGATTCTGGA

ATTCAAGCTCATGAAGCTGTGTACCGATATCAAGGACGACAAGGTCAGCA

CCAAAACCCTCAAAGAAATCACCAGCTATGAATTTGAGCTGCTGGCCGAT

TACCTGGCTAATTACAGCGAGAGCCTGAAGACCCAGAAGTTCAGCTATAC

CGATAAGCAAGGCAATCTCAAGGAGCTGAGCTACTATCACCATGACAAGT

ACAATATTCAGGAGTTTCTGAAGAGGCATGCTACCATCAATGATAGGATC

CTCGACACACTGCTCACCGATGACCTGGATATCTGGAACTTTAACTTTGA

GAAATTCGACTTTGATAAGAATGAAGAAAAGCTGCAAAATCAGGAAGACA

AGGATCACATTCAGGCTCACCTGCACCACTTCGTCTTCGCCGTCAACAAG

ATCAAGAGCGAAATGGCTTCCGGAGGCAGGCACAGGAGCCAGTACTTCCA

GGAAATCACCAACGTCCTGGACGAGAACAACCACCAGGAAGGCTACCTCA

AGAATTTCTGTGAGAACCTGCACAACAAGAAATATAGCAACCTGTCCGTG

AAAAACCTCGTCAACCTCATCGGCAACCTGAGCAATCTGGAGCTGAAGCC

CCTGAGGAAGTACTTCAACGACAAGATTCATGCCAAGGCTGACCACTGGG

ACGAGCAGAAGTTCACAGAGACATACTGTCACTGGATCCTGGGAGAATGG

AGGGTGGGCGTCAAAGACCAGGACAAAAAAGATGGAGCTAAGTACAGCTA

CAAAGATCTGTGTAATGAGCTCAAACAGAAGGTGACAAAAGCCGGACTGG

TGGACTTCCTGCTGGAGCTGGATCCCTGCAGGACAATTCCCCCCTATCTC

GACAACAATAACAGGAAGCCTCCCAAGTGCCAAAGCCTCATCCTCAACCC

CAAGTTCCTCGACAATCAGTATCCCAATTGGCAGCAGTACCTGCAAGAAC

TGAAAAAACTGCAAAGCATTCAAAACTACCTCGATTCCTTCGAGACCGAC

CTCAAAGTCCTCAAAAGCAGCAAGGACCAACCCTACTTCGTCGAATACAA

GAGCAGCAACCAGCAGATCGCCTCCGGACAGAGAGACTACAAAGACCTCG

ACGCCAGGATTCTGCAATTCATCTTCGACAGAGTCAAGGCTTCCGACGAA

CTGCTGCTGAATGAAATCTATTTTCAAGCTAAAAAGCTCAAGCAGAAAGC

CAGCAGCGAACTCGAAAAACTGGAGTCCTCCAAGAAACTCGACGAGGTGA

TTGCCAATAGCCAACTCAGCCAGATCCTGAAGAGCCAGCATACAAATGGC

ATCTTCGAGCAAGGCACATTTCTGCATCTGGTGTGTAAATACTACAAACA
```

-continued

```
AAGACAGAGGGCTAGGGACAGCAGACTCTATATCATGCCCGAGTACAGAT
ACGATAAAAAACTGCATAAATACAACAACACCGGCAGGTTTGACGACGAT
AACCAACTGCTCACCTACTGCAACCACAAGCCTAGGCAAAAAAGGTATCA
GCTGCTGAACGACCTGGCTGGAGTGCTCCAAGTCTCCCCTAATTTCCTCA
AGGATAAAATTGGATCCGACGATGACCTCTTCATCTCCAAGTGGCTGGTC
GAGCACATCAGAGGCTTCAAGAAGGCCTGCGAAGATTCCCTGAAAATCCA
GAAGGACAACAGGGGACTCCTGAATCATAAGATTAATATCGCTAGAAATA
CCAAGGGCAAATGCGAGAAGGAGATCTTCAACCTGATCTGCAAAATCGAA
GGCTCCGAGGATAAGAAAGGCAACTATAAGCATGGCCTGGCTTATGAGCT
CGGAGTGCTCCTGTTCGGAGAGCCCAATGAGGCCTCCAAGCCTGAATTTG
ACAGGAAGATCAAGAAGTTTAATAGCATCTACTCCTTCGCCCAGATCCAA
CAAATCGCCTTCGCTGAAAGGAAGGGCAACGCTAACACCTGCGCCGTGTG
CAGCGCTGATAATGCTCACAGGATGCAGCAGATCAAGATCACAGAACCCG
TGGAAGACAATAAAGACAAGATCATCCTCAGCGCTAAGGCTCAGAGACTG
CCCGCTATTCCTACAAGAATCGTGGACGGAGCCGTCAAGAAAATGGCCAC
CATCCTGGCCAAAAACATCGTGGATGATAATTGGCAAAATATTAAACAGG
TCCTGTCCGCCAAGCACCAGCTCCACATTCCCATCATCACCGAGTCCAAT
GCTTTCGAGTTCGAACCCGCCCTGGCTGACGTGAAAGGCAAATCCCTCAA
GGACAGAAGAAAGAAGGCCCTGGAGAGAATTTCCCCTGAGAACATCTTTA
AGGACAAAAATAACAGAATTAAAGAGTTTGCTAAGGGAATTTCCGCCTAC
AGCGGCGCCAATCTGACAGATGGCGACTTCGATGCGCTAAAGAAGAGCT
CGACCACATCATTCCCAGAAGCCACAAGAAGTATGGAACCCTCAACGATG
AGGCCAACCTCATCTGCGTCACCAGGGGCGACAATAAAAATAAAGGCAAT
AGGATCTTCTGTCTGAGAGACCTGGCCGATAACTACAAACTGAAACAGTT
CGAAACCACCGACGACCTGGAGATTGAGAAGAAAATCGCCGACACCATCT
GGGACGCTAATAAAAAAGACTTTAAGTTCGGAAACTACAGGAGCTTCATT
AACCTGACACCCCAGGAACAGAAAGCCTTTAGGCATGCCCTCTTTCTGGC
CGATGAGAACCCTATCAAGCAAGCCGTCATCAGGGCCATCAACAACAGGA
ATAGGACCTTCGTCAATGGCACCCAGAGGTACTTTGCCGAGGTGCTGGCC
AATAACATCTATCTCAGGGCTAAAAAGGAGAATCTCAATACAGACAAAAT
CTCCTTTGACTATTTTGGAATCCCTACCATCGGAAATGGCAGGGGAATCG
CTGAGATTAGACAGCTGTACGAGAAAGTCGACAGCGATATCCAAGCCTAC
GCCAAGGGAGATAAGCCTCAGGCTTCCTATAGCCACCTCATCGACGCTAT
GCTGGCCTTTTGCATCGCCGCCGACGAGCACAGAAATGATGGCTCCATCG
GACTGGAAATCGACAAGAATTACAGCCTCTACCCCCTCGACAAAAACACA
GGAGAGGTGTTCACAAAAGATATTTTCAGCCAGATTAAGATTACAGACAA
CGAATTTAGCGATAAGAAACTGGTGAGAAAGAAAGCTATCGAGGGATTTA
ATACCCATAGGCAAATGACCAGGGACGGCATTTACGCTGAGAACTATCTC
CCCATCCTCATCCACAAGGAACTGAACGAAGTCAGAAAAGGATATACCTG
GAAAAATAGCGAGGAAATTAAGATTTTCAAAGGAAAAAAGTATGACATCC
AGCAGCTCAACAACCTCGTGTATTGCCTCAAGTTCGTGGACAAGCCCATT
TCCATCGACATCCAGATCAGCACACTGGAAGAGCTGAGGAATATCCTGAC
CACAAATAACATTGCCGCTACCGCTGAGTATTATTACATTAATCTCAAAA
CACAGAAACTGCATGAATATTACATCGAGAACTACAATACCGCCCTGGGC
TATAAGAAGTATTCCAAGGAAATGGAGTTCCTCAGGTCCCTCGCCTATAG
GAGCGAGAGGGTGAAGATTAAGAGCATCGACGATGTCAAGCAGGTGCTGG
ACAAGGATAGCAACTTCATTATTGGAAAAATCACACTCCCCTTTAAGAAG
GAGTGGCAGAGGCTGTACAGGGAGTGGCAAAACACCACAATCAAGGACGA
TTACGAGTTCCTGAAGAGCTTCTTTAACGTGAAGAGCATTACAAAGCTGC
ACAAGAAGGTCAGGAAAGACTTCAGCCTCCCCATTAGCACCAACGAGGGA
AAGTTCCTGGTGAAGAGGAAGACCTGGGACAACAACTTCATCTACCAGAT
CCTCAATGACTCCGACAGCAGGGCCGACGGCACAAAGCCCTTTATCCCTG
CCTTCGACATCAGCAAGAACGAAATCGTGGAGGCCATCATCGATTCCTTT
ACCAGCAAAAACATTTTCTGGCTGCCCAAAAATATTGAACTCCAGAAGGT
CGACAACAAAAACATCTTTGCTATCGACACATCCAAATGGTTTGAAGTCG
AGACACCTTCCGACCTGAGGGATATCGGAATTGCCACCATTCAATATAAG
ATCGACAATAATAGCAGGCCTAAAGTGAGGGTCAAACTCGACTACGTGAT
CGACGACGACAGCAAGATCAACTACTTCATGAACCACAGCCTGCTGAAGT
CCAGGTATCCCGACAAGGTCCTCGAAATCCTCAAGCAGAGCACCATCATT
GAATTTGAGTCCAGCGGATTCAACAAGACAATCAAAGAGATGCTGGGCAT
GAAACTCGCCGGCATCTATAACGAGACCAGCAATAAC
```

FnCas9 can be Directed to Restrict Viral Infection in a Sequence-Specific Fashion.

Targeting rgRNA interacting with the portion of the indicated portion of the HCV genome, either 5' UTR (A) or the 3' UTR (B) is illustrated in FIG. 9. Targeting rgRNA is (SEQ ID NO: 12)
5'-G<u>UAUCAGGCAGUACCACAAGCUCGUAAUUAAUAAACCAUGAAGUA</u>
<u>UGGUUUAUUAGAUUGUUG</u>AAGGCUAGUCCGUUAUCAACUUG-3'.

Underlined indicates the targeting region (SEQ ID NO: 10) (See FIG. 9) which can be modified to 19 bases (or more) to create base pairing with the desired RNA target. Double underlined (SEQ ID NO: 11) indicates the *F. novicida* Cas9 binding region. This forms a double stranded structure (See FIG. 9)

Figure 9A:
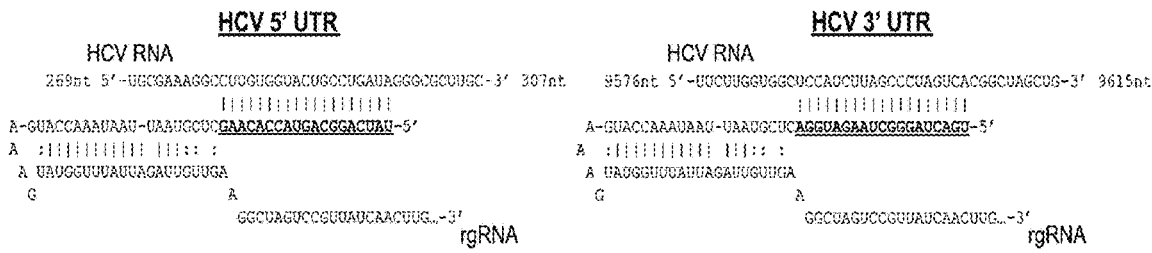
FIG. 9A shows data indicating FnCas9 can be directed to restrict viral infection in a sequence-specific fashion. Schematic diagram of the targeting rgRNA (SEQ ID NO:43) interacting with the portion of the indicated portion of the HCV genome 5' UTR (SEQ ID NO:42). Schematic diagram of the targeting rgRNA (SEQ ID NO:45) interacting with the portion of the indicated portion of the HCV genome, 3' UTR (SEQ ID NO:44). Gray highlight is the variable region which dictates specificity of targeting. Double-stranded region determines FnCas9 interaction.
Figure 9B:
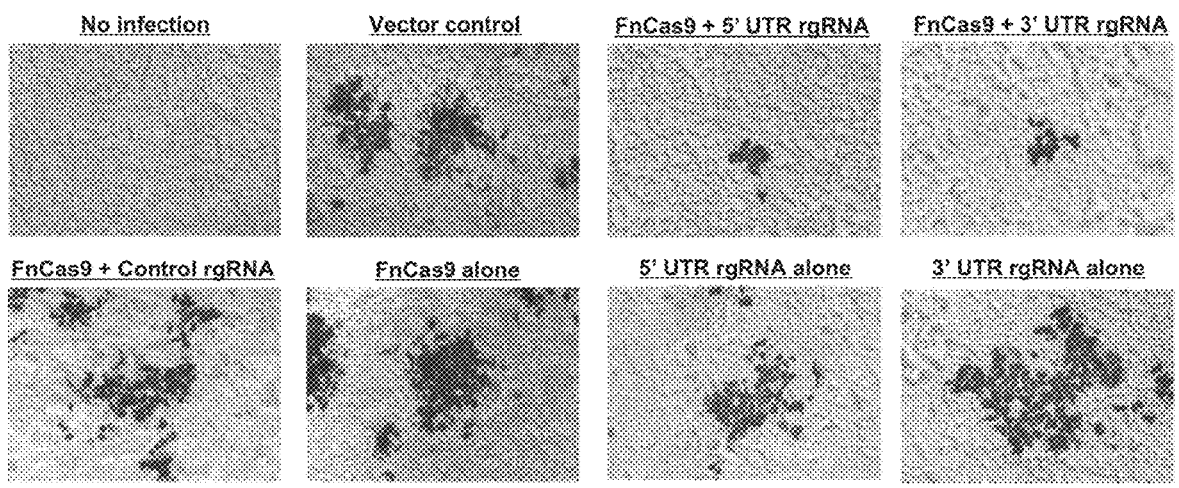
FIG. 9B shows Huh7.5 cells were transfected with the indicated plasmid constructs containing Cas9, the HCV 5' and 3' targeting rgRNAs, the non-specific control targeting rgRNA, or combinations of both. Following transfection, cells were infected with HCV (strain Cp7) and 48 hours post infection, cells were stained with anti-E2 antibody to measure viral protein.
Figure 9C:
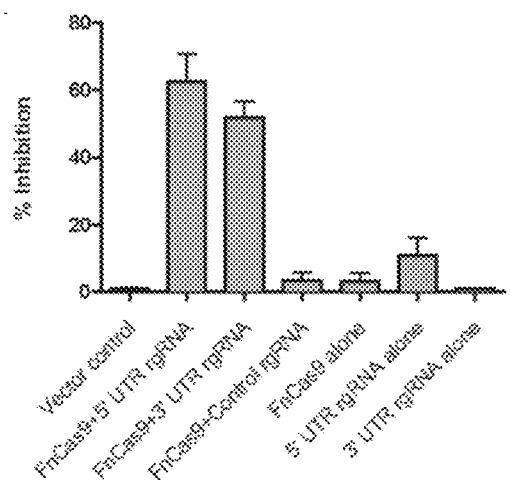
FIG. 9C shows the quantification of E2 staining, reported as percent inhibition compared to non-transfected cells.
Figure 9D:
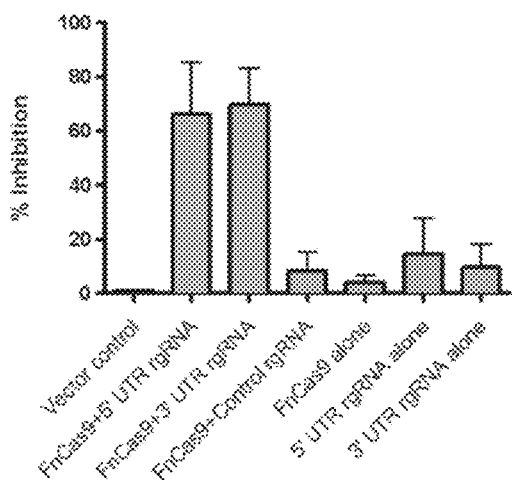
FIG. 9D shows Huh7.5 cells were transfected with the indicated FnCas9 and rgRNA plasmid constructs as above. Cells were then infected with a *Renilla* luciferase producing HCV (Cp7:rluc). At 48 hours post infection, infected cells were lysed and luciferase activity measured. Relative inhibition of luciferase activity compared to non-transfected cells is reported.
Figure 11A:
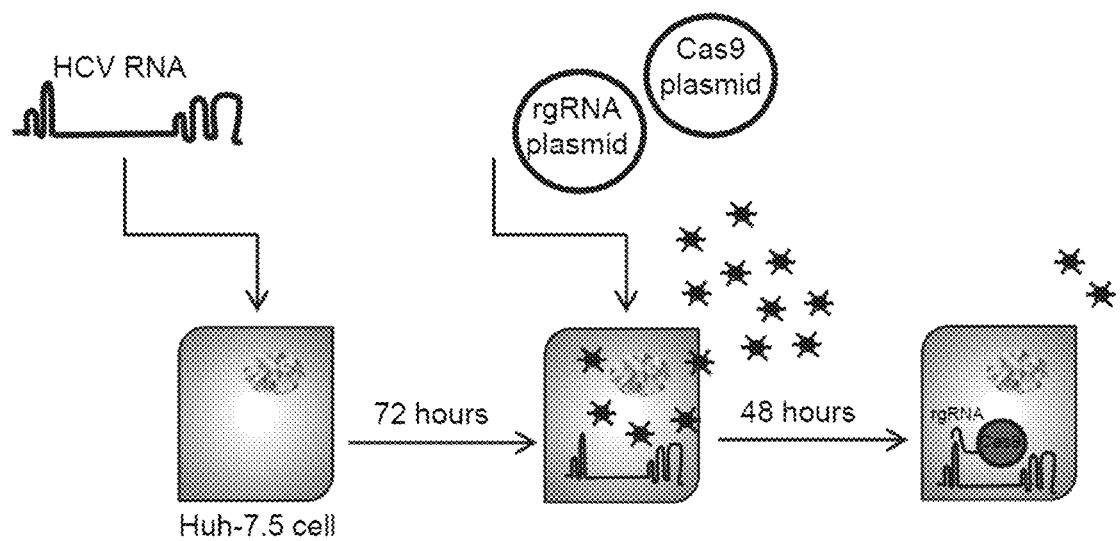
FIG. 11A shows data indicating targeted FnCas9 can rescue HCV viral infection. Schematic of experimental outline. Huh7.5 cells were first transfected with Renilla luciferase producing HCV (Cp7:rluc) RNA and viral infection was allowed to proceed for 72 hours. Infected cells were than transfected with the indicated FnCas9 and rgRNA plasmid constructs as above.
Figure 11B:
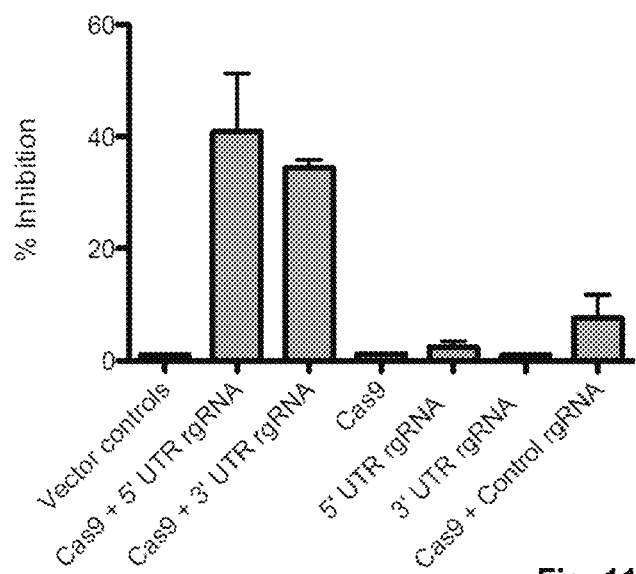
FIG. 11B shows data indicating targeted FnCas9 can rescue HCV viral infection At 48 hours post infection, infected cells were lysed and luciferase activity measured. Relative inhibition of luciferase activity compared to non-transfected cells is reported.

The single underlined region is the variable region which dictates specificity of targeting. Double-stranded region determines FnCas9 interaction. Huh7.5 cells were transfected with the indicated plasmid constructs containing Cas9, the HCV 5' and 3' targeting rgRNAs, the non-specific control targeting rgRNA, or combinations of both. Following transfection, cells were infected with HCV (strain Cp7) and 48 hours post infection, cells were stained with anti-E2 antibody to measure viral protein (FIG. 9C).

Huh7.5 cells were transfected with the indicated FnCas9 and rgRNA plasmid constructs as above. Cells were then infected with a Renilla luciferase producing HCV (Cp7: rluc). At 48 hours post infection, infected cells were lysed and luciferase activity measured. Relative inhibition of luciferase activity compared to non-transfected cells is reported (FIG. 9E).

What we claim:

1. A nucleic acid composition comprising:
   a first nucleic acid sequence comprising a Cas9 gene encoding a Cas9 protein,
   a second nucleic acid sequence comprising
      a first RNA segment that binds, in a eukaryotic cell, to the Cas9 protein, wherein the first RNA segment comprises a double-stranded region and
      a second single-stranded RNA segment that binds to a target nucleic acid,
   wherein the target nucleic acid sequence is genomic RNA or an mRNA transcript from an RNA virus with no DNA stage or is microRNA associated with an oncogene.

2. The nucleic acid composition of claim 1, wherein the Cas9 protein comprises SEQ ID NO: 1 or a conserved variant thereof.

3. The nucleic acid composition of claim 2, wherein the Cas9 protein has an arginine-rich motif, a RuvC-III motif, and a RuvC-IV motif.

4. The nucleic acid composition of claim 1, wherein the Cas9 protein comprises a sequence with at least 40% identity to SEQ ID NO: 1.

5. The nucleic acid composition of claim 1, wherein the first segment forms a hairpin structure.

6. The nucleic acid composition of claim 1, wherein the second segment comprises more than 50 continuous nucleotides configured to hybridize to the target nucleic acid sequence.

7. The nucleic acid composition of claim 1, wherein the target nucleic acid sequence is a genomic RNA from a virus.

8. The nucleic acid composition of claim 1 wherein the target nucleic acid sequence is mRNA or microRNA associated with an oncogene.

9. The nucleic acid composition of claim 1, wherein the Cas9 gene comprises a sequence with 60% or more identity to SEQ ID NO: 9.

10. The nucleic acid composition of claim 7, wherein the virus is influenza A virus including subtype H1N1, influenza B virus, influenza C virus, rotavirus A, rotavirus B, rotavirus C, rotavirus D, rotavirus E, SARS coronavirus, coxsackie A virus, norovirus, Rubella virus, lymphocytic choriomeningitis virus (LCMV), yellow fever virus, measles virus, mumps virus, respiratory syncytial virus, rinderpest virus, California encephalitis virus, hantavirus, rabies virus, ebola virus, marburg virus, hepatitis A virus (HAV), hepatitis C virus (HCV), hepatitis D virus (HDV), or hepatitis E virus (HEV).

11. The nucleic acid composition of claim 1 wherein the Cas9 protein does not include a nuclear localization signal.

12. A recombinant vector comprising the nucleic acid composition of claim 1.

13. A eukaryotic cell comprising
   a mRNA encoding a Cas9 protein, and
   a RNA comprising
      a first segment that binds to the Cas9 protein, wherein the first RNA segment comprises a double-stranded region and
      a second single-stranded segment that binds to a target nucleic acid sequence,
   wherein the target nucleic acid sequence is a genomic RNA or mRNA sequence from a virus, wherein the virus is influenza A virus including subtype H1N1, influenza B virus, influenza C virus, rotavirus A, rotavirus B, rotavirus C, rotavirus D, rotavirus E, SARS coronavirus, coxsackie A virus, norovirus, Rubella virus, lymphocytic choriomeningitis virus (LCMV), yellow fever virus, measles virus, mumps virus, respiratory syncytial virus, rinderpest virus, California encephalitis virus, hantavirus, rabies virus, ebola virus, marburg virus, hepatitis A virus (HAV), hepatitis C virus (HCV), hepatitis D virus (HDV), or hepatitis E virus (HEV).

14. The cell of claim 13 comprising the Cas9 protein complexed with the first segment.

15. The cell of claim 13 that is a mammalian cell.

16. The cell of claim 13 wherein the Cas9 protein does not include a nuclear localization signal.

17. The cell of claim 13, wherein the Cas9 protein is encoded by a gene comprising a sequence with 60% or more identity to SEQ ID NO: 9.

* * * * *